(12) United States Patent
Nambiar et al.

(10) Patent No.: US 12,173,091 B2
(45) Date of Patent: *Dec. 24, 2024

(54) ENZYMATICALLY POLYMERIZED GELLING DEXTRANS

(71) Applicant: NUTRITION & BIOSCIENCES USA 4, INC., Rochester, NY (US)

(72) Inventors: Rakesh Nambiar, West Chester, PA (US); Rong Guan, Wilmington, DE (US); Qiong Cheng, Wilmington, DE (US); Robert Dicosimo, Chadds Ford, PA (US); Jayme L. Paullin, Claymont, DE (US); Yuanfeng Liang, Chadds Ford, PA (US); Charles R. Powley, Wilmington, DE (US); Yefim Brun, Wilmington, DE (US)

(73) Assignee: NUTRITION & BIOSCIENCES USA 4, INC., Wilmington, DE (US)

( * ) Notice: Subject to any disclaimer, the term of this patent is extended or adjusted under 35 U.S.C. 154(b) by 19 days.

This patent is subject to a terminal disclaimer.

(21) Appl. No.: 17/865,904

(22) Filed: Jul. 15, 2022

(65) Prior Publication Data

US 2023/0235096 A1    Jul. 27, 2023

Related U.S. Application Data

(63) Continuation of application No. 16/111,514, filed on Aug. 24, 2018, now Pat. No. 11,390,692, which is a continuation of application No. 14/933,128, filed on Nov. 5, 2015, now Pat. No. 10,059,779.

(60) Provisional application No. 62/075,460, filed on Nov. 5, 2014.

(51) Int. Cl.
| | |
|---|---|
| *C12P 19/08* | (2006.01) |
| *C08B 37/02* | (2006.01) |
| *C08L 5/02* | (2006.01) |
| *C11D 3/22* | (2006.01) |

(52) U.S. Cl.
CPC ............ *C08B 37/0021* (2013.01); *C08L 5/02* (2013.01); *C11D 3/222* (2013.01); *C12P 19/08* (2013.01)

(58) Field of Classification Search
CPC .................................. C12P 19/08; C11D 3/222
See application file for complete search history.

(56) References Cited

U.S. PATENT DOCUMENTS

| | | | | |
|---|---|---|---|---|
| 10,059,779 B2 * | 8/2018 | Nambiar | .................. | C08L 5/02 |
| 11,390,692 B2 * | 7/2022 | Nambiar | ............. | C08B 37/0021 |

* cited by examiner

*Primary Examiner* — Tekchand Saidha

(57) ABSTRACT

Compositions are disclosed herein comprising dextran that comprises (i) 87-93 wt % glucose linked at positions 1 and 6; (ii) 0.1-1.2 wt % glucose linked at positions 1 and 3; (iii) 0.1-0.7 wt % glucose linked at positions 1 and 4; (iv) 7.7-8.6 wt % glucose linked at positions 1, 3 and 6; and (v) about 0.4-1.7 wt % glucose linked at (a) positions 1, 2 and 6, or (b) positions 1, 4 and 6. Aqueous forms of this composition have enhanced viscosity profiles. Further disclosed are methods of using compositions comprising dextran, such as increasing the viscosity of an aqueous composition. Enzymatic reactions for producing dextran are also disclosed.

20 Claims, 4 Drawing Sheets

Figure 1:
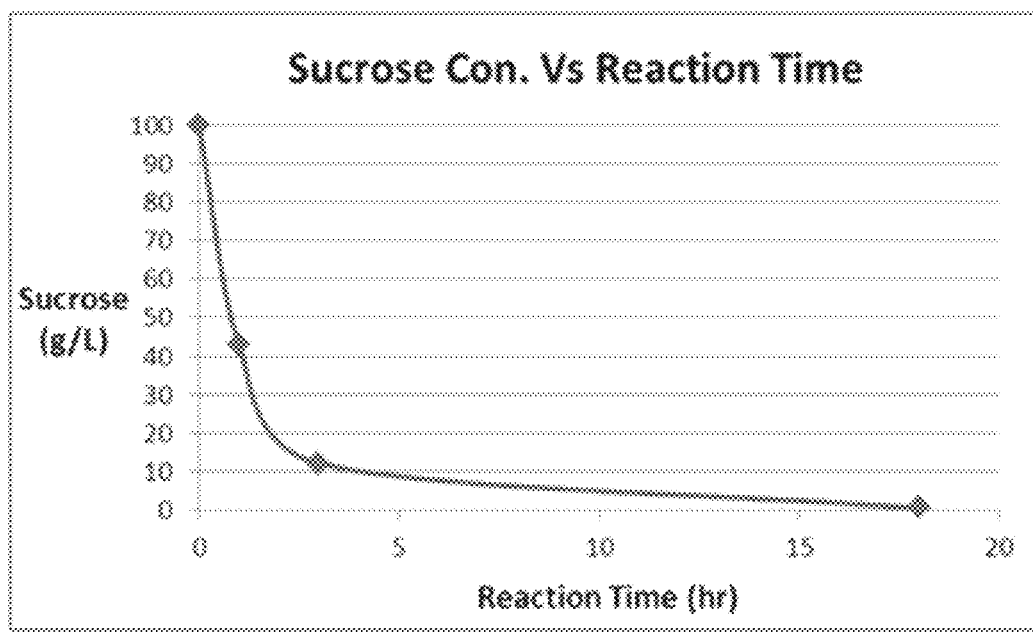

Specification includes a Sequence Listing.

ENZYMATICALLY POLYMERIZED GELLING DEXTRANS

This application is a continuation of U.S. application Ser. No. 16/111,514 (filed Aug. 24, 2018, now U.S. patent Ser. No. 11/390,692), which is a continuation of U.S. application Ser. No. 14/933,128 (filed Nov. 5, 2015, now U.S. patent Ser. No. 10/059,779), which claims the benefit of U.S. Provisional Application No. 62/075,460 (filed Nov. 5, 2014), all of which prior applications are incorporated herein by reference in their entirety.

FIELD OF INVENTION

The present disclosure is in the field of polysaccharides. For example, the disclosure pertains to certain dextran polymers, reactions comprising glucosyltransferase enzymes that synthesize these polymers, and use of the polymers in various applications.

REFERENCE TO SEQUENCE LISTING SUBMITTED ELECTRONICALLY

The official copy of the sequence listing has been submitted electronically via EFS-Web or Patent Center as a file named CL6294USCNT2_SequenceListing.xml created on Feb. 21, 2023 and having a size of 69 kilobytes. The sequence listing contained in this file is part of the specification and is herein incorporated by reference in its entirety.

BACKGROUND

Driven by a desire to find new structural polysaccharides using enzymatic syntheses or genetic engineering of microorganisms, researchers have discovered polysaccharides that are biodegradable and can be made economically from renewably sourced feedstocks. One such family of polysaccharides are alpha-glucans, which are polymers comprising glucose monomers linked by alpha-glycosidic bonds.

Dextrans represent a family of complex, branched alpha-glucans generally comprising chains of alpha-1,6-linked glucose monomers, with periodic side chains (branches) linked to the straight chains by alpha-1,3-linkage (Ioan et al., *Macromolecules* 33:5730-5739). Production of dextrans is typically done through fermentation of sucrose with bacteria (e.g., *Leuconostoc* or *Streptococcus* species), where sucrose serves as the source of glucose for dextran polymerization (Naessens et al., *J. Chem. Technol. Biotechnol.* 80:845-860; Sarwat et al., *Int. J. Biol. Sci.* 4:379-386; Onilude et al., *Int. Food Res. J.* 20:1645-1651). Although dextrans are used in several applications given their high solubility in water (e.g., adjuvants, stabilizers), this high solubility can negatively affect their general utility as thickening agents in hydrocolloid applications.

Thus, there is interest in developing new, higher viscosity dextran polymers that are more amenable to high viscosity applications. In turn, there is also interest in identifying glucosyltransferase enzymes that can synthesize such dextran polymers.

SUMMARY OF INVENTION

In one embodiment, the disclosure concerns a composition comprising dextran that comprises:
(i) about 87-93 wt % glucose linked at positions 1 and 6;
(ii) about 0.1-1.2 wt % glucose linked at positions 1 and 3;
(iii) about 0.1-0.7 wt % glucose linked at positions 1 and 4;
(iv) about 7.7-8.6 wt % glucose linked at positions 1, 3 and 6; and
(v) about 0.4-1.7 wt % glucose linked at:
   (a) positions 1, 2 and 6, or
   (b) positions 1, 4 and 6;
wherein the weight-average molecular weight (Mw) of the dextran is about 50-200 million Daltons, the z-average radius of gyration of the dextran is about 200-280 nm, and the dextran optionally is not a product of a *Leuconostoc mesenteroides* glucosyltransferase enzyme.

In another embodiment, the dextran comprises: (i) about 89.5-90.5 wt % glucose linked at positions 1 and 6; (ii) about 0.4-0.9 wt % glucose linked at positions 1 and 3; (iii) about 0.3-0.5 wt % glucose linked at positions 1 and 4; (iv) about 8.0-8.3 wt % glucose linked at positions 1, 3 and 6; and (v) about 0.7-1.4 wt % glucose linked at: (a) positions 1, 2 and 6, or (b) positions 1, 4 and 6.

In another embodiment, the dextran comprises chains (long chains) linked together within a branching structure, wherein said chains are similar in length and comprise substantially alpha-1,6-glucosidic linkages. The average length of the chains is about 10-50 monomeric units in another embodiment.

In another embodiment, the dextran is a product of a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17.

In another embodiment, the composition is an aqueous composition having a viscosity of at least about 25 cPs.

In another embodiment, the Mw of the dextran is about 80-120 million Daltons.

In another embodiment, the z-average radius of gyration of the dextran is about 230-250 nm.

In another embodiment, the composition is in the form of a food product, personal care product, pharmaceutical product, household product, or industrial product. In another embodiment, the composition is in the form of a confectionery.

In another embodiment, the disclosure concerns a method for increasing the viscosity of an aqueous composition. This method comprises contacting at least one dextran compound as disclosed herein with an aqueous composition.

The contacting step in this method results in increasing the viscosity of the aqueous composition, in comparison to the viscosity of the aqueous composition before the contacting step.

In another embodiment, the disclosure concerns a method of treating a material. This method comprises contacting a material with an aqueous composition comprising at least one dextran compound disclosed herein.

In another embodiment, the disclosure concerns an enzymatic reaction comprising water, sucrose and a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17, wherein the glucosyltransferase enzyme synthesizes a dextran compound as disclosed herein.

In another embodiment, the disclosure concerns a method of producing dextran comprising the step of contacting at least water, sucrose, and a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17, thereby producing dextran as disclosed herein. This dextran can optionally be isolated.

In another embodiment, the viscosity of the dextran produced in the method is increased by decreasing the amount of sucrose in step (a).

BRIEF DESCRIPTION OF THE DRAWINGS AND SEQUENCES

FIG. 1: HPLC analysis of sucrose consumption by a glucosyltransferase reaction comprising 100 g/L sucrose and a 0768 gtf (SEQ ID NO:1). Refer to Example 2.

Figure 2A:
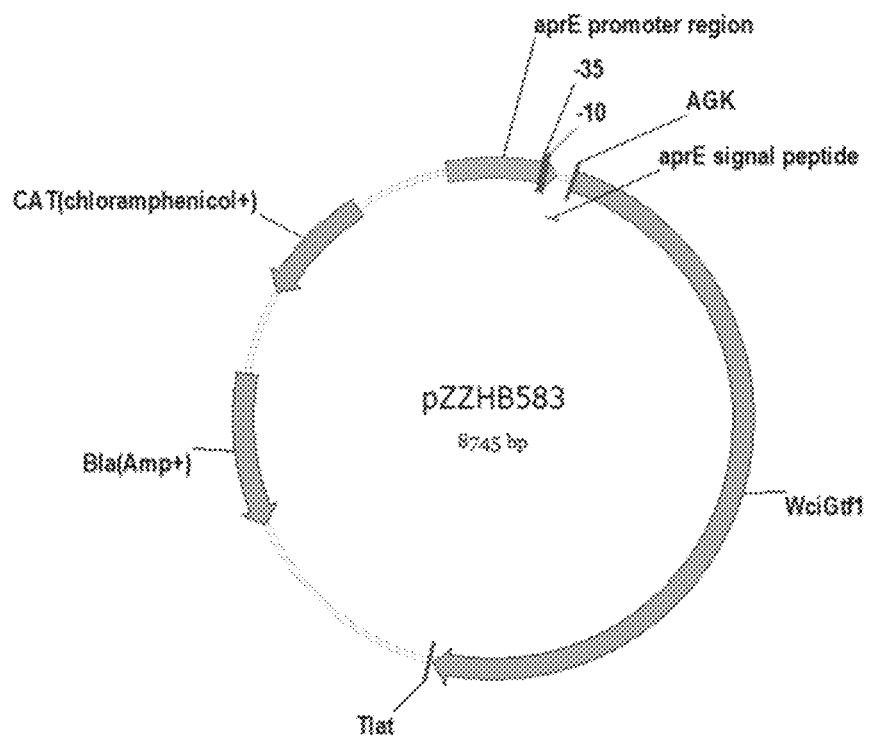

FIG. 2A: Map of plasmid pZZHB583 used to express 2919 gtf (SEQ ID NO:5) in *B. subtilis*. Refer to Example 3.

Figure 2B:
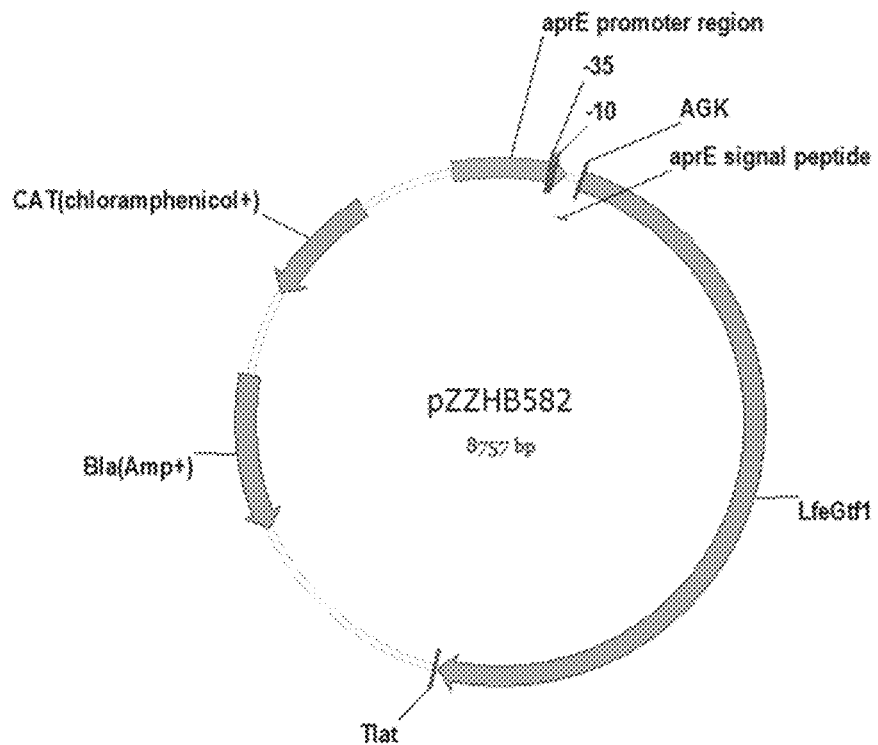

FIG. 2B: Map of plasmid pZZHB582 used to express 2918 gtf (SEQ ID NO:9) in *B. subtilis*. Refer to Example 4.

Figure 2C:
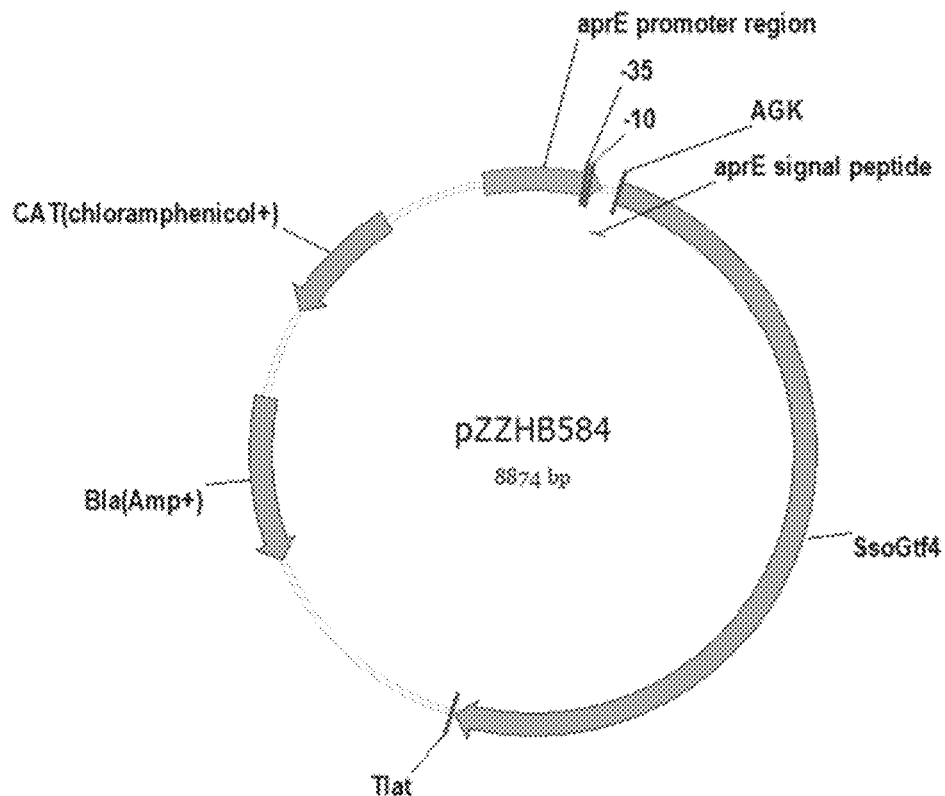

FIG. 2C: Map of plasmid pZZHB584 used to express 2920 gtf (SEQ ID NO:13) in *B. subtilis*. Refer to Example 5.

Figure 2D:
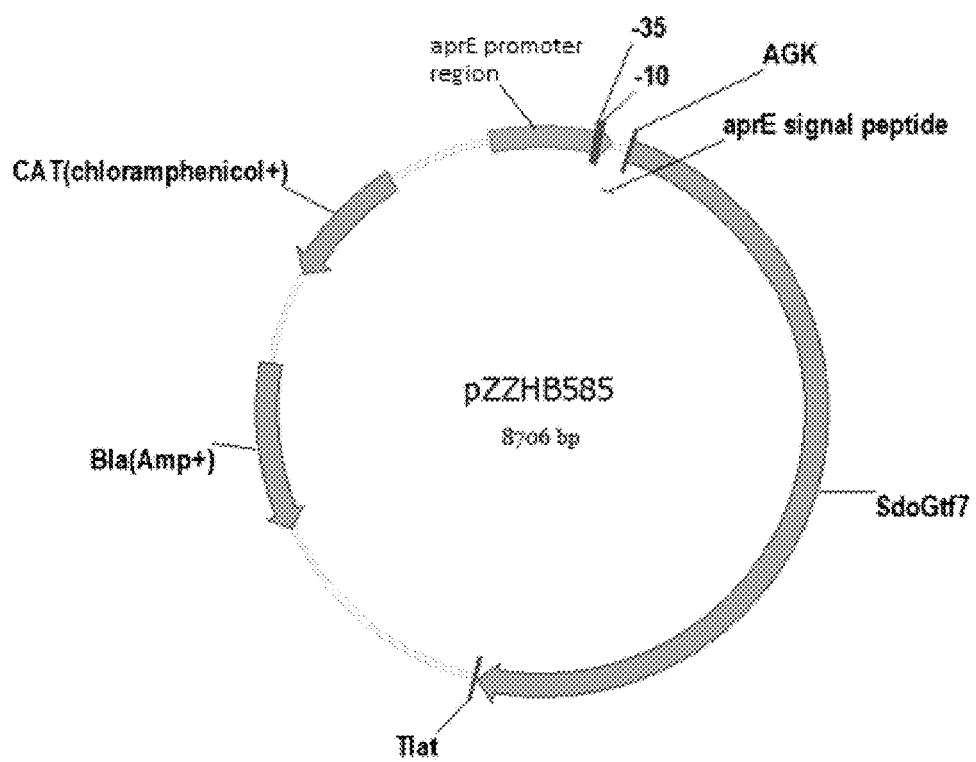

FIG. 2D: Map of plasmid pZZHB585 used to express 2921 (SEQ ID NO:17) gtf in *B. subtilis*. Refer to Example 6.

Figure 3:
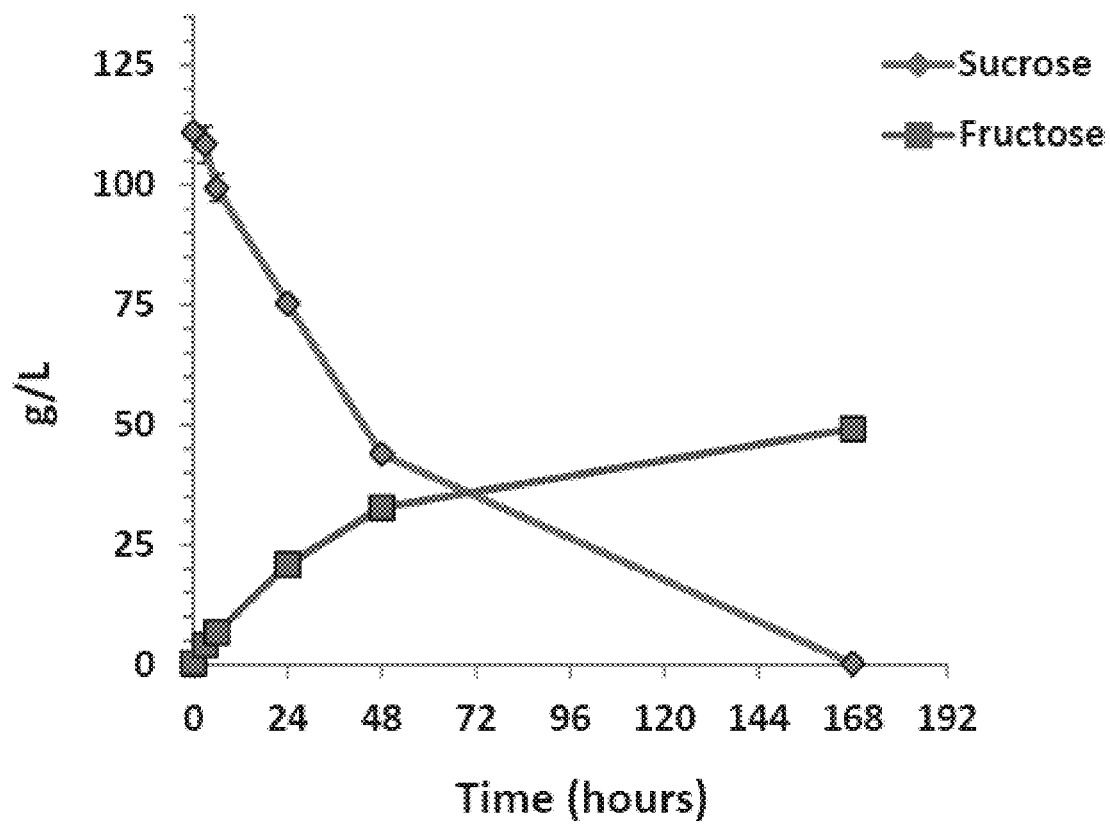

FIG. 3: HPLC analysis of sucrose consumption by a reaction comprising a commercially available dextran sucrase. Refer to Example 7.

TABLE 1

Summary of Nucleic Acid and Protein SEQ ID Numbers

| Description | Nucleic acid SEQ ID NO. | Protein SEQ ID NO. |
| --- | --- | --- |
| "0768 gtf", *Leuconostoc pseudomesenteroides*. Mature form of GENBANK Identification No. 497964659. | | 1 (1447 aa) |
| "0768 gtf", *Leuconostoc pseudomesenteroides*. Mature form of GENBANK Identification No. 497964659, but including a start methionine and additional N- and C-terminal amino acids. | | 2 (1457 aa) |
| WciGtf1, *Weissella cibaria*. Full length form comprising signal sequence. GENBANK Accession No. ZP_08417432 (amino acid sequence). | 3 (4347 bases) | 4 (1448 aa) |
| "2919 gtf", *Weissella cibaria*. Mature form of GENBANK Identification No. ZP_08417432. | | 5 (1422 aa) |
| "2919 gtf", *Weissella cibaria*. Sequence optimized for expression in *B. subtilis*. Encodes 2919 gtf with a heterologous signal sequence and additional N-terminal amino acids. | 6 (4269 bases) | |
| LfeGtf1, *Lactobacillus fermentum*. Full length form comprising signal sequence. GENBANK Accession No. AAU08008 (amino acid sequence). | 7 (4392 bases) | 8 (1463 aa) |
| "2918 gtf", *Lactobacillus fermentum*. Mature form of GENBANK Identification No. AAU08008. | | 9 (1426 aa) |
| "2918 gtf", *Lactobacillus fermentum*. Sequence optimized for expression in *B. subtilis*. Encodes 2918 gtf with a heterologous signal sequence and additional N-terminal amino acids. | 10 (4281 bases) | |
| SsoGtf4, *Streptococcus sobrinus*. Full length form comprising signal sequence. GENBANK Accession No. AAX76986 (amino acid sequence). | 11 (4521 bases) | 12 (1506 aa) |
| "2920 gtf", *Streptococcus sobrinus*. Mature form of GENBANK Identification No. AAX76986. | | 13 (1465 aa) |
| "2920 gtf", *Streptococcus sobrinus*. Sequence optimized for expression in *B. subtilis*. Encodes 2920 gtf with a heterologous signal sequence and additional N-terminal amino acids. | 14 (4398 bases) | |
| SdoGtf7, *Streptococcus downei*. Full length form comprising signal sequence. GENBANK Accession No. ZP_08549987.1 (amino acid sequence). | 15 (4360 bases) | 16 (1453 aa) |
| "2921 gtf", *Streptococcus downei*. Mature form of GENBANK Identification No. ZP_08549987.1. | | 17 (1409 aa) |
| "2921 gtf", *Streptococcus downei*. Sequence optimized for expression in *B. subtilis*. Encodes 2921 gtf with a heterologous signal sequence and additional N-terminal amino acids. | 18 (4230 bases) | |

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

The term "glucan" herein refers to a polysaccharide of D-glucose monomers that are linked by glucosidic linkages, which are a type of glycosidic linkage. An "alpha-glucan" herein refers to a glucan in which the constituent D-glucose monomers are alpha-D-glucose monomers.

The terms "dextran", "dextran polymer", "dextran compound" and the like are used interchangeably herein and refer to complex, branched alpha-glucans generally comprising chains of substantially (mostly) alpha-1,6-linked glucose monomers, with side chains (branches) linked mainly by alpha-1,3-linkage. The term "gelling dextran" herein refers to the ability of one or more dextrans disclosed herein to form a viscous solution or gel-like composition (i)

during enzymatic dextran synthesis and, optionally, (ii) when such synthesized dextran is isolated (e.g., >90% pure) and then placed in an aqueous composition.

Dextran "long chains" herein can comprise "substantially [or mostly] alpha-1,6-glucosidic linkages", meaning that they can have at least about 98.0% alpha-1,6-glucosidic linkages in some aspects. Dextran herein can comprise a "branching structure" (branched structure) in some aspects. It is contemplated that in this structure, long chains branch from other long chains, likely in an iterative manner (e.g., a long chain can be a branch from another long chain, which in turn can itself be a branch from another long chain, and so on). It is contemplated that long chains in this structure can be "similar in length", meaning that the length (DP [degree of polymerization]) of at least 70% of all the long chains in a branching structure is within plus/minus 30% of the mean length of all the long chains of the branching structure.

Dextran in some embodiments can also comprise "short chains" branching from the long chains, typically being one to three glucose monomers in length, and comprising less than about 10% of all the glucose monomers of a dextran polymer. Such short chains typically comprise alpha-1,2-, alpha-1,3-, and/or alpha-1,4-glucosidic linkages (it is believed that there can also be a small percentage of such non-alpha-1,6 linkages in long chains in some aspects).

The terms "glycosidic linkage" and "glycosidic bond" are used interchangeably herein and refer to the covalent bond that joins a carbohydrate molecule to another carbohydrate molecule. The terms "glucosidic linkage" and "glucosidic bond" are used interchangeably herein and refer to a glycosidic linkage between two glucose molecules. The term "alpha-1,6-glucosidic linkage" as used herein refers to the covalent bond that joins alpha-D-glucose molecules to each other through carbons 1 and 6 on adjacent alpha-D-glucose rings. The term "alpha-1,3-glucosidic linkage" as used herein refers to the covalent bond that joins alpha-D-glucose molecules to each other through carbons 1 and 3 on adjacent alpha-D-glucose rings. The term "alpha-1,2-glucosidic linkage" as used herein refers to the covalent bond that joins alpha-D-glucose molecules to each other through carbons 1 and 2 on adjacent alpha-D-glucose rings. The term "alpha-1,4-glucosidic linkage" as used herein refers to the covalent bond that joins alpha-D-glucose molecules to each other through carbons 1 and 4 on adjacent alpha-D-glucose rings. Herein, "alpha-D-glucose" will be referred to as "glucose." All glucosidic linkages disclosed herein are alpha-glucosidic linkages, except where otherwise noted.

"Glucose (glucose monomers) linked at positions 1 and 6" herein refers to a glucose monomer of dextran in which only carbons 1 and 6 of the glucose monomer are involved in respective glucosidic linkages with two adjacent glucose monomers. This definition likewise applies to glucose (i) "linked at positions 1 and 3", and (ii) "linked at positions 1 and 4", taking into account, accordingly, the different carbon positions involved in each respective linkage.

"Glucose (glucose monomers) linked at positions 1, 3 and 6" herein refers to a glucose monomer of dextran in which carbons 1, 3 and 6 of the glucose monomer are involved in respective glucosidic linkages with three adjacent glucose monomers. A glucose linked only at positions 1, 3 and 6 is a branch point. This definition likewise applies to glucose linked at (i) positions 1, 2 and 6, and (ii) positions 1, 4 and 6, but taking into account, accordingly, the different carbon positions involved in each respective linkage.

Glucose positions (glucose carbon positions) 1, 2, 3, 4 and 6 herein are as known in the art (depicted in the following structure):

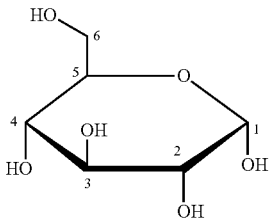

The glycosidic linkage profile of a dextran herein can be determined using any method known in the art. For example, a linkage profile can be determined using methods that use nuclear magnetic resonance (NMR) spectroscopy (e.g., $^{13}$C NMR or $^1$H NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, FL, 2005), which is incorporated herein by reference.

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The "molecular weight" of dextran herein can be represented as number-average molecular weight (Mn) or as weight-average molecular weight (Mw), the units of which are in Daltons or grams/mole. Alternatively, molecular weight can be represented as DPw (weight average degree of polymerization) or DPn (number average degree of polymerization). Various means are known in the art for calculating these molecular weight measurements such as with high-pressure liquid chromatography (HPLC), size exclusion chromatography (SEC), or gel permeation chromatography (GPC).

The term "radius of gyration" (Rg) herein refers to the mean radius of dextran, and is calculated as the root-mean-square distance of a dextran molecule's components (atoms) from the molecule's center of gravity. Rg can be provided in Angstrom or nanometer (nm) units, for example. The "z-average radius of gyration" of dextran herein refers to the Rg of dextran as measured using light scattering (e.g., MALS). Methods for measuring z-average Rg are known and can be used herein, accordingly. For example, z-average Rg can be measured as disclosed in U.S. Pat. No. 7,531,073, U.S. Patent Appl. Publ. Nos. 2010/0003515 and 2009/0046274, Wyatt (*Anal. Chim. Acta* 272:1-40), and Mori and Barth (Size Exclusion Chromatography, Springer-Verlag, Berlin, 1999), all of which are incorporated herein by reference.

The terms "glucosyltransferase enzyme", "gtf enzyme", "gtf enzyme catalyst", "gtf", "glucansucrase" and the like are used interchangeably herein. The activity of a gtf enzyme herein catalyzes the reaction of the substrate sucrose to make the products glucan and fructose. A gtf enzyme that produces a dextran (a type of glucan) can also be referred to as a dextransucrase. Other products (byproducts) of a gtf reaction can include glucose (where glucose is hydrolyzed from the glucosyl-gtf enzyme intermediate complex), and various soluble oligosaccharides (e.g., DP2-DP7) such as leucrose. Wild type forms of glucosyltransferase enzymes generally contain (in the N-terminal to C-terminal direction) a signal peptide, a variable domain, a catalytic domain, and a glucan-binding domain. A gtf herein is classified under the glycoside hydrolase family 70 (GH70) according to the CAZy (Carbohydrate-Active EnZymes) database (Cantarel et al., *Nucleic Acids Res.* 37:D233-238, 2009).

The terms "glucosyltransferase catalytic domain" and "catalytic domain" are used interchangeably herein and refer to the domain of a glucosyltransferase enzyme that provides glucan-producing activity to the glucosyltransferase enzyme.

The terms "gtf reaction", "gtf reaction solution", "glucosyltransferase reaction", "enzymatic reaction", "dextran synthesis reaction", "dextran reaction" and the like are used interchangeably herein and refer to a reaction that is performed by a glucosyltransferase enzyme. A gtf reaction as used herein generally refers to a reaction initially comprising at least one active glucosyltransferase enzyme in a solution comprising sucrose and water, and optionally other components. Other components that can be in a gtf reaction after it has commenced include fructose, glucose, soluble oligosaccharides (e.g., DP2-DP7) such as leucrose, and dextran products. It is in a gtf reaction where the step of contacting water, sucrose and a glucosyltransferase enzyme is performed. The term "under suitable gtf reaction conditions" as used herein, refers to gtf reaction conditions that support conversion of sucrose to dextran via glucosyltransferase enzyme activity. A gtf reaction herein is not naturally occurring.

A "control" gtf reaction as used herein can refer to a reaction using a glucosyltransferase not comprising an amino acid sequence that is at least 90% identical to SEQ ID NO:1, SEQ ID NO:2, SEQ ID NO:5, SEQ ID NO:9, SEQ ID NO:13, or SEQ ID NO:17. All the other features (e.g., sucrose concentration, temperature, pH, time) of a control reaction solution can be the same as the reaction to which it is being compared.

The "percent dry solids" of a gtf reaction refers to the wt % of all the sugars in a gtf reaction. The percent dry solids of a gtf reaction can be calculated, for example, based on the amount of sucrose used to prepare the reaction.

The "yield" of dextran by a gtf reaction herein represents the weight of dextran product expressed as a percentage of the weight of sucrose substrate that is converted in the reaction. For example, if 100 g of sucrose in a reaction solution is converted to products, and 10 g of the products is dextran, the yield of the dextran would be 10%. This yield calculation can be considered as a measure of selectivity of the reaction toward dextran.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

The terms "polynucleotide", "polynucleotide sequence", and "nucleic acid sequence" are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a DNA polynucleotide sequence that expresses an RNA (RNA is transcribed from the DNA polynucleotide sequence) from a coding region (coding sequence), which RNA can be a messenger RNA (encoding a protein) or a non-protein-coding RNA. A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene refers to a gene that is introduced into a host organism by gene transfer. Foreign genes can comprise native genes inserted into a non-native organism, native genes introduced into a new location within the native host, or chimeric genes. Polynucleotide sequences in certain embodiments disclosed herein are heterologous. A "transgene" is a gene that has been introduced into the genome by a transformation procedure. A "codon-optimized" open reading frame has its frequency of codon usage designed to mimic the frequency of preferred codon usage of the host cell.

The term "recombinant" or "heterologous" as used herein refers to an artificial combination of two otherwise separated segments of sequence, e.g., by chemical synthesis or by the manipulation of isolated segments of nucleic acids by genetic engineering techniques. The terms "recombinant", "transgenic", "transformed", "engineered" or "modified for exogenous gene expression" are used interchangeably herein.

A native amino acid sequence or polynucleotide sequence is naturally occurring, whereas a non-native amino acid sequence or polynucleotide sequence does not occur in nature.

"Regulatory sequences" as used herein refer to nucleotide sequences located upstream of a gene's transcription start site (e.g., promoter), 5' untranslated regions, and 3' non-coding regions, and which may influence the transcription, processing or stability, or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein may be heterologous to a coding region herein.

Methods for preparing recombinant constructs/vectors herein can follow standard recombinant DNA and molecular cloning techniques as described by J. Sambrook and D.

Russell (*Molecular Cloning: A Laboratory Manual*, 3rd Edition, Cold Spring Harbor Laboratory Press, Cold Spring Harbor, NY, 2001); T. J. Silhavy et al. (*Experiments with Gene Fusions*, Cold Spring Harbor Laboratory Press, Cold Spring Harbor, NY, 1984); and F. M. Ausubel et al. (*Short Protocols in Molecular Biology*, 5th Ed. Current Protocols, John Wiley and Sons, Inc., NY, 2002).

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining percent complementarity of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW, ClustalV, or Clustal-Omega). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence may have the same function/activity of the disclosed sequence, or at least about 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. Any polypeptide amino acid sequence disclosed herein beginning with a methionine can optionally be considered without this methionine residue (i.e., a polypeptide sequence can be referred to in reference to the position-2 residue to the C-terminal residue of the sequence).

The term "isolated" as used herein refers to any cellular component that has been completely or partially purified from its native source (e.g., an isolated polynucleotide or polypeptide molecule). In some instances, an isolated polynucleotide or polypeptide molecule is part of a greater composition, buffer system or reagent mix. For example, an isolated polynucleotide or polypeptide molecule can be comprised within a cell or organism in a heterologous manner. Another example is an isolated glucosyltransferase enzyme or reaction. "Isolated" herein can also characterize a dextran compound. As such, dextran compounds of the present disclosure are synthetic, man-made compounds, and/or exhibit properties not believed to naturally occur.

An "aqueous composition" herein has a liquid component that comprises at least about 10 wt % water, for example. Examples of aqueous compositions include mixtures, solutions, dispersions (e.g., colloidal dispersions), suspensions and emulsions, for example. Aqueous compositions in certain embodiments comprise dextran that is dissolved in the aqueous composition (i.e., in solution, and typically has viscosity).

As used herein, the term "colloidal dispersion" refers to a heterogeneous system having a dispersed phase and a dispersion medium, i.e., microscopically dispersed insoluble particles are suspended throughout another substance (e.g., an aqueous composition such as water or aqueous solution). An example of a colloidal dispersion herein is a hydrocolloid. All, or a portion of, the particles of a colloidal dispersion such as a hydrocolloid can comprise certain dextran compounds of the present disclosure. The terms "dispersant" and "dispersion agent" are used interchangeably herein to refer to a material that promotes the formation and/or stabilization of a dispersion.

The terms "hydrocolloid" and "hydrogel" are used interchangeably herein. A hydrocolloid refers to a colloid system in which water is the dispersion medium.

The term "aqueous solution" herein refers to a solution in which the solvent comprises water. An aqueous solution can serve as a dispersant in certain aspects herein. Dextran compounds in certain embodiments can be dissolved, dispersed, or mixed within an aqueous solution.

The terms "dispersant", "dispersion agent" and the like are used interchangeably herein to refer to a material that promotes the formation and stabilization of a dispersion of one substance in another. A "dispersion" herein refers to an aqueous composition comprising one or more particles (e.g., any ingredient of a personal care product, pharmaceutical product, food product, household product, or industrial product disclosed herein) that are scattered, or uniformly scattered, throughout the aqueous composition.

The term "viscosity" as used herein refers to the measure of the extent to which a fluid or an aqueous composition such as a hydrocolloid resists a force tending to cause it to flow. Various units of viscosity that can be used herein include centipoise (cPs) and Pascal-second (Pa·s). A centipoise is one one-hundredth of a poise; one poise is equal to 0.100 kg·m$^{-1}$·s$^{-1}$. Thus, the terms "viscosity modifier", "viscosity-modifying agent" and the like as used herein refer to anything that can alter/modify the viscosity of a fluid or aqueous composition.

The term "shear thinning behavior" as used herein refers to a decrease in the viscosity of an aqueous composition as shear rate increases. The term "shear thickening behavior" as used herein refers to an increase in the viscosity of an aqueous composition as shear rate increases. "Shear rate" herein refers to the rate at which a progressive shearing deformation is applied to an aqueous composition. A shearing deformation can be applied rotationally.

The term "contacting" as used herein with respect to methods of increasing the viscosity of an aqueous composition refers to any action that results in bringing together an aqueous composition with a dextran. Contacting can be performed by any means known in the art, such as dissolving, mixing, shaking, or homogenization, for example.

The terms "confectionery" "confection", "sweets", "sweetmeat", "candy" and the like are used interchangeably herein. A confectionary refers to any flavored food product having a sweet taste, the consistency of which may be hard or soft, which is typically consumed by sucking and/or by chewing within the oral cavity. A confectionary can contain sugar or otherwise be sugar-free.

The terms "fabric", "textile", "cloth" and the like are used interchangeably herein to refer to a woven material having a network of natural and/or artificial fibers. Such fibers can be thread or yarn, for example.

A "fabric care composition" herein is any composition suitable for treating fabric in some manner. Examples of such a composition include laundry detergents and fabric softeners.

The terms "heavy duty detergent", "all-purpose detergent" and the like are used interchangeably herein to refer to a detergent useful for regular washing of white and colored textiles at any temperature. The terms "low duty detergent" or "fine fabric detergent" are used interchangeably herein to refer to a detergent useful for the care of delicate fabrics such as viscose, wool, silk, microfiber or other fabric requiring special care. "Special care" can include conditions of using excess water, low agitation, and/or no bleach, for example.

A "detergent composition" herein typically comprises at least one surfactant (detergent compound) and/or at least one builder. A "surfactant" herein refers to a substance that tends to reduce the surface tension of a liquid in which the substance is dissolved. A surfactant may act as a detergent, wetting agent, emulsifier, foaming agent, and/or dispersant, for example.

The terms "anti-redeposition agent", "anti-soil redeposition agent", "anti-greying agent" and the like herein refer to agents that help keep soils from redepositing onto clothing in laundry wash water after these soils have been removed, therefore preventing greying/discoloration of laundry. Anti-redeposition agents can function by helping keep soil dispersed in wash water and/or by blocking attachment of soil onto fabric surfaces.

An "oral care composition" herein is any composition suitable for treating an soft or hard surface in the oral cavity such as dental (teeth) and/or gum surfaces.

The term "adsorption" herein refers to the adhesion of a compound (e.g., dextran herein) to the surface of a material.

The terms "cellulase", "cellulase enzyme" and the like are used interchangeably herein to refer to an enzyme that hydrolyzes beta-1,4-D-glucosidic linkages in cellulose, thereby partially or completely degrading cellulose. Cellulase can alternatively be referred to as "beta-1,4-glucanase", for example, and can have endocellulase activity (EC 3.2.1.4), exocellulase activity (EC 3.2.1.91), or cellobiase activity (EC 3.2.1.21). "Cellulose" refers to an insoluble polysaccharide having a linear chain of beta-1,4-linked D-glucose monomeric units.

There is interest in developing new, high viscosity dextran polymers, which are more amenable to gelling applications. In turn, there is also interest in identifying glucosyltransferase enzymes that can synthesize such dextran polymers.

Embodiments of the present disclosure concern a composition comprising a dextran that comprises:
  (i) about 87-93 wt % glucose linked at positions 1 and 6;
  (ii) about 0.1-1.2 wt % glucose linked at positions 1 and 3;
  (iii) about 0.1-0.7 wt % glucose linked at positions 1 and 4;
  (iv) about 7.7-8.6 wt % glucose linked at positions 1, 3 and 6; and
  (v) about 0.4-1.7 wt % glucose linked at: (a) positions 1, 2 and 6, or (b) positions 1, 4 and 6.

The weight-average molecular weight (Mw) and z-average radius of gyration of such dextran is about 50-200 million Daltons and about 200-280 nm, respectively. Also, such dextran optionally is not a product of a *Leuconostoc mesenteroides* glucosyltransferase enzyme.

An example of this composition is a glucosyltransferase reaction in which a dextran with the above linkage, weight and size profile is synthesized. Significantly, this dextran exhibits high viscosity in aqueous compositions, even at relatively low concentrations of the dextran. It is believed that this high viscosity profile is unique in comparison to viscosity profiles of previously disclosed dextran polymers.

A dextran herein can comprise (i) about 87-93 wt % glucose linked only at positions 1 and 6; (ii) about 0.1-1.2 wt % glucose linked only at positions 1 and 3; (iii) about 0.1-0.7 wt % glucose linked only at positions 1 and 4; (iv) about 7.7-8.6 wt % glucose linked only at positions 1, 3 and 6; and (v) about 0.4-1.7 wt % glucose linked only at: (a) positions 1, 2 and 6, or (b) positions 1, 4 and 6. In certain embodiments, a dextran can comprise (i) about 89.5-90.5 wt % glucose linked only at positions 1 and 6; (ii) about 0.4-0.9 wt % glucose linked only at positions 1 and 3; (iii) about 0.3-0.5 wt % glucose linked only at positions 1 and 4; (iv) about 8.0-8.3 wt % glucose linked only at positions 1, 3 and 6; and (v) about 0.7-1.4 wt % glucose linked only at: (a) positions 1, 2 and 6, or (b) positions 1, 4 and 6.

A dextran in some aspects of the present disclosure can comprise about 87, 87.5, 88, 88.5, 89, 89.5, 90, 90.5, 91, 91.5, 92, 92.5, or 93 wt % glucose linked only at positions 1 and 6. There can be about 87-92.5, 87-92, 87-91.5, 87-91, 87-90.5, 87-90, 87.5-92.5, 87.5-92, 87.5-91.5, 87.5-91, 87.5-90.5, 87.5-90, 88-92.5, 88-92, 88-91.5, 88-91, 88-90.5, 88-90, 88.5-92.5, 88.5-92, 88.5-91.5, 88.5-91, 88.5-90.5, 88.5-90, 89-92.5, 89-92, 89-91.5, 89-91, 89-90.5, 89-90, 89.5-92.5, 89.5-92, 89.5-91.5, 89.5-91, or 89.5-90.5 wt % glucose linked only at positions 1 and 6, in some instances.

A dextran in some aspects can comprise about 0.1, 0.2, 0.3, 0.4, 0.5, 0.6, 0.7, 0.8, 0.9, 1.0, 1.1, or 1.2 wt % glucose linked only at positions 1 and 3. There can be about 0.1-1.2, 0.1-1.0, 0.1-0.8, 0.3-1.2, 0.3-1.0, 0.3-0.8, 0.4-1.2, 0.4-1.0, 0.4-0.8, 0.5-1.2, 0.5-1.0, 0.5-0.8, 0.6-1.2, 0.6-1.0, or 0.6-0.8 wt % glucose linked only at positions 1 and 3, in some instances.

A dextran in some aspects can comprise about 0.1, 0.2, 0.3, 0.4, 0.5, 0.6, or 0.7 wt % glucose linked only at positions 1 and 4. There can be about 0.1-0.7, 0.1-0.6, 0.1-0.5, 0.1-0.4, 0.2-0.7, 0.2-0.6, 0.2-0.5, 0.2-0.4, 0.3-0.7, 0.3-0.6, 0.3-0.5, or 0.3-0.4 wt % glucose linked only at positions 1 and 4, in some instances.

A dextran in some aspects can comprise about 7.7, 7.8, 7.9, 8.0, 8.1, 8.2, 8.3, 8.4, 8.5, or 8.6 wt % glucose linked only at positions 1, 3 and 6. There can be about 7.7-8.6, 7.7-8.5, 7.7-8.4, 7.7-8.3, 7.7-8.2, 7.8-8.6, 7.8-8.5, 7.8-8.4, 7.8-8.3, 7.8-8.2, 7.9-8.6, 7.9-8.5, 7.9-8.4, 7.9-8.3, 7.9-8.2, 8.0-8.6, 8.0-8.5, 8.0-8.4, 8.0-8.3, 8.0-8.2, 8.1-8.6, 8.1-8.5, 8.1-8.1, 8.1-8.3, or 8.1-8.2 wt % glucose linked only at positions 1, 3 and 6, in some instances.

A dextran in some aspects can comprise about 0.4, 0.5, 0.6, 0.7, 0.8, 0.9, 1.0, 1.1, 1.2, 1.3, 1.4, 1.5, 1.6, or 1.7 wt % glucose linked only at (a) positions 1, 2 and 6, or (b) positions 1, 4 and 6. There can be about 0.4-1.7, 0.4-1.6, 0.4-1.5, 0.4-1.4, 0.4-1.3, 0.5-1.7, 0.5-1.6, 0.5-1.5, 0.5-1.4, 0.5-1.3, 0.6-1.7, 0.6-1.6, 0.6-1.5, 0.6-1.4, 0.6-1.3, 0.7-1.7, 0.7-1.6, 0.7-1.5, 0.7-1.4, 0.7-1.3, 0.8-1.7, 0.8-1.6, 0.8-1.5, 0.8-1.4, 0.8-1.3 wt % glucose linked only at (a) positions 1, 2 and 6, or (b) positions 1, 4 and 6, in some instances.

The glucosidic linkage profile of dextran can be determined using dextran produced following any protocol disclosed herein. An example of a suitable linkage determination protocol can be similar to, or the same as, the protocol disclosed in Example 9: For example, an 0768 gtf enzyme reaction that has been deactivated by heating the reaction at about 70-90° C. (e.g., 80° C.) for about 5-30 minutes (e.g., 10 minutes) is placed into dialysis tubing (e.g., made with regenerated cellulose) with an MWCO of 12-14 kDa (e.g., Spectra/Por® 4 Dialysis Tubing, Part No. 132706, Spectrum Laboratories, Inc.). The deactivated reaction is then dialyzed against a large volume of water (e.g., 3-5 L) at about 20-25° C. (room temp) over about 4-10 days (e.g., 7 days); this water can be exchanged every day during the dialysis. The dextran product is then (i) precipitated by mixing the dialyzed deactivated reaction with about 1-2× (1.5×) reaction volume of 100% methanol, (ii) washed at least two times with the same volume of 100% methanol, and (iii) dried at about 40-50° C. (e.g., 45° C.) (optionally under a vacuum). A dissolvable amount of dry dextran is dissolved in dimethyl sulfoxide (DMSO) or DMSO/5% LiCl, after which all free hydroxyl groups are methylated (e.g., by sequential addition of a NaOH/DMSO slurry followed with iodomethane). The methylated dextran is then extracted (e.g., into methylene chloride) and hydrolyzed to monomeric units using aqueous trifluoroacetic acid (TFA) at about 110-125° C. (e.g., 120° C.). The TFA is then evaporated and reductive ring opening is done using sodium borodeuteride. The hydroxyl groups created by hydrolyzing the glycosidic linkages are then acetylated by treating with acetyl chloride and TFA at a temperature of about 40-60° C. (e.g., 50° C.). Next, the derivatizing reagents are evaporated and the resulting methylated/acetylated monomers are reconstituted in acetonitrile; this preparation is then analyzed by GC/MS using an appropriate column (e.g., biscyanopropyl cyanopropylphenyl polysiloxane). The relative positioning of the methyl and acetyl functionalities render species with distinctive retention time indices and mass spectra that can be compared to published databases. In this way, the derivatives of the monomeric units indicate how each monomer was originally linked in the dextran polymer.

It is believed that dextran herein may be a branched structure in which there are long chains (containing mostly or all alpha-1,6-linkages) that iteratively branch from each other (e.g., a long chain can be a branch from another long chain, which in turn can itself be a branch from another long chain, and so on). The branched structure may also comprise short branches from the long chains; these short chains are believed to mostly comprise alpha-1,3 and -1,4 linkages, for example. Branch points in the dextran, whether from a long chain branching from another long chain, or a short chain branching from a long chain, appear to comprise alpha-1,3, -1,4, or -1,2 linkages off of a glucose involved in alpha-1,6 linkage. On average, about 20%, 21%, 22%, 23%, 24%, 25%, 26%, 27%, 28%, 29%, 30%, 15-35%, 15-30%, 15-25%, 15-20%, 20-35%, 20-30%, 20-25%, 25-35%, or 25-30% of all branch points of dextran in some embodiments branch into long chains. Most (>98% or 99%) or all the other branch points branch into short chains.

The long chains of a dextran branching structure can be similar in length in some aspects. By being similar in length, it is meant that the length (DP) of at least 70%, 75%, 80%, 85%, or 90% of all the long chains in a branching structure is within plus/minus 15% (or 10%, 5%) of the mean length of all the long chains of the branching structure. In some aspects, the mean length (average length) of the long chains is about 10-50 DP (i.e., 10-50 glucose monomers). For example, the mean individual length of the long chains can be about 10, 15, 16, 17, 18, 19, 20, 21, 22, 23, 24, 25, 30, 35, 40, 45, 50, 10-50, 10-40, 10-30, 10-25, 10-20, 15-50, 15-40, 15-30, 15-25, 15-20, 20-50, 20-40, 20-30, or 20-25 DP.

Dextran long chains in certain embodiments can comprise substantially alpha-1,6-glucosidic linkages and a small amount (less than 2.0%) of alpha-1,3- and/or alpha-1,4-glucosidic linkages. For example, dextran long chains can comprise about, or at least about, 98%, 98.25%, 98.5%, 98.75%, 99%, 99.25%, 99.5%, 99.75%, or 99.9% alpha-1,6-glucosidic linkages. A dextran long chain in certain embodiments does not comprise alpha-1,4-glucosidic linkages (i.e., such a long chain has mostly alpha-1,6 linkages and a small amount of alpha-1,3 linkages). Conversely, a dextran long chain in some embodiments does not comprise alpha-1,3-glucosidic linkages (i.e., such a long chain has mostly alpha-1,6 linkages and a small amount of alpha-1,4 linkages). Any dextran long chain of the above embodiments may further not comprise alpha-1,2-glucosidic linkages, for example. Still in some aspects, a dextran long chain can comprise 100% alpha-1,6-glucosidic linkages (excepting the linkage used by such long chain to branch from another chain).

Short chains of a dextran molecule in some aspects are one to three glucose monomers in length and comprise less than about 5-10% of all the glucose monomers of the dextran polymer. At least about 90%, 91%, 92%, 93%, 94%, 95%, 96%, 97%, 98%, 99%, or all of, short chains herein are 1-3 glucose monomers in length. The short chains of a dextran molecule can comprise less than about 10%, 9%, 8%, 7%, 6%, 5%, 4%, 3%, 2%, or 1% of all the glucose monomers of the dextran molecule, for example.

Short chains of a dextran molecule in some aspects can comprise alpha-1,2-, alpha-1,3-, and/or alpha-1,4-glucosidic linkages. Short chains, when considered all together (not individually) may comprise (i) all three of these linkages, or (ii) alpha-1,3- and alpha-1,4-glucosidic linkages, for example. It is believed that short chains of a dextran molecule herein can be heterogeneous (i.e., showing some variation in linkage profile) or homogeneous (i.e., sharing similar or same linkage profile) with respect to the other short chains of the dextran.

Dextran in certain embodiments can have an Mw of about, or at least about, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 million (or any integer between 50 and 200 million) (or any range between two of these values). The Mw of dextran can be about 50-200, 60-200, 70-200, 80-200, 90-200, 100-200, 110-200, 120-200, 50-180, 60-180, 70-180, 80-180, 90-180, 100-180, 110-180, 120-180, 50-160, 60-160, 70-160, 80-160, 90-160, 100-160, 110-160, 120-160, 50-140, 60-140, 70-140, 80-140, 90-140, 100-140, 110-140, 120-140, 50-120, 60-120, 70-120, 80-120, 90-120, 100-120, 110-120, 50-110, 60-110, 70-110, 80-110, 90-110, 100-110, 50-100, 60-100, 70-100, 80-100, 90-100, or 95-105 million, for example. Any of these Mw's can be represented in DPw, if desired, by dividing Mw by 162.14.

The z-average radius of gyration of a dextran herein can be about 200-280 nm. For example, the z-average Rg can be about 200, 205, 210, 215, 220, 225, 230, 235, 240, 245, 250, 255, 260, 265, 270, 275, or 280 nm (or any integer between 200-280 nm). As other examples, the z-average Rg can be about 200-280, 200-270, 200-260, 200-250, 200-240, 200-230, 220-280, 220-270, 220-260, 220-250, 220-240, 220-230, 230-280, 230-270, 230-260, 230-250, 230-240, 240-280, 240-270, 240-260, 240-250, 250-280, 250-270, or 250-260 nm.

The Mw and/or z-average Rg of dextran in some aspects can be measured following a protocol similar to, or the same as, the protocol disclosed in Example 9. For example, a Mw and/or z-average Rg herein can be measured by first dissolving dextran produced by an 0768 gtf at 0.4-0.6 mg/mL (e.g., ~0.5 mg/mL) in 0.05-1.0 M (e.g., ~0.075 M) Tris (hydroxymethyl)aminomethane buffer with 150-250 ppm (e.g., ~200 ppm) NaN$_3$. Solvation of dry dextran can be achieved by shaking for 12-18 hours at 45-55° C. (e.g., ~50° C.). The resulting dextran solution can be entered into a suitable flow injection chromatographic apparatus comprising a separation module (e.g., Alliance™ 2695 separation module from Waters Corporation, Milford, MA) coupled with three online detectors: a differential refractometer (e.g., Waters 2414 refractive index detector), a multiangle light scattering (MALS) photometer (e.g., Heleos™-2 18-angle multiangle MALS photometer) equipped with a quasielastic light scattering (QELS) detector (e.g., QELS detector from Wyatt Technologies, Santa Barbara, CA), and a differential capillary viscometer (e.g., ViscoStar™ differential capillary viscometer from Wyatt). Two suitable size-exclusion columns (e.g., AQUAGEL-OH GUARD columns from Agilent Technologies, Santa Clara, CA) can be used to separate the dextran polymer peak from the injection peak, where the mobile phase can be the same as the sample solvent (above), the flow rate can be about 0.2 mL/min, the injection volumes can be about 0.1 mL, and column temperature can be about 30° C. Suitable software can be used for data acquisition (e.g., Empower™ version 3 software from Waters) and for multidetector data reduction (Astra™ version 6 software from Wyatt). MALS data can provide weight-average molecular weight (Mw) and z-average radius of gyration (Rg), and QELS data can provide z-average hydrodynamic radius, for example.

A dextran herein can be a product of a glucosyltransferase enzyme comprising, or consisting of, an amino acid sequence that is 100% identical to, or at least 90%, 91%, 92%, 93%, 94%, 95%, 96%, 97%, 98%, or 99% identical to, SEQ ID NO:1, SEQ ID NO:2, SEQ ID NO:5, SEQ ID NO:9, SEQ ID NO:13, or SEQ ID NO:17 (and have gtf activity). Non-limiting examples of a glucosyltransferase enzyme comprising SEQ ID NO:1 (or a related sequence) include glucosyltransferase enzymes comprising, or consisting of, an amino acid sequence that is 100% identical to, or at least 90%, 91%, 92%, 93%, 94%, 95%, 96%, 97%, 98%, or 99% identical to, SEQ ID NO:2 (and have gtf activity). Production of dextran can be accomplished with a gtf reaction as disclosed herein, for example. Dextran as disclosed in the instant detailed description (e.g., molecular weight, linkage and branching profile) can optionally be characterized as a product of a glucosyltransferase enzyme comprising or consisting of SEQ ID NO:1 or 2 (or a related sequence thereof that is at least 90% identical [above]). In some other embodiments, a glucosyltransferase enzyme comprises or consists of an amino acid sequence that is 100% identical to, or at least 90%, 91%, 92%, 93%, 94%, 95%, 96%, 97%, 98%, or 99% identical to, the secreted portion (i.e., signal peptide removed) of the amino acid sequence encoded by SEQ ID NO:6, 10, 14, or 18.

A glucosyltransferase enzyme herein may be from various microbial sources, such as a bacteria or fungus. Examples of bacterial glucosyltransferase enzymes are those derived from a *Streptococcus* species, *Leuconostoc* species, *Lactobacillus* species, or *Weissella* species. Examples of *Streptococcus* species include *S. sobrinus*, *S. downei*, *S. salivarius*, *S. dentirousetti*, *S. mutans*, *S. oralis*, *S. gallolyticus* and *S. sanguinis*. Examples of *Leuconostoc* species include *L. pseudomesenteroides*, *L. mesenteroides*, *L. amelibiosum*, *L. argentinum*, *L. carnosum*, *L. citreum*, *L. cremoris*, *L. dextranicum* and *L. fructosum*. Examples of *Lactobacillus* species include *L. fermentum*, *L. acidophilus*, *L. delbrueckii*, *L. helveticus*, *L. salivarius*, *L. casei*, *L. curvatus*, *L. plantarum*, *L. sakei*, *L. brevis*, *L. buchneri* and *L. reuteri*. Examples of *Weissella* species include *W. cibaria*, *W. confusa*, *W. halotolerans*, *W. hellenica*, *W. kandleri*, *W. kimchii*, *W. koreensis*, *W. minor*, *W. paramesenteroides*, *W. soli* and *W. thailandensis*. A glucosyltransferase in some aspects is not from *L. mesenteroides*.

Examples of glucosyltransferase enzymes herein can be any of the amino acid sequences disclosed herein and that further include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example.

A glucosyltransferase enzyme used to produce dextran herein is typically in a mature form lacking an N-terminal signal peptide. An expression system for producing a mature glucosyltransferase enzyme herein may employ an enzyme-encoding polynucleotide that further comprises sequence encoding an N-terminal signal peptide to direct extra-cellular secretion. The signal peptide in such embodiments is cleaved from the enzyme during the secretion process. The signal peptide may either be native or heterologous to the glucosyltransferase. An example of a signal peptide useful herein is one from a bacterial (e.g., a *Bacillus* species such as *B. subtilis*) or fungal species. An example of a bacterial signal peptide is an aprE signal peptide, such as one from *Bacillus* (e.g., *B. subtilis*, see Vogtentanz et al., *Protein Expr. Purif.* 55:40-52, which is incorporated herein by reference).

SEQ ID NO:1, SEQ ID NO:5, SEQ ID NO:9, SEQ ID NO:13 and SEQ ID NO:17 are examples of mature glucosyltransferase enzymes that lack an N-terminal signal peptide. Since these and related amino acid sequences do not begin with a methionine residue, it would be understood that an N-terminal start-methionine is preferably added to the sequence (directly or via an intervening heterologous amino acid sequence such as an epitope) if expressing any of these enzymes without using a signal peptide (such as with an expression system where the enzyme is expressed intracellularly and obtained from a cell lysate).

A glucosyltransferase enzyme in certain embodiments can be produced by any means known in the art. For example, a glucosyltransferase enzyme can be produced recombinantly in a heterologous expression system, such as a microbial heterologous expression system. Examples of heterologous expression systems include bacterial (e.g., *E. coli* such as TOP10, MG1655, or BL21 DE3; *Bacillus* sp. such as *B. subtilis*) and eukaryotic (e.g., yeasts such as *Pichia* sp. and *Saccharomyces* sp.) expression systems.

A glucosyltransferase enzyme disclosed herein may be used in any purification state (e.g., pure or non-pure). For example, the glucosyltransferase enzyme may be purified and/or isolated prior to its use. Examples of glucosyltransferase enzymes that are non-pure include those in the form of a cell lysate. A cell lysate or extract may be prepared from a bacteria (e.g., *E. coli*) used to heterologously express the enzyme. For example, the bacteria may be subjected to disruption using a French pressure cell. In alternative embodiments, bacteria may be homogenized with a homogenizer (e.g., APV, Rannie, Gaulin). A glucosyltransferase enzyme is typically soluble in these types of preparations. A bacterial cell lysate, extract, or homogenate herein may be used at about 0.15-0.3% (v/v) in a reaction for producing dextran from sucrose.

A heterologous gene expression system for expressing a glucosyltransferase enzyme herein can be designed for protein secretion, for example. A glucosyltransferase enzyme typically comprises a signal peptide in such embodiments. A glucosyltransferase enzyme in some embodiments does not occur in nature, for example, an enzyme herein is not believed to be one that is naturally secreted (i.e., mature form) from a microbe (from which the glucosyltransferase enzyme herein could possibly have been derived).

The activity of a glucosyltransferase enzyme herein can be determined using any method known in the art. For example, glucosyltransferase enzyme activity can be determined by measuring the production of reducing sugars (fructose and glucose) in a reaction containing sucrose (~50 g/L), dextran T10 (~1 mg/mL) and potassium phosphate buffer (~pH 6.5, 50 mM), where the solution is held at ~22-25° C. for ~24-30 hours. The reducing sugars can be measured by adding 0.01 mL of the reaction to a mixture containing ~1 N NaOH and ~0.1% triphenyltetrazolium chloride and then monitoring the increase in absorbance at $OD_{480\ nm}$ for ~five minutes. Also for instance, a unit of an enzyme such as gtf 0768 (comprising SEQ ID NO:1) herein can be defined as the amount of enzyme required to consume 1 g of sucrose in 1 hour at 26° C., pH 6.5, and with 100 g/L of sucrose.

A dextran as presently disclosed can be a product of a glucosyltransferase as comprised in a glucosyltransferase reaction.

The temperature of a glucosyltransferase reaction herein can be controlled, if desired. In certain embodiments, the temperature is between about 5° C. to about 50° C. The temperature in certain other embodiments is between about 20° C. to about 40° C. Alternatively, the temperature may be about 20, 21, 22, 23, 24, 25, 26, 27, 28, 29, 30, 31, 32, 33, 34, 35, 36, 37, 38, 39, or 40° C. The temperature of a glucosyltransferase reaction herein may be maintained using various means known in the art. For example, the temperature can be maintained by placing the vessel containing the reaction in an air or water bath incubator set at the desired temperature.

The initial concentration of sucrose in a glucosyltransferase reaction herein can be about 20 g/L to 900 g/L, 20 g/L to 400 g/L, 75 g/L to 175 g/L, or 50 g/L to 150 g/L. The initial concentration of sucrose can be about 20, 30, 40, 50, 60, 70, 80, 90, 100, 110, 120, 130, 140, 150, 160, 200, 300, 400, 500, 600, 700, 800, 900, 50-150, 75-125, 90-110, 50-500, 100-500, 200-500, 300-500, 400-500, 50-400, 100-400, 200-400, 300-400, 50-300, 100-300, 200-300, 50-200, 100-200, or 50-100 g/L (or any integer between 20 and 900 g/L), for example. "Initial concentration of sucrose" refers to the sucrose concentration in a gtf reaction just after all the reaction components have been added (at least water, sucrose, glucosyltransferase enzyme).

Sucrose used in a glucosyltransferase reaction herein can be highly pure (99.5%) or be of any other purity or grade. For example, sucrose can have a purity of at least 99.0%, or can be reagent grade sucrose. As another example, incompletely refined sucrose can be used. Incompletely refined sucrose herein refers to sucrose that has not been processed to white refined sucrose. Thus, incompletely refined sucrose can be completely unrefined or partially refined. Examples of unrefined sucrose are "raw sucrose" ("raw sugar") and solutions thereof. Examples of partially refined sucrose have not gone through one, two, three, or more crystallization steps. The ICUMSA (International Commission for Uniform Methods of Sugar Analysis) of incompletely refined sucrose herein can be greater than 150, for example. Sucrose herein may be derived from any renewable sugar source such as sugar cane, sugar beets, cassava, sweet sorghum, or corn. Suitable forms of sucrose useful herein are crystalline form or non-crystalline form (e.g., syrup, cane juice, beet juice), for example. Additional suitable forms of incompletely refined sucrose are disclosed in U.S. Appl. Publ. No. 2015/0275256, which is incorporated herein by reference.

Methods of determining ICUMSA values for sucrose are well known in the art and disclosed by the International Commission for Uniform Methods of Sugar Analysis in *ICUMSA Methods of Sugar Analysis: Official and Tentative Methods Recommended by the International Commission for Uniform Methods of Sugar Analysis (ICUMSA)* (Ed. H. C. S. de Whalley, Elsevier Pub. Co., 1964), for example, which is incorporated herein by reference. ICUMSA can be measured, for example, by ICUMSA Method GS1/3-7 as described by R. J. McCowage, R. M. Urquhart and M. L. Burge (*Determination of the Solution Colour of Raw Sugars, Brown Sugars and Coloured Syrups at pH 7.0—Official*, Verlag Dr Albert Bartens, 2011 revision), which is incorporated herein by reference.

The pH of a glucosyltransferase reaction in certain embodiments can be between about 4.0 to about 8.0. Alternatively, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. Buffer concentration in a gtf reaction can be from 0 mM to about 100 mM, or about 10, 20, or 50 mM, for example.

A glucosyltransferase reaction can be contained within any vessel suitable for applying one or more of the reaction conditions disclosed herein. For example, a glucosyltransferase reaction herein may be in a stainless steel, plastic, or glass vessel or container of a size suitable to contain a particular reaction. Such a vessel can optionally be equipped with a stirring device.

A glucosyltransferase reaction herein can optionally be agitated via stirring or orbital shaking, for example. Such agitation can be at about 50, 60, 70, 80, 90, 100, 110, 120, 130, 140, 150, 50-150, 60-140, 70-130, 80-120, or 90-110 rpm, for example.

The concentration of glucosyltransferase enzyme in a reaction can be at least about 15, 20, 25, 30, 35, or 40 U/L, for example. In some embodiments, 15-35, 15-30, 15-25, 20-35, 20-30, 20-25, 25-35, 25-30, or 30-35 U/L of glucosyltransferase can be used.

A glucosyltransferase reaction herein can take about 2, 3, 4, 5, 6, 7, 8, 9, 10, 12, 18, 24, 30, 36, 48, 60, 72, 84, 96, 18-30, 20-28, or 22-26 hours to complete. Reaction time may depend, for example, on certain parameters such as the amount of sucrose and glucosyltransferase enzyme used in the reaction.

All the features herein defining a glucosyltransferase reaction can be combined, accordingly. Simply as an example, a reaction using an 0768 glucosyltransferase (comprising SEQ ID NO:1 or related sequence thereof) can initially contain 90-110 g/L (e.g., ~100 g/L) sucrose, 10-30 mM (e.g., ~20 mM) sodium phosphate buffer at pH 6.0-7.0 (e.g., ~pH 6.5), and 20-30 U/L (e.g., ~25 U/L) enzyme. Such a reaction can be held for about 20-28 hours (e.g., ~24 hours) with 50-150 rpm (e.g., ~100 rpm) shaking at 24-28° C. (e.g., ~26° C.).

In some embodiments, a glucosyltransferase reaction comprising a gtf 0768 enzyme (SEQ ID NO:1 or related sequences) and any amount of sucrose disclosed herein can be complete (e.g., 95% or more initially provided sucrose depleted) in less than about 24, 22, 20, 18, or 16 hours after initiating the reaction. Depletion of sucrose in such a reaction can be about, or at least about, 3, 4, 5, 6, 7, 8, 9, or 10 times faster than a same or similar reaction, but which comprises a *Leuconostoc mesenteroides* dextran sucrase instead of a gtf 0768 enzyme, for example.

A composition comprising a dextran herein can be non-aqueous (e.g., a dry composition). Examples of such embodiments include powders, granules, microcapsules, flakes, or any other form of particulate matter. Other examples include larger compositions such as pellets, bars, kernels, beads, tablets, sticks, or other agglomerates. A non-aqueous or dry composition herein typically has less than 3, 2, 1, 0.5, or 0.1 wt % water comprised therein. The amount of dextran herein in a non-aqueous or dry composition can be about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, or 99.9 wt %, for example. A non-aqueous composition herein can be in the form of a household product, personal care product, pharmaceutical product, industrial product, or food product, for example.

In certain embodiments of the present disclosure, a composition comprising a dextran can be an aqueous composition having a viscosity of about, or at least about, 25 cPs. Alternatively, an aqueous composition herein can have a viscosity of about, or at least about, 25, 50, 75, 100, 250, 500, 750, 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, or 50000 cPs (or any integer between 25 and 50000 cPs), for example. Examples of aqueous compositions include hydrocolloids and aqueous solutions.

Viscosity can be measured with an aqueous composition herein at any temperature between about 3° C. to about 110° C. (or any integer between 3 and 110° C.). Alternatively, viscosity can be measured at a temperature between about 4° C. to 30° C., or about 20° C. to 25° C., for example. Viscosity can be measured at atmospheric pressure (about 760 torr) or any other higher or lower pressure.

The viscosity of an aqueous composition disclosed herein can be measured using a viscometer or rheometer, or using any other means known in the art. It would be understood by those skilled in the art that a viscometer or rheometer can be used to measure the viscosity of aqueous compositions herein that exhibits rheological behavior (i.e., having viscosities that vary with flow conditions). The viscosity of such embodiments can be measured at a rotational shear rate of about 0.1 to 1000 rpm (revolutions per minute), for example. Alternatively, viscosity can be measured at a rotational shear rate of about 10, 60, 150, 250, or 600 rpm.

In certain embodiments, viscosity can be measured with an aqueous composition in which the constituent dextran was synthesized. For example, viscosity can be measured for a gtf reaction herein that is at or near completion. Viscosity can thus be measured with an aqueous composition in which the constituent dextran is not purified (e.g., other components in the composition, aside from water, are present at greater than 1, 5, or 10 wt %); such a composition can contain one or more salts, buffers, proteins (e.g., gtf enzymes), sugars (e.g., fructose, glucose, leucrose, oligosaccharides).

The pH of an aqueous composition disclosed herein can be between about 2.0 to about 12.0, for example. Alternatively, pH can be about 2.0, 3.0, 4.0, 5.0, 6.0, 7.0, 8.0, 9.0, 10.0, 11.0, 12.0; or between 5.0 to about 12.0; or between about 4.0 and 8.0; or between about 5.0 and 8.0, for example.

An aqueous composition herein such as a hydrocolloid or aqueous solution can comprise a solvent having about, or at least about, 10 wt % water. In other embodiments, a solvent is about, or at least about, 20, 30, 40, 50, 60, 70, 80, 90, or 100 wt % water (or any integer value between 10 and 100 wt %), for example.

A dextran herein can be present in an aqueous composition at a wt % of about, or at least about, 0.01, 0.05, 0.1, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 wt %, for example. Example 8 below demonstrates that dextran in certain aspects provides high viscosity to aqueous solutions at relatively low concentrations of the dextran. Thus, certain embodiments of the present disclosure are drawn to aqueous compositions with less than about 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0.5 wt % dextran herein.

An aqueous composition herein can comprise other components in addition to dextran. For example, an aqueous composition can comprise one or more salts such as a sodium salt (e.g., NaCl, Na$_2$SO$_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitrite, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in an aqueous composition, for example. A salt can be present in an aqueous composition herein at a wt % of about 0.01 to about 10.00 (or any hundredth increment between 0.01 and 10.00), for example.

A composition herein may optionally contain one or more active enzymes. Non-limiting examples of suitable enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, arabinofuranosidases, phytases, isomerases, transferases and amylases. If an enzyme(s) is included, it may be comprised in a composition herein at about 0.0001-0.1 wt % (e.g., 0.01-0.03 wt %) active enzyme (e.g., calculated as pure enzyme protein), for example.

A cellulase herein can have endocellulase activity (EC 3.2.1.4), exocellulase activity (EC 3.2.1.91), or cellobiase activity (EC 3.2.1.21). A cellulase herein is an "active cellulase" having activity under suitable conditions for maintaining cellulase activity; it is within the skill of the art to determine such suitable conditions.

A cellulase herein may be derived from any microbial source, such as a bacteria or fungus. Chemically-modified cellulases or protein-engineered mutant cellulases are included. Suitable cellulases include, but are not limited to, cellulases from the genera *Bacillus, Pseudomonas, Streptomyces, Trichoderma, Humicola, Fusarium, Thielavia* and *Acremonium*. As other examples, a cellulase may be derived from *Humicola insolens, Myceliophthora thermophila* or *Fusarium oxysporum*; these and other cellulases are disclosed in U.S. Pat. Nos. 4,435,307, 5,648,263, 5,691,178, 5,776,757 and 7,604,974, which are all incorporated herein by reference. Exemplary *Trichoderma reesei* cellulases are disclosed in U.S. Pat. Nos. 4,689,297, 5,814,501, 5,324,649, and International Patent Appl. Publ. Nos. WO92/06221 and WO92/06165, all of which are incorporated herein by reference. Exemplary *Bacillus* cellulases are disclosed in U.S. Pat. No. 6,562,612, which is incorporated herein by reference. A cellulase, such as any of the foregoing, preferably is in a mature form lacking an N-terminal signal peptide. Commercially available cellulases useful herein include CELLUZYME® and CAREZYME® (Novozymes A/S); CLAZINASE® and PURADAX® HA (DuPont Industrial Biosciences), and KAC-500(B)® (Kao Corporation).

Alternatively, a cellulase herein may be produced by any means known in the art, such as described in U.S. Pat. Nos. 4,435,307, 5,776,757 and 7,604,974, which are incorporated herein by reference. For example, a cellulase may be produced recombinantly in a heterologous expression system, such as a microbial or fungal heterologous expression system. Examples of heterologous expression systems include bacterial (e.g., *E. coli, Bacillus* sp.) and eukaryotic systems. Eukaryotic systems can employ yeast (e.g., *Pichia* sp., *Saccharomyces* sp.) or fungal (e.g., *Trichoderma* sp. such as *T. reesei, Aspergillus* species such as *A. niger*) expression systems, for example.

One or more cellulases can be directly added as an ingredient when preparing a composition disclosed herein. Alternatively, one or more cellulases can be indirectly (inadvertently) provided in the disclosed composition. For example, cellulase can be provided in a composition herein by virtue of being present in a non-cellulase enzyme preparation used for preparing a composition. Cellulase in compositions in which cellulase is indirectly provided thereto can be present at about 0.1-10 ppb (e.g., less than 1 ppm), for example. A contemplated benefit of a composition herein, by virtue of employing a dextran compound, is that non-cellulase enzyme preparations that might have background cellulase activity can be used without concern that the desired effects of the dextran will be negated by the background cellulase activity.

A cellulase in certain embodiments can be thermostable. Cellulase thermostability refers to the ability of the enzyme to retain activity after exposure to an elevated temperature (e.g. about 60-70° C.) for a period of time (e.g., about 30-60 minutes). The thermostability of a cellulase can be measured by its half-life (t½) given in minutes, hours, or days, during which time period half the cellulase activity is lost under defined conditions.

A cellulase in certain embodiments can be stable to a wide range of pH values (e.g. neutral or alkaline pH such as pH of ~7.0 to ~11.0). Such enzymes can remain stable for a predetermined period of time (e.g., at least about 15 min., 30 min., or 1 hour) under such pH conditions.

At least one, two, or more cellulases may be included in the composition. The total amount of cellulase in a composition herein typically is an amount that is suitable for the purpose of using cellulase in the composition (an "effective amount"). For example, an effective amount of cellulase in a composition intended for improving the feel and/or appearance of a cellulose-containing fabric is an amount that produces measurable improvements in the feel of the fabric (e.g., improving fabric smoothness and/or appearance, removing pills and fibrils which tend to reduce fabric appearance sharpness). As another example, an effective amount of cellulase in a fabric stonewashing composition herein is that amount which will provide the desired effect (e.g., to produce a worn and faded look in seams and on fabric panels). The amount of cellulase in a composition herein can also depend on the process parameters in which the composition is employed (e.g., equipment, temperature, time, and the like) and cellulase activity, for example. The effective concentration of cellulase in an aqueous composition in which a fabric is treated can be readily determined by a skilled artisan. In fabric care processes, cellulase can be present in an aqueous composition (e.g., wash liquor) in which a fabric is treated in a concentration that is minimally about 0.01-0.1 ppm total cellulase protein, or about 0.1-10 ppb total cellulase protein (e.g., less than 1 ppm), to maximally about 100, 200, 500, 1000, 2000, 3000, 4000, or 5000 ppm total cellulase protein, for example.

Dextran polymers provided herein are believed to be mostly or completely stable (resistant) to being degraded by cellulase. For example, the percent degradation of a dextran herein by one or more cellulases is believed to be less than 10%, 9%, 8%, 7%, 6%, 5%, 4%, 3%, 2%, or 1%, or is 0%. Such percent degradation can be determined, for example, by comparing the molecular weight of dextran polymer before and after treatment with a cellulase for a period of time (e.g., ~24 hours).

Aqueous compositions in certain embodiments are believed to have shear thinning behavior or shear thickening behavior. Shear thinning behavior is observed as a decrease in viscosity of the aqueous composition as shear rate increases, whereas shear thickening behavior is observed as an increase in viscosity of the aqueous composition as shear rate increases. Modification of the shear thinning behavior or shear thickening behavior of an aqueous composition herein can be due to the admixture of a dextran to the aqueous composition. Thus, one or more dextran compounds of the present disclosure can be added to an aqueous composition to modify its rheological profile (i.e., the flow properties of an aqueous liquid, solution, or mixture are modified). Also, one or more dextran compounds can be added to an aqueous composition to modify its viscosity.

The rheological properties of aqueous compositions herein can be observed by measuring viscosity over an increasing rotational shear rate (e.g., from about 0.1 rpm to about 1000 rpm). For example, shear thinning behavior of an aqueous composition disclosed herein can be observed as a decrease in viscosity (cPs) by about, or at least about, 5%, 10%, 15%, 20%, 25%, 30%, 35%, 40%, 45%, 50%, 55%, 60%, 65%, 70%, 75%, 80%, 85%, 90%, or 95% (or any integer between 5% and 95%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm. As another example, shear thickening behavior of an aqueous composition disclosed herein can be observed as an increase in viscosity (cPs) by about, or at least about, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% (or any integer between 5% and 200%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm.

An aqueous composition disclosed herein can be in the form of, and/or comprised in, a food product, personal care product, pharmaceutical product, household product, or industrial product, such as any of those products described below. Dextran compounds herein can be used as thickening agents in each of these products. Such a thickening agent may be used in conjunction with one or more other types of thickening agents if desired, such as those disclosed in U.S. Pat. No. 8,541,041, the disclosure of which is incorporated herein by reference in its entirety.

Dextran compounds disclosed herein are believed to be useful for providing one or more of the following physical properties to a personal care product, pharmaceutical product, household product, industrial product, or food product: thickening, freeze/thaw stability, lubricity, moisture retention and release, texture, consistency, shape retention, emulsification, binding, suspension, dispersion, gelation, reduced mineral hardness, for example. Examples of a concentration or amount of a dextran in a product can be any of the weight percentages provided herein, for example.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient, if desired. An active ingredient is generally recognized as an ingredient that causes an intended pharmacological effect.

In certain embodiments, a skin care product can be applied to skin for addressing skin damage related to a lack of moisture. A skin care product may also be used to address the visual appearance of skin (e.g., reduce the appearance of flaky, cracked, and/or red skin) and/or the tactile feel of the skin (e.g., reduce roughness and/or dryness of the skin while improved the softness and subtleness of the skin). A skin care product typically may include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil.

A personal care product herein can also be in the form of makeup, lipstick, mascara, rouge, foundation, blush, eyeliner, lip liner, lip gloss, other cosmetics, sunscreen, sun block, nail polish, nail conditioner, bath gel, shower gel, body wash, face wash, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, pre-shaving product, aftershaving product, cleanser, skin gel, rinse, dentifrice composition, toothpaste, or mouthwash, for example. An example of a personal care product (e.g., a cleanser, soap, scrub, cosmetic) comprises a carrier or exfoliation agent (e.g., jojoba beads [jojoba ester beads]) (e.g., about 1-10, 3-7, 4-6, or 5 wt %); such an agent may optionally be dispersed within the product.

A personal care product in some aspects can be a hair care product. Examples of hair care products herein include shampoo, hair conditioner (leave-in or rinse-out), cream rinse, hair dye, hair coloring product, hair shine product, hair serum, hair anti-frizz product, hair split-end repair product, mousse, hair spray, and styling gel. A hair care product can be in the form of a liquid, paste, gel, solid, or powder in some embodiments. A hair care product as presently disclosed typically comprises one or more of the following ingredients, which are generally used to formulate hair care products: anionic surfactants such as polyoxyethylenelauryl ether sodium sulfate; cationic surfactants such as stearyltrimethylammonium chloride and/or distearyltrimethylammonium chloride; nonionic surfactants such as glyceryl monostearate, sorbitan monopalmitate and/or polyoxyethylenecetyl ether; wetting agents such as propylene glycol, 1,3-butylene glycol, glycerin, sorbitol, pyroglutamic acid salts, amino acids and/or trimethylglycine; hydrocarbons such as liquid paraffins, petrolatum, solid paraffins, squalane and/or olefin oligomers; higher alcohols such as stearyl alcohol and/or cetyl alcohol; superfatting agents; antidandruff agents; disinfectants; anti-inflammatory agents; crude drugs; water-soluble polymers such as methyl cellulose, hydroxycellulose and/or partially deacetylated chitin (in addition to one or more dextrans as disclosed herein); antiseptics such as paraben; ultra-violet light absorbers; pearling agents; pH adjustors; perfumes; and pigments.

A pharmaceutical product herein can be in the form of an emulsion, liquid, elixir, gel, suspension, solution, cream, or ointment, for example. Also, a pharmaceutical product herein can be in the form of any of the personal care products disclosed herein, such as an antibacterial or antifungal composition. A pharmaceutical product can further comprise one or more pharmaceutically acceptable carriers, diluents, and/or pharmaceutically acceptable salts. A dextran compound disclosed herein can also be used in capsules, encapsulants, tablet coatings, and as an excipients for medicaments and drugs.

Non-limiting examples of food products herein include vegetable, meat, and soy patties; reformed seafood; reformed cheese sticks; cream soups; gravies and sauces; salad dressing; mayonnaise; onion rings; jams, jellies, and syrups; pie filling; potato products such as French fries and extruded fries; batters for fried foods, pancakes/waffles and cakes; pet foods; confectioneries (candy); beverages; frozen desserts; ice cream; cultured dairy products such as cottage cheese, yogurt, cheeses, and sour creams; cake icing and glazes; whipped topping; leavened and unleavened baked goods; and the like.

In certain embodiments, dextran herein can be comprised in a foodstuff or any other ingestible material (e.g., enteral pharmaceutical preparation) in an amount that provides the desired degree of thickening and/or dispersion. For example, the concentration or amount of dextran in a product can be about 0.1-3 wt %, 0.1-4 wt %, 0.1-5 wt %, or 0.1-10 wt %.

A household and/or industrial product herein can be in the form of drywall tape-joint compounds; mortars; grouts; cement plasters; spray plasters; cement stucco; adhesives; pastes; wall/ceiling texturizers; binders and processing aids for tape casting, extrusion forming, injection molding and ceramics; spray adherents and suspending/dispersing aids for pesticides, herbicides, and fertilizers; fabric care products such as fabric softeners and laundry detergents; hard surface cleaners; air fresheners; polymer emulsions; gels such as water-based gels; surfactant solutions; paints such as water-based paints; protective coatings; adhesives; sealants and caulks; inks such as water-based ink; metal-working fluids; or emulsion-based metal cleaning fluids used in electroplating, phosphatizing, galvanizing and/or general metal cleaning operations, for example.

A dextran compound disclosed herein can be comprised in a personal care product, pharmaceutical product, household product, or industrial product in an amount that provides a desired degree of thickening and/or dispersion, for example. Examples of a concentration or amount of a dextran compound in a product can be any of the weight percentages provided above, for example.

An aqueous composition in some aspects can comprise about 0.5-2.0 wt % dextran herein (e.g., ~1.0 wt %), about 15-25 wt % (e.g., ~20 wt %) of moisturizer such as oil (e.g., mineral oil), about 4-6 wt % (~5 wt %) surfactant/emulsifier (e.g., one or both of sorbitan monooleate or polysorbate 80, such as ~2.6 wt % sorbitan monooleate and ~2.4 wt % polysorbate 80), optionally 0.25-1.0 wt % (e.g., 0.5 wt %) preservative (e.g., preservative comprising one or more of propylene glycol, diazolidinyl urea, methylparaben, or propylparaben [e.g., Germaben® II]), and optionally one or more other ingredients. Such compositions can be in the form of an emulsion, for example. In these and some other related aspects, dextran as presently disclosed can be used as a substitute for compounds (e.g., xanthan gum, crosslinked polyacrylic acid polymers such as Carbopol® Ultrez 10) typically used to provide viscosity to certain consumer products such as personal care (e.g., lotion), food, and/or pharmaceutical products. Still in some aspects the sensory experience rating of an aqueous composition (e.g., personal care item such as lotion), as measured by ASTM E1490-3 ("Standard Practice for Descriptive Skinfeel Analysis of Creams and Lotions", ASTM International, West Conshohocken, PA, 2003, DOI: 10.1520/E1490-03, incorporated herein by reference), can be less than about 8, 7, or 6, where each of rub-out sliminess, afterfeel stickiness, pick-up stringiness and pick-up stickiness are measured in the evaluation.

A food product herein can be in the form of a confectionery, for example. A confectionary herein can contain one or more sugars (e.g., sucrose, fructose, dextrose) for sweetening, or otherwise be sugar-free.

Examples of confectioneries herein include boiled sugars (hard boiled candies [i.e., hard candy]), dragees, jelly candies, gums, licorice, chews, caramels, toffee, fudge, chewing gums, bubble gums, nougat, chewy pastes, halawa, tablets, lozenges, icing, frosting, pudding, and gels (e.g., fruit gels, gelatin dessert). Other examples of confectioneries include aerated confectioneries such as marshmallows, and baked confectioneries.

A confectionery herein can optionally be prepared with chocolate, in any form (e.g., bars, candies, bonbons, truffles, lentils). A confectionary can be coated with chocolate, sugar-coated, candied, glazed, and/or film-coated, for example. Film-coating processes typically comprise applying to the surface of a confectionery a film-forming liquid composition which becomes, after drying, a protective film. This film-coating serves, for example, to protect the active principles contained in the confectionery; to protect the confectionery itself from moisture, shocks, and/or friability; and/or to confer the confectionery attractive visual properties (e.g., shine, uniform color, smooth surface).

In certain embodiments, a confectionery can be filled with a filling that is liquid, pasty, solid, or powdered. Dextran herein can be comprised in such a filling, in which case dextran is optionally also included in the confectionery component being filled.

A confectionery herein is optionally sugar-free, comprising no sugar and typically instead having one or more artificial and/or non-sugar sweeteners (optionally non-caloric) (e.g., aspartame, saccharin, STEVIA, SUCRALOSE). A sugar-free confectionery in certain embodiments can comprise one or more polyols (e.g., erythritol, glycerol, lactitol, mannitol, maltitol, xylitol), soluble fibers, and/or proteins in place of sugar.

A food product herein can be in the form of a pet food, for example. A pet food herein can be a food for a domesticated animal such as a dog or cat (or any other companion animal), for example. A pet food in certain embodiments provides to a domestic animal one or more of the following: necessary dietary requirements, treats (e.g., dog biscuits), food supplements. Examples of pet food include dry pet food (e.g., kernels, kibbles), semi-moist compositions, wet pet food (e.g., canned pet food), or any combination thereof. Wet pet food typically has a moisture content over 65%. Semi-moist pet food typically has a moisture content of 20-65% and can include humectants such as propylene glycol, potassium sorbate, and ingredients that prevent microbial growth (bacteria and mold). Dry pet food typically has a moisture content less than 20% and its processing usually includes extruding, drying and/or baking. A pet food can optionally be in the form of a gravy, yogurt, powder, suspension, chew, or treat (e.g., biscuits); all these compositions can also be used as pet food supplements, if desired. Pet treats can be semi-moist chewable treats; dry treats; chewable bones; baked, extruded or stamped treats; or confection treats, for example. Examples of pet food compositions/formulations in which a dextran herein can be added include those disclosed in U.S. Patent Appl. Publ. Nos. 2013/0280352 and 2010/0159103, and U.S. Pat. No. 6,977,084, which are all incorporated herein by reference.

Compositions disclosed herein can be in the form of a fabric care composition. A fabric care composition herein can be used for hand wash, machine wash and/or other purposes such as soaking and/or pretreatment of fabrics, for example. A fabric care composition may take the form of, for example, a laundry detergent; fabric conditioner; any wash-, rinse-, or dryer-added product; unit dose or spray. Fabric care compositions in a liquid form may be in the form of an aqueous composition as disclosed herein. In other aspects, a fabric care composition can be in a dry form such as a granular detergent or dryer-added fabric softener sheet. Other non-limiting examples of fabric care compositions herein include: granular or powder-form all-purpose or heavy-duty washing agents; liquid, gel or paste-form all-purpose or heavy-duty washing agents; liquid or dry fine-fabric (e.g. delicates) detergents; cleaning auxiliaries such as bleach additives, "stain-stick", or pre-treatments; substrate-laden products such as dry and wetted wipes, pads, or sponges; sprays and mists.

A detergent composition herein may be in any useful form, e.g., as powders, granules, pastes, bars, unit dose, or liquid. A liquid detergent may be aqueous, typically containing up to about 70 wt % of water and 0 wt % to about 30 wt % of organic solvent. It may also be in the form of a compact gel type containing only about 30 wt % water.

A detergent composition herein typically comprises one or more surfactants, wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the detergent composition. A detergent will usually contain 0 wt % to about 50 wt % of an anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. In addition, a detergent composition may optionally contain 0 wt % to about 40 wt % of a nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO92/06154, which is incorporated herein by reference).

A detergent composition herein typically comprises one or more detergent builders or builder systems. One or more oxidized poly alpha-1,3-glucan compounds can be included as a builder, for example. In some aspects, oxidized poly alpha-1,3-glucan can be included as a co-builder, in which it is used together with one or more additional builders such as any disclosed herein. Oxidized poly alpha-1,3-glucan compounds for use herein are disclosed in U.S. Patent Appl. Publ. No. 2015/0259439. In some embodiments incorporating at least one builder, the cleaning compositions comprise at least about 1%, from about 3% to about 60%, or even from about 5% to about 40%, builder by weight of the composition. Builders (in addition to oxidized poly alpha-1,3-glucan) include, but are not limited to, alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present disclosure. Additional examples of a detergent builder or complexing agent include zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst).

In some embodiments, builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present disclosure, including those known in the art (See, e.g., EP2100949).

In some embodiments, suitable builders can include phosphate builders and non-phosphate builders. In some embodiments, a builder is a phosphate builder. In some embodiments, a builder is a non-phosphate builder. A builder can be used in a level of from 0.1% to 80%, or from 5% to 60%, or from 10% to 50%, by weight of the composition. In some embodiments, the product comprises a mixture of phosphate and non-phosphate builders. Suitable phosphate builders include mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include ammonium and/or alkali metal salts, i.e., lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

A detergent composition herein can comprise at least one chelating agent. Suitable chelating agents include, but are not limited to, copper, iron and/or manganese chelating agents and mixtures thereof. In embodiments in which at least one chelating agent is used, the composition comprises from about 0.1% to about 15%, or even from about 3.0% to about 10%, chelating agent by weight of the composition.

A detergent composition herein can comprise at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

A detergent composition herein can comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Additional dye transfer inhibiting agents include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethyl ethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof, which can be used alone or in combination with any of the above. In embodiments in which at least one dye transfer inhibiting agent is used, a composition herein may comprise from about 0.0001% to about 10%, from about 0.01% to about 5%, or even from about 0.1% to about 3%, by weight of the composition.

A detergent composition herein can comprise silicates. In some of these embodiments, sodium silicates (e.g., sodium disilicate, sodium metasilicate, and/or crystalline phyllosilicates) find use. In some embodiments, silicates are present at a level of from about 1% to about 20% by weight of the composition. In some embodiments, silicates are present at a level of from about 5% to about 15% by weight of the composition.

A detergent composition herein can comprise dispersants. Suitable water-soluble organic materials include, but are not limited to the homo- or co-polymeric acids or their salts, in which the polycarboxylic acid comprises at least two carboxyl radicals separated from each other by not more than two carbon atoms.

A detergent composition herein may additionally comprise one or more enzymes. Examples of enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase, phenoloxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, alpha-amylases, beta-amylases, galactosidases, galactanases, catalases, carageenases, hyaluronidases, keratinases, lactases, ligninases, peroxidases, phosphatases, polygalacturonases, pullulanases, rhamnogalactouronases, tannases, transglutaminases, xyloglucanases, xylosidases, metalloproteases, arabinofuranosidases, phytases, isomerases, transferases and/or amylases in any combination.

Any cellulase disclosed above is contemplated for use in the disclosed detergent compositions. Suitable cellulases include, but are not limited to *Humicola insolens* cellulases (See e.g., U.S. Pat. No. 4,435,307). Exemplary cellulases contemplated for use herein are those having color care benefit for a textile. Examples of cellulases that provide a color care benefit are disclosed in EP0495257, EP0531372, EP531315, WO96/11262, WO96/29397, WO94/07998; WO98/12307; WO95/24471, WO98/08940, and U.S. Pat. Nos. 5,457,046, 5,686,593 and 5,763,254, all of which are incorporated herein by reference. Examples of commercially available cellulases useful in a detergent include CELLUSOFT®, CELLUCLEAN®, CELLUZYME®, and CAREZYME® (Novo Nordisk A/S and Novozymes A/S); CLAZINASE®, PURADAX HA®, and REVITALENZ™ (DuPont Industrial Biosciences); BIOTOUCH® (AB Enzymes); and KAC-500(B)™ (Kao Corporation). Additional cellulases are disclosed in, e.g., U.S. Pat. Nos. 7,595, 182, 8,569,033, 7,138,263, 3,844,890, 4,435,307, 4,435,307, and GB2095275.

In some embodiments, a detergent composition can comprise one or more enzymes (e.g., any disclosed herein), each at a level from about 0.00001% to about 10% by weight of the composition and the balance of cleaning adjunct materials by weight of composition. In some other embodiments, a detergent composition can also comprise each enzyme at a level of about 0.0001% to about 10%, about 0.001% to about 5%, about 0.001% to about 2%, or about 0.005% to about 0.5%, by weight of the composition.

Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, lentus, amyloliquefaciens, subtilisin Carlsberg, subtilisin 309, subtilisin 147 and subtilisin 168). Additional examples include those mutant proteases described in U.S. Pat. Nos. RE34606, 5,955,340, 5,700,676, 6,312,936 and 6,482,628, all of which are incorporated herein by reference. Additional protease examples include, but are not limited to, trypsin (e.g., of porcine or bovine origin), and the Fusarium protease described in WO89/06270. In some embodiments, commercially available protease enzymes include, but are not limited to, MAXATASE®, MAXACAL™, MAXAPEM™ OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (Genencor); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ variants (Henkel Kommanditgesellschaft auf Aktien, Duesseldorf, Germany), and KAP (*B. alkalophilus* subtilisin; Kao Corp., Tokyo, Japan). Various proteases are described in WO95/23221, WO92/21760, WO09/149200, WO09/

149144, WO09/149145, WO11/072099, WO10/056640, WO10/056653, WO11/140364, WO12/151534, U.S. Pat. Publ. No. 2008/0090747, and U.S. Pat. Nos. 5,801,039, 5,340,735, 5,500,364, 5,855,625, RE34606, 5955340, 5700676, 6312936, 6482628, 8530219, and various other patents. In some further embodiments, neutral metalloproteases find use in the present disclosure, including but not limited to, the neutral metalloproteases described in WO1999014341, WO1999033960, WO1999014342, WO1999034003, WO2007044993, WO2009058303 and WO2009058661, all of which are incorporated herein by reference. Exemplary metalloproteases include nprE, the recombinant form of neutral metalloprotease expressed in *Bacillus subtilis* (See e.g., WO07/044993), and PMN, the purified neutral metalloprotease from *Bacillus amyloliquefaciens*.

Suitable mannanases include, but are not limited to, those of bacterial or fungal origin. Chemically or genetically modified mutants are included in some embodiments. Various mannanases are known which find use in the present disclosure (See, e.g., U.S. Pat. Nos. 6,566,114, 6,602,842, and 6,440,991, all of which are incorporated herein by reference). Commercially available mannanases that find use in the present disclosure include, but are not limited to MANNASTAR®, PURABRITE™, and MANNAWAY®.

Suitable lipases include those of bacterial or fungal origin. Chemically modified, proteolytically modified, or protein engineered mutants are included. Examples of useful lipases include those from the genera *Humicola* (e.g., *H. lanuginosa*, EP258068 and EP305216; *H. insolens*, WO96/13580), *Pseudomonas* (e.g., *P. alcaligenes* or *P. pseudoalcaligenes*, EP218272; *P. cepacia*, EP331376; *P. stutzeri*, GB1372034; *P. fluorescens* and *Pseudomonas* sp. strain SD 705, WO95/06720 and WO96/27002; *P. wisconsinensis*, WO96/12012); and *Bacillus* (e.g., *B. subtilis*, Dartois et al., Biochemica et Biophysica Acta 1131:253-360; *B. stearothermophilus*, JP64/744992; *B. pumilus*, WO91/16422). Furthermore, a number of cloned lipases find use in some embodiments of the present disclosure, including but not limited to, *Penicillium camembertii* lipase (See, Yamaguchi et al., Gene 103: 61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase. Additional lipases useful herein include, for example, those disclosed in WO92/05249, WO94/01541, WO95/35381, WO96/00292, WO95/30744, WO94/25578, WO95/14783, WO95/22615, WO97/04079, WO97/07202, EP407225 and EP260105. Other types of lipase polypeptide enzymes such as cutinases also find use in some embodiments of the present disclosure, including but not limited to, cutinase derived from *Pseudomonas mendocina* (See, WO88/09367), and cutinase derived from *Fusarium solani pisi* (See, WO90/09446). Examples of certain commercially available lipase enzymes useful herein include M1 LIPASE™ LUMA FAST™, and LIPOMAX™ (Genencor); LIPEX®, LIPOLASE® and LIPOLASE® ULTRA (Novozymes); and LIPASE P™ "Amano" (Amano Pharmaceutical Co. Ltd., Japan).

Suitable polyesterases include, for example, those disclosed in WO01/34899, WO01/14629 and U.S. Pat. No. 6,933,140.

A detergent composition herein can also comprise 2,6-beta-D-fructan hydrolase, which is effective for removal/cleaning of certain biofilms present on household and/or industrial textiles/laundry.

Suitable amylases include, but are not limited to those of bacterial or fungal origin. Chemically or genetically modified mutants are included in some embodiments. Amylases that find use in the present disclosure, include, but are not limited to, alpha-amylases obtained from *B. licheniformis* (See e.g., GB1296839). Additional suitable amylases include those disclosed in WO9510603, WO9526397, WO9623874, WO9623873, WO9741213, WO9919467, WO0060060, WO0029560, WO9923211, WO9946399, WO0060058, WO0060059, WO9942567, WO0114532, WO02092797, WO0166712, WO0188107, WO0196537, WO0210355, WO9402597, WO0231124, WO9943793, WO9943794, WO2004113551, WO2005001064, WO2005003311, WO0164852, WO2006063594, WO2006066594, WO2006066596, WO2006012899, WO2008092919, WO2008000825, WO2005018336, WO2005066338, WO2009140504, WO2005019443, WO2010091221, WO2010088447, WO0134784, WO2006012902, WO2006031554, WO2006136161, WO2008101894, WO2010059413, WO2011098531, WO2011080352, WO2011080353, WO2011080354, WO2011082425, WO2011082429, WO2011076123, WO2011087836, WO2011076897, WO94183314, WO9535382, WO9909183, WO9826078, WO9902702, WO9743424, WO9929876, WO9100353, WO9605295, WO9630481, WO9710342, WO2008088493, WO2009149419, WO2009061381, WO2009100102, WO2010104675, WO2010117511, and WO2010115021, all of which are incorporated herein by reference.

Suitable amylases include, for example, commercially available amylases such as STAINZYME®, STAINZYME PLUS®, NATALASE®, DURAMYL®, TERMAMYL®, TERMAMYL ULTRA®, FUNGAMYL® and BAN™ (Novo Nordisk A/S and Novozymes A/S); RAPIDASE®, POWERASE®, PURASTAR® and PREFERENZ™ (DuPont Industrial Biosciences).

Suitable peroxidases/oxidases contemplated for use in the compositions include those of plant, bacterial or fungal origin. Chemically modified or protein engineered mutants are included. Examples of peroxidases useful herein include those from the genus *Coprinus* (e.g., *C. cinereus*, WO93/24618, WO95/10602, and WO98/15257), as well as those referenced in WO2005056782, WO2007106293, WO2008063400, WO2008106214, and WO2008106215. Commercially available peroxidases useful herein include, for example, GUARDZYME™ (Novo Nordisk A/S and Novozymes A/S).

In some embodiments, peroxidases are used in combination with hydrogen peroxide or a source thereof (e.g., a percarbonate, perborate or persulfate) in the compositions of the present disclosure. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO94/12621 and WO95/01426). Suitable peroxidases/oxidases include, but are not limited to, those of plant, bacterial or fungal origin. Chemically or genetically modified mutants are included in some embodiments.

Enzymes that may be comprised in a detergent composition herein may be stabilized using conventional stabilizing agents, e.g., a polyol such as propylene glycol or glycerol; a sugar or sugar alcohol; lactic acid; boric acid or a boric acid derivative (e.g., an aromatic borate ester).

A detergent composition in certain embodiments may comprise one or more other types of polymers in addition to a dextran as disclosed herein. Examples of other types of polymers useful herein include carboxymethyl cellulose (CMC), poly(vinylpyrrolidone) (PVP), polyethylene glycol (PEG), poly(vinyl alcohol) (PVA), polycarboxylates such as polyacrylates, maleic/acrylic acid copolymers and lauryl methacrylate/acrylic acid copolymers.

A detergent composition herein may contain a bleaching system. For example, a bleaching system can comprise an $H_2O_2$ source such as perborate or percarbonate, which may be combined with a peracid-forming bleach activator such as tetraacetylethylenediamine (TAED) or nonanoyloxybenzenesulfonate (NOBS). Alternatively, a bleaching system may comprise peroxyacids (e.g., amide, imide, or sulfone type peroxyacids). Alternatively still, a bleaching system can be an enzymatic bleaching system comprising perhydrolase, for example, such as the system described in WO2005/056783.

A detergent composition herein may also contain conventional detergent ingredients such as fabric conditioners, clays, foam boosters, suds suppressors, anti-corrosion agents, soil-suspending agents, anti-soil redeposition agents, dyes, bactericides, tarnish inhibiters, optical brighteners, or perfumes. The pH of a detergent composition herein (measured in aqueous solution at use concentration) is usually neutral or alkaline (e.g., pH of about 7.0 to about 11.0).

It is believed that a dextran herein can be included as an anti-redeposition agent and/or clay soil removal agent in a detergent composition such as a fabric care composition, if desired (such agents can optionally be characterized as whiteness maintenance agents in certain aspects). Examples of other suitable anti-redeposition and/or clay soil removal agents herein include polyethoxy zwitterionic surfactants, water-soluble copolymers of acrylic or methacrylic acid with acrylic or methacrylic acid-ethylene oxide condensates (e.g., U.S. Pat. No. 3,719,647), cellulose derivatives such as carboxymethylcellulose and hydroxypropylcellulose (e.g., U.S. Pat. Nos. 3,597,416 and 3,523,088), and mixtures comprising nonionic alkyl polyethoxy surfactant, polyethoxy alkyl quaternary cationic surfactant and fatty amide surfactant (e.g., U.S. Pat. No. 4,228,044). Non-limiting examples of other suitable anti-redeposition and clay soil removal agents are disclosed in U.S. Pat. Nos. 4,597,898 and 4,891,160, and Int. Pat. Appl. Publ. No. WO95/32272, all of which are incorporated herein by reference.

Particular forms of detergent compositions that can be adapted for purposes disclosed herein are disclosed in, for example, US20090209445A1, US20100081598A1, U.S. Pat. No. 7,001,878B2, EP1504994B1, WO2001085888A2, WO2003089562A1, WO2009098659A1, WO2009-098660A1, WO2009112992A1, WO2009124160A1, WO2009152031A1, WO2010059483A1, WO2010-088112A1, WO2010090915A1, WO2010135238A1, WO2011094687A1, WO2011094690A1, WO2011-127102A1, WO2011163428A1, WO2008000567A1, WO2006045391A1, WO2006007911 A1, WO2012027404A1, EP1740690B1, WO2012059336A1, U.S. Pat. No. 6,730,646B1, WO2008087426A1, WO2010116139A1, and WO2012104613A1, all of which are incorporated herein by reference.

Laundry detergent compositions herein can optionally be heavy duty (all purpose) laundry detergent compositions. Exemplary heavy duty laundry detergent compositions comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, e.g., C8-C18 alkyl ethoxylated alcohols and/or C6-C12 alkyl phenol alkoxylates), where the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

A detergent herein such as a heavy duty laundry detergent composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

A detergent herein such as a heavy duty laundry detergent composition may optionally include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example REPEL-O-TEX SF, SF-2 AND SRP6, TEXCARE SRA100, SRA300, SRN100, SRN170, SRN240, SRN300 AND SRN325, MARLOQUEST SL), anti-redeposition agent(s) herein (0.1 wt % to 10 wt %), include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); and polymeric carboxylate (such as maleate/acrylate random copolymer or polyacrylate homopolymer).

A detergent herein such as a heavy duty laundry detergent composition may optionally further include saturated or unsaturated fatty acids, preferably saturated or unsaturated C12-C24 fatty acids (0 wt % to 10 wt %); deposition aids in addition to a dextran compound disclosed herein (examples for which include polysaccharides, cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic starch, cationic polyacylamides, and mixtures thereof.

A detergent herein such as a heavy duty laundry detergent composition may optionally further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDTA), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

A detergent herein such as a heavy duty laundry detergent composition may optionally include silicone or fatty-acid based suds suppressors; hueing dyes, calcium and magnesium cations, visual signaling ingredients, anti-foam (0.001 wt % to about 4.0 wt %), and/or a structurant/thickener (0.01 wt % to 5 wt %) selected from the group consisting of diglycerides and triglycerides, ethylene glycol distearate, microcrystalline cellulose, microfiber cellulose, biopolymers, xanthan gum, gellan gum, and mixtures thereof). Such structurant/thickener would be, in certain embodiments, in addition to the one or more dextran compounds comprised in the detergent. A structurant can also be referred to as a structural agent.

A detergent herein can be in the form of a heavy duty dry/solid laundry detergent composition, for example. Such a detergent may include: (i) a detersive surfactant, such as any anionic detersive surfactant disclosed herein, any non-ionic detersive surfactant disclosed herein, any cationic detersive surfactant disclosed herein, any zwitterionic and/or amphoteric detersive surfactant disclosed herein, any ampholytic surfactant, any semi-polar non-ionic surfactant, and mixtures thereof; (ii) a builder, such as any phosphate-free builder (e.g., zeolite builders in the range of 0 wt % to less than 10 wt %), any phosphate builder (e.g., sodium tri-polyphosphate in the range of 0 wt % to less than 10 wt %), citric acid, citrate salts and nitrilotriacetic acid, any silicate salt (e.g., sodium or potassium silicate or sodium meta-silicate in the range of 0 wt % to less than 10 wt %); any carbonate salt (e.g., sodium carbonate and/or sodium bicarbonate in the range of 0 wt % to less than 80 wt %), and mixtures thereof; (iii) a bleaching agent, such as any photobleach (e.g., sulfonated zinc phthalocyanines, sulfonated aluminum phthalocyanines, xanthenes dyes, and mixtures thereof), any hydrophobic or hydrophilic bleach activator (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), any source of hydrogen peroxide (e.g., inorganic perhydrate salts, examples of which include mono or tetra hydrate sodium salt of perborate, percarbonate, persulfate, perphosphate, or persilicate), any preformed hydrophilic and/or hydrophobic peracids (e.g., percarboxylic acids and salts, percarbonic acids and salts, perimidic acids and salts, peroxymonosulfuric acids and salts, and mixtures thereof); and/or (iv) any other components such as a bleach catalyst (e.g., imine bleach boosters examples of which include iminium cations and polyions, iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof), and a metal-containing bleach catalyst (e.g., copper, iron, titanium, ruthenium, tungsten, molybdenum, or manganese cations along with an auxiliary metal cations such as zinc or aluminum and a sequestrate such as EDTA, ethylenediaminetetra(methylenephosphonic acid).

Compositions disclosed herein can be in the form of a dishwashing detergent composition, for example. Examples of dishwashing detergents include automatic dishwashing detergents (typically used in dishwasher machines) and hand-washing dish detergents. A dishwashing detergent composition can be in any dry or liquid/aqueous form as disclosed herein, for example. Components that may be included in certain embodiments of a dishwashing detergent composition include, for example, one or more of a phosphate; oxygen- or chlorine-based bleaching agent; non-ionic surfactant; alkaline salt (e.g., metasilicates, alkali metal hydroxides, sodium carbonate); any active enzyme disclosed herein; anti-corrosion agent (e.g., sodium silicate); anti-foaming agent; additives to slow down the removal of glaze and patterns from ceramics; perfume; anti-caking agent (in granular detergent); starch (in tablet-based detergents); gelling agent (in liquid/gel based detergents); and/or sand (powdered detergents).

Dishwashing detergents such as an automatic dishwasher detergent or liquid dishwashing detergent can comprise (i) a non-ionic surfactant, including any ethoxylated non-ionic surfactant, alcohol alkoxylated surfactant, epoxy-capped poly(oxyalkylated) alcohol, or amine oxide surfactant present in an amount from 0 to 10 wt %; (ii) a builder, in the range of about 5-60 wt %, including any phosphate builder (e.g., mono-phosphates, di-phosphates, tri-polyphosphates, other oligomeric-polyphosphates, sodium tripolyphosphate-STPP), any phosphate-free builder (e.g., amino acid-based compounds including methyl-glycine-diacetic acid [MGDA] and salts or derivatives thereof, glutamic-N,N-diacetic acid [GLDA] and salts or derivatives thereof, iminodisuccinic acid (IDS) and salts or derivatives thereof, carboxy methyl inulin and salts or derivatives thereof, nitrilotriacetic acid [NTA], diethylene triamine penta acetic acid [DTPA], B-alaninediacetic acid [B-ADA] and salts thereof), homopolymers and copolymers of poly-carboxylic acids and partially or completely neutralized salts thereof, monomeric polycarboxylic acids and hydroxycarboxylic acids and salts thereof in the range of 0.5 wt % to 50 wt %, or sulfonated/carboxylated polymers in the range of about 0.1 wt % to about 50 wt %; (iii) a drying aid in the range of about 0.1 wt % to about 10 wt % (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds thereof, particularly of the reactive cyclic carbonate and urea type); (iv) a silicate in the range from about 1 wt % to about 20 wt % (e.g., sodium or potassium silicates such as sodium disilicate, sodium meta-silicate and crystalline phyllosilicates); (v) an inorganic bleach (e.g., perhydrate salts such as perborate, percarbonate, perphosphate, persulfate and persilicate salts) and/or an organic bleach (e.g., organic peroxyacids such as diacyl- and tetraacylperoxides, especially diperoxydodecanedioic acid, diperoxytetradecanedioic acid, and diperoxyhexadecanedioic acid); (vi) a bleach activator (e.g., organic peracid precursors in the range from about 0.1 wt % to about 10 wt %) and/or bleach catalyst (e.g., manganese triazacyclononane and related complexes; Co, Cu, Mn, and Fe bispyridylamine and related complexes; and pentamine acetate cobalt(III) and related complexes); (vii) a metal care agent in the range from about 0.1 wt % to 5 wt % (e.g., benzatriazoles, metal salts and complexes, and/or silicates); and/or (viii) any active enzyme disclosed herein in the range from about 0.01 to 5.0 mg of active enzyme per gram of automatic dishwashing detergent composition, and an enzyme stabilizer component (e.g., oligosaccharides, polysaccharides, and inorganic divalent metal salts).

Various examples of detergent formulations comprising at least one dextran herein are disclosed below (1-19):

1) A detergent composition formulated as a granulate having a bulk density of at least 600 g/L comprising: linear alkylbenzenesulfonate (calculated as acid) at about 7-12 wt %; alcohol ethoxysulfate (e.g., C12-18 alcohol, 1-2 ethylene oxide [EO]) or alkyl sulfate (e.g., C16-18) at about 1-4 wt %; alcohol ethoxylate (e.g., C14-15 alcohol) at about 5-9 wt %; sodium carbonate at about 14-20 wt %; soluble silicate (e.g., $Na_2O$ $2SiO_2$) at about 2-6 wt %; zeolite (e.g., NaAlSiO$_4$) at about 15-22 wt %; sodium sulfate at about 0-6 wt %; sodium citrate/citric acid at about 0-15 wt %; sodium perborate at about 11-18 wt %; TAED at about 2-6 wt %; dextran herein up to about 2 wt %; other polymers (e.g., maleic/acrylic acid copolymer, PVP, PEG) at about 0-3 wt %; optionally an enzyme(s) (calculated as pure enzyme protein) at about 0.0001-0.1 wt %; and minor ingredients (e.g., suds suppressors, perfumes, optical brightener, photobleach) at about 0-5 wt %.

2) A detergent composition formulated as a granulate having a bulk density of at least 600 g/L comprising: linear alkylbenzenesulfonate (calculated as acid) at about 6-11 wt %; alcohol ethoxysulfate (e.g., C12-18 alcohol, 1-2 EO) or alkyl sulfate (e.g., C16-18) at about 1-3 wt %; alcohol ethoxylate (e.g., C14-15 alcohol) at about 5-9 wt %; sodium carbonate at about 15-21 wt %; soluble silicate (e.g., $Na_2O$ $2SiO_2$) at about 1-4 wt %; zeolite (e.g., NaAlSiO$_4$) at about 24-34 wt %; sodium sulfate at about 4-10 wt %; sodium citrate/citric acid at about 0-15 wt %; sodium perborate at about 11-18 wt %; TAED at about 2-6 wt %; dextran herein up to about 2 wt %; other polymers (e.g., maleic/acrylic acid copolymer, PVP, PEG) at about 1-6 wt %; optionally an enzyme(s) (calculated as pure enzyme protein) at about 0.0001-0.1 wt %; and minor ingredients (e.g., suds suppressors, perfumes, optical brightener, photobleach) at about 0-5 wt %.

3) A detergent composition formulated as a granulate having a bulk density of at least 600 g/L comprising: linear alkylbenzenesulfonate (calculated as acid) at about 5-9 wt %; alcohol ethoxysulfate (e.g., C12-18 alcohol, 7 EO) at about 7-14 wt %; soap as fatty acid (e.g., C16-22 fatty acid) at about 1-3 wt %; sodium carbonate at about 10-17 wt %; soluble silicate (e.g., $Na_2O$ $2SiO_2$) at about 3-9 wt %; zeolite (e.g., NaAlSiO$_4$) at about 23-33 wt %; sodium sulfate at about 0-4 wt %; sodium perborate at about 8-16 wt %; TAED at about 2-8 wt %; phosphonate (e.g., EDTMPA) at about 0-1 wt %; dextran herein up to about 2 wt %; other polymers (e.g., maleic/acrylic acid copolymer, PVP, PEG) at about 0-3 wt %; optionally an enzyme(s) (calculated as pure enzyme protein) at about 0.0001-0.1 wt %; and minor ingredients (e.g., suds suppressors, perfumes, optical brightener) at about 0-5 wt %.

4) A detergent composition formulated as a granulate having a bulk density of at least 600 g/L comprising: linear alkylbenzenesulfonate (calculated as acid) at about 8-12 wt %; alcohol ethoxylate (e.g., C12-18 alcohol, 7 EO) at about 10-25 wt %; sodium carbonate at about 14-22 wt %; soluble silicate (e.g., $Na_2O$ $2SiO_2$) at about 1-5 wt %; zeolite (e.g., NaAlSiO$_4$) at about 25-35 wt %; sodium sulfate at about 0-10 wt %; sodium perborate at about 8-16 wt %; TAED at about 2-8 wt %; phosphonate (e.g., EDTMPA) at about 0-1 wt %; dextran herein up to about 2 wt %; other polymers (e.g., maleic/acrylic acid copolymer, PVP, PEG) at about 1-3 wt %; optionally an enzyme(s) (calculated as pure enzyme protein) at about 0.0001-0.1 wt %; and minor ingredients (e.g., suds suppressors, perfumes) at about 0-5 wt %.

5) An aqueous liquid detergent composition comprising: linear alkylbenzenesulfonate (calculated as acid) at about 15-21 wt %; alcohol ethoxylate (e.g., C12-18 alcohol, 7 EO; or C12-15 alcohol, 5 EO) at about 12-18 wt %; soap as fatty acid (e.g., oleic acid) at about 3-13 wt %; alkenylsuccinic acid (C12-14) at about 0-13 wt %; aminoethanol at about 8-18 wt %; citric acid at about 2-8 wt %; phosphonate at about 0-3 wt %; dextran herein up to about 2 wt %; other polymers (e.g., PVP, PEG) at about 0-3 wt %; borate at about 0-2 wt %; ethanol at about 0-3 wt %; propylene glycol at about 8-14 wt %; optionally an enzyme(s) (calculated as pure enzyme protein) at about 0.0001-0.1 wt %; and minor ingredients (e.g., dispersants, suds suppressors, perfume, optical brightener) at about 0-5 wt %.

6) An aqueous structured liquid detergent composition comprising: linear alkylbenzenesulfonate (calculated as acid) at about 15-21 wt %; alcohol ethoxylate (e.g., C12-18 alcohol, 7 EO; or C12-15 alcohol, 5 EO) at about 3-9 wt %; soap as fatty acid (e.g., oleic acid) at about 3-10 wt %; zeolite (e.g., NaAlSiO$_4$) at about 14-22 wt %; potassium citrate about 9-18 wt %; borate at about 0-2 wt %; dextran herein up to about 2 wt %; other polymers (e.g., PVP, PEG) at about 0-3 wt %; ethanol at about 0-3 wt %; anchoring polymers (e.g., lauryl methacrylate/acrylic acid copolymer, molar ratio 25:1, MW 3800) at about 0-3 wt %; glycerol at about 0-5 wt %; optionally an enzyme(s) (calculated as pure enzyme protein) at about 0.0001-0.1 wt %; and minor ingredients (e.g., dispersants, suds suppressors, perfume, optical brightener) at about 0-5 wt %.

7) A detergent composition formulated as a granulate having a bulk density of at least 600 g/L comprising: fatty alcohol sulfate at about 5-10 wt %, ethoxylated fatty acid monoethanolamide at about 3-9 wt %; soap as fatty acid at about 0-3 wt %; sodium carbonate at about 5-10 wt %; soluble silicate (e.g., $Na_2O$ $2SiO_2$) at about 1-4 wt %; zeolite (e.g., NaAlSiO$_4$) at about 20-40 wt %; sodium sulfate at about 2-8 wt %; sodium perborate at about 12-18 wt %; TAED at about 2-7 wt %; dextran herein up to about 2 wt %; other polymers (e.g., maleic/acrylic acid copolymer, PEG) at about 1-5 wt %; optionally an enzyme(s) (calculated as pure enzyme protein) at about 0.0001-0.1 wt %; and minor ingredients (e.g., optical brightener, suds suppressors, perfumes) at about 0-5 wt %.

8) A detergent composition formulated as a granulate comprising: linear alkylbenzenesulfonate (calculated as acid) at about 8-14 wt %; ethoxylated fatty acid monoethanolamide at about 5-11 wt %; soap as fatty acid at about 0-3 wt %; sodium carbonate at about 4-10 wt %; soluble silicate (e.g., $Na_2O$ $2SiO_2$) at about 1-4 wt %; zeolite (e.g., NaAlSiO$_4$) at about 30-50 wt %; sodium sulfate at about 3-11 wt %; sodium citrate at about 5-12 wt %; dextran herein up to about 2 wt %; other polymers (e.g., PVP, maleic/acrylic acid copolymer, PEG) at about 1-5 wt %; optionally an enzyme(s) (calculated as pure enzyme protein) at about 0.0001-0.1 wt %; and minor ingredients (e.g., suds suppressors, perfumes) at about 0-5 wt %.

9) A detergent composition formulated as a granulate comprising: linear alkylbenzenesulfonate (calculated as acid) at about 6-12 wt %; nonionic surfactant at about 1-4 wt %; soap as fatty acid at about 2-6 wt %; sodium carbonate at about 14-22 wt %; zeolite (e.g., NaAlSiO$_4$) at about 18-32 wt %; sodium sulfate at about 5-20 wt %; sodium citrate at about 3-8 wt %; sodium perborate at about 4-9 wt %; bleach activator (e.g., NOBS or TAED) at about 1-5 wt %; dextran herein up to about 2 wt %; other polymers (e.g., polycarboxylate or PEG) at about 1-5 wt %; optionally an enzyme(s) (calculated as pure enzyme protein) at about 0.0001-0.1 wt %; and minor ingredients (e.g., optical brightener, perfume) at about 0-5 wt %.

10) An aqueous liquid detergent composition comprising: linear alkylbenzenesulfonate (calculated as acid) at about 15-23 wt %; alcohol ethoxysulfate (e.g., C12-15 alcohol, 2-3 EO) at about 8-15 wt %; alcohol ethoxylate (e.g., C12-15 alcohol, 7 EO; or C12-15 alcohol, 5 EO) at about 3-9 wt %; soap as fatty acid (e.g., lauric acid) at about 0-3 wt %; aminoethanol at about 1-5 wt %; sodium citrate at about 5-10 wt %; hydrotrope (e.g., sodium toluenesulfonate) at about 2-6 wt %; borate at about 0-2 wt %; dextran herein up to about 1 wt %; ethanol at about 1-3 wt %; propylene glycol at about 2-5 wt %; optionally an enzyme(s) (calculated as pure enzyme protein) at about 0.0001-0.1 wt %; and minor ingredients (e.g., dispersants, perfume, optical brighteners) at about 0-5 wt %.

11) An aqueous liquid detergent composition comprising: linear alkylbenzenesulfonate (calculated as acid) at about 20-32 wt %; alcohol ethoxylate (e.g., C12-15 alcohol, 7 EO; or C12-15 alcohol, 5 EO) at about 6-12 wt %; aminoethanol at about 2-6 wt %; citric acid at about 8-14 wt %; borate at about 1-3 wt %; dextran herein up to about 2 wt %; ethanol at about 1-3 wt %; propylene glycol at about 2-5 wt %; other polymers (e.g., maleic/acrylic acid copolymer, anchoring polymer such as lauryl methacrylate/acrylic acid copolymer) at about 0-3 wt %; glycerol at about 3-8 wt %; optionally an enzyme(s) (calculated as pure enzyme protein) at about 0.0001-0.1 wt %; and minor ingredients (e.g., hydrotropes, dispersants, perfume, optical brighteners) at about 0-5 wt %.

12) A detergent composition formulated as a granulate having a bulk density of at least 600 g/L comprising: anionic surfactant (e.g., linear alkylbenzenesulfonate, alkyl sulfate, alpha-olefinsulfonate, alpha-sulfo fatty acid methyl esters, alkanesulfonates, soap) at about 25-40 wt %; nonionic surfactant (e.g., alcohol ethoxylate) at about 1-10 wt %; sodium carbonate at about 8-25 wt %; soluble silicate (e.g., Na$_2$O 2SiO$_2$) at about 5-15 wt %; sodium sulfate at about 0-5 wt %; zeolite (NaAlSiO$_4$) at about 15-28 wt %; sodium perborate at about 0-20 wt %; bleach activator (e.g., TAED or NOBS) at about 0-5 wt %; dextran herein up to about 2 wt %; optionally an enzyme(s) (calculated as pure enzyme protein) at about 0.0001-0.1 wt %; and minor ingredients (e.g., perfume, optical brighteners) at about 0-3 wt %.

13) Detergent compositions as described in (1)-(12) above, but in which all or part of the linear alkylbenzenesulfonate is replaced by C12-C18 alkyl sulfate.

14) A detergent composition formulated as a granulate having a bulk density of at least 600 g/L comprising: C12-C18 alkyl sulfate at about 9-15 wt %; alcohol ethoxylate at about 3-6 wt %; polyhydroxy alkyl fatty acid amide at about 1-5 wt %; zeolite (e.g., NaAlSiO$_4$) at about 10-20 wt %; layered disilicate (e.g., SK56 from Hoechst) at about 10-20 wt %; sodium carbonate at about 3-12 wt %; soluble silicate (e.g., Na$_2$O 2SiO$_2$) at 0-6 wt %; sodium citrate at about 4-8 wt %; sodium percarbonate at about 13-22 wt %; TAED at about 3-8 wt %; dextran herein up to about 2 wt %; other polymers (e.g., polycarboxylates and PVP) at about 0-5 wt %; optionally an enzyme(s) (calculated as pure enzyme protein) at about 0.0001-0.1 wt %; and minor ingredients (e.g., optical brightener, photobleach, perfume, suds suppressors) at about 0-5 wt %.

15) A detergent composition formulated as a granulate having a bulk density of at least 600 g/L comprising: C12-C18 alkyl sulfate at about 4-8 wt %; alcohol ethoxylate at about 11-15 wt %; soap at about 1-4 wt %; zeolite MAP or zeolite A at about 35-45 wt %; sodium carbonate at about 2-8 wt %; soluble silicate (e.g., Na$_2$O 2SiO$_2$) at 0-4 wt %; sodium percarbonate at about 13-22 wt %; TAED at about 1-8 wt %; dextran herein up to about 3 wt %; other polymers (e.g., polycarboxylates and PVP) at about 0-3 wt %; optionally an enzyme(s) (calculated as pure enzyme protein) at about 0.0001-0.1 wt %; and minor ingredients (e.g., optical brightener, phosphonate, perfume) at about 0-3 wt %.

16) Detergent formulations as described in (1)-(15) above, but that contain a stabilized or encapsulated peracid, either as an additional component or as a substitute for an already specified bleach system(s).

17) Detergent compositions as described in (1), (3), (7), (9) and (12) above, but in which perborate is replaced by percarbonate.

18) Detergent compositions as described in (1), (3), (7), (9), (12), (14) and (15) above, but that additionally contain a manganese catalyst. A manganese catalyst, for example, is one of the compounds described by Hage et al. (1994, *Nature* 369:637-639), which is incorporated herein by reference.

19) Detergent compositions formulated as a non-aqueous detergent liquid comprising a liquid non-ionic surfactant (e.g., a linear alkoxylated primary alcohol), a builder system (e.g., phosphate), dextran herein, optionally an enzyme(s), and alkali. The detergent may also comprise an anionic surfactant and/or bleach system.

It is believed that numerous commercially available detergent formulations can be adapted to include a dextran compound disclosed herein. Examples include PUREX® ULTRAPACKS (Henkel), FINISH® QUANTUM (Reckitt Benckiser), CLOROX™ 2 PACKS (Clorox), OXICLEAN MAX FORCE POWER PAKS (Church & Dwight), TIDE© STAIN RELEASE, CASCADE® ACTIONPACS, and TIDE® PODS™ (Procter & Gamble).

Compositions disclosed herein can be in the form of an oral care composition, for example. Examples of oral care compositions include dentifrices, toothpaste, mouth wash, mouth rinse, chewing gum, and edible strips that provide some form of oral care (e.g., treatment or prevention of cavities [dental caries], gingivitis, plaque, tartar, and/or periodontal disease). An oral care composition can also be for treating an "oral surface", which encompasses any soft or hard surface within the oral cavity including surfaces of the tongue, hard and soft palate, buccal mucosa, gums and dental surfaces. A "dental surface" herein is a surface of a natural tooth or a hard surface of artificial dentition including a crown, cap, filling, bridge, denture, or dental implant, for example.

An oral care composition herein can comprise about 0.01-15.0 wt % (e.g., ~0.1-10 wt % or ~0.1-5.0 wt %, ~0.1-2.0 wt %) of one or more dextran ether compounds as disclosed herein, for example. One or more dextran ether compounds comprised in an oral care composition can sometimes be provided therein as a thickening agent and/or dispersion agent, which may be useful to impart a desired consistency and/or mouth feel to the composition. One or more other thickening or dispersion agents can also be provided in an oral care composition herein, such as a carboxyvinyl polymer, carrageenan (e.g., L-carrageenan), natural gum (e.g., karaya, xanthan, gum arabic, tragacanth), colloidal magnesium aluminum silicate, or colloidal silica, for example.

An oral care composition herein may be a toothpaste or other dentifrice, for example. Such compositions, as well as any other oral care composition herein, can additionally comprise, without limitation, one or more of an anticaries agent, antimicrobial or antibacterial agent, anticalculus or tartar control agent, surfactant, abrasive, pH-modifying agent, foam modulator, humectant, flavorant, sweetener, pigment/colorant, whitening agent, and/or other suitable components. Examples of oral care compositions to which one or more dextran compounds can be added are disclosed in U.S. Patent Appl. Publ. Nos. 2006/0134025, 2002/0022006 and 2008/0057007, which are incorporated herein by reference.

An anticaries agent herein can be an orally acceptable source of fluoride ions. Suitable sources of fluoride ions include fluoride, monofluorophosphate and fluorosilicate salts as well as amine fluorides, including olaflur (N'-octadecyltrimethylendiamine-N,N,N'-tris(2-ethanol)-dihydrofluoride), for example. An anticaries agent can be present in an amount providing a total of about 100-20000 ppm, about 200-5000 ppm, or about 500-2500 ppm, fluoride ions to the composition, for example. In oral care compositions in which sodium fluoride is the sole source of fluoride ions, an amount of about 0.01-5.0 wt %, about 0.05-1.0 wt %, or about 0.1-0.5 wt %, sodium fluoride can be present in the composition, for example.

An antimicrobial or antibacterial agent suitable for use in an oral care composition herein includes, for example, phenolic compounds (e.g., 4-allylcatechol; p-hydroxybenzoic acid esters such as benzylparaben, butylparaben, ethylparaben, methylparaben and propylparaben; 2-benzylphenol; butylated hydroxyanisole; butylated hydroxytoluene; capsaicin; carvacrol; creosol; eugenol; guaiacol; halogenated bisphenolics such as hexachlorophene and bromochlorophene; 4-hexylresorcinol; 8-hydroxyquinoline and salts thereof; salicylic acid esters such as menthyl salicylate, methyl salicylate and phenyl salicylate; phenol; pyrocatechol; salicylanilide; thymol; halogenated diphenylether compounds such as triclosan and triclosan monophosphate), copper (II) compounds (e.g., copper (II) chloride, fluoride, sulfate and hydroxide), zinc ion sources (e.g., zinc acetate, citrate, gluconate, glycinate, oxide, and sulfate), phthalic acid and salts thereof (e.g., magnesium monopotassium phthalate), hexetidine, octenidine, sanguinarine, benzalkonium chloride, domiphen bromide, alkylpyridinium chlorides (e.g. cetylpyridinium chloride, tetradecylpyridinium chloride, N-tetradecyl-4-ethylpyridinium chloride), iodine, sulfonamides, bisbiguanides (e.g., alexidine, chlorhexidine, chlorhexidine digluconate), piperidino derivatives (e.g., delmopinol, octapinol), *magnolia* extract, grapeseed extract, rosemary extract, menthol, geraniol, citral, eucalyptol, antibiotics (e.g., augmentin, amoxicillin, tetracycline, doxycycline, minocycline, metronidazole, neomycin, kanamycin, clindamycin), and/or any antibacterial agents disclosed in U.S. Pat. No. 5,776,435, which is incorporated herein by reference. One or more antimicrobial agents can optionally be present at about 0.01-10 wt % (e.g., 0.1-3 wt %), for example, in the disclosed oral care composition.

An anticalculus or tartar control agent suitable for use in an oral care composition herein includes, for example, phosphates and polyphosphates (e.g., pyrophosphates), polyaminopropanesulfonic acid (AMPS), zinc citrate trihydrate, polypeptides (e.g., polyaspartic and polyglutamic acids), polyolefin sulfonates, polyolefin phosphates, diphosphonates (e.g., azacycloalkane-2,2-diphosphonates such as azacycloheptane-2,2-diphosphonic acid), N-methyl azacyclopentane-2,3-diphosphonic acid, ethane-1-hydroxy-1,1-diphosphonic acid (EHDP), ethane-1-amino-1,1-diphosphonate, and/or phosphonoalkane carboxylic acids and salts thereof (e.g., their alkali metal and ammonium salts). Useful inorganic phosphate and polyphosphate salts include, for example, monobasic, dibasic and tribasic sodium phosphates, sodium tripolyphosphate, tetrapolyphosphate, mono-, di-, tri- and tetra-sodium pyrophosphates, disodium dihydrogen pyrophosphate, sodium trimetaphosphate, sodium hexametaphosphate, or any of these in which sodium is replaced by potassium or ammonium. Other useful anticalculus agents in certain embodiments include anionic polycarboxylate polymers (e.g., polymers or copolymers of acrylic acid, methacrylic, and maleic anhydride such as polyvinyl methyl ether/maleic anhydride copolymers). Still other useful anticalculus agents include sequestering agents such as hydroxycarboxylic acids (e.g., citric, fumaric, malic, glutaric and oxalic acids and salts thereof) and aminopolycarboxylic acids (e.g., EDTA). One or more anticalculus or tartar control agents can optionally be present at about 0.01-50 wt % (e.g., about 0.05-25 wt % or about 0.1-15 wt %), for example, in the disclosed oral care composition.

A surfactant suitable for use in an oral care composition herein may be anionic, non-ionic, or amphoteric, for example. Suitable anionic surfactants include, without limitation, water-soluble salts of $C_{8-20}$ alkyl sulfates, sulfonated monoglycerides of $C_{8-20}$ fatty acids, sarcosinates, and taurates. Examples of anionic surfactants include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable non-ionic surfactants include, without limitation, poloxamers, polyoxyethylene sorbitan esters, fatty alcohol ethoxylates, alkylphenol ethoxylates, tertiary amine oxides, tertiary phosphine oxides, and dialkyl sulfoxides. Suitable amphoteric surfactants include, without limitation, derivatives of $C_{8-20}$ aliphatic secondary and tertiary amines having an anionic group such as a carboxylate, sulfate, sulfonate, phosphate or phosphonate. An example of a suitable amphoteric surfactant is cocoamidopropyl betaine. One or more surfactants are optionally present in a total amount of about 0.01-10 wt % (e.g., about 0.05-5.0 wt % or about 0.1-2.0 wt %), for example, in the disclosed oral care composition.

An abrasive suitable for use in an oral care composition herein may include, for example, silica (e.g., silica gel, hydrated silica, precipitated silica), alumina, insoluble phosphates, calcium carbonate, and resinous abrasives (e.g., a urea-formaldehyde condensation product). Examples of insoluble phosphates useful as abrasives herein are orthophosphates, polymetaphosphates and pyrophosphates, and include dicalcium orthophosphate dihydrate, calcium pyrophosphate, beta-calcium pyrophosphate, tricalcium phosphate, calcium polymetaphosphate and insoluble sodium polymetaphosphate. One or more abrasives are optionally present in a total amount of about 5-70 wt % (e.g., about 10-56 wt % or about 15-30 wt %), for example, in the disclosed oral care composition. The average particle size of an abrasive in certain embodiments is about 0.1-30 microns (e.g., about 1-20 microns or about 5-15 microns).

An oral care composition in certain embodiments may comprise at least one pH-modifying agent. Such agents may be selected to acidify, make more basic, or buffer the pH of a composition to a pH range of about 2-10 (e.g., pH ranging from about 2-8, 3-9, 4-8, 5-7, 6-10, or 7-9). Examples of pH-modifying agents useful herein include, without limitation, carboxylic, phosphoric and sulfonic acids; acid salts (e.g., monosodium citrate, disodium citrate, monosodium malate); alkali metal hydroxides (e.g. sodium hydroxide, carbonates such as sodium carbonate, bicarbonates, sesquicarbonates); borates; silicates; phosphates (e.g., monosodium phosphate, trisodium phosphate, pyrophosphate salts); and imidazole.

A foam modulator suitable for use in an oral care composition herein may be a polyethylene glycol (PEG), for example. High molecular weight PEGs are suitable, including those having an average molecular weight of about 200000-7000000 (e.g., about 500000-5000000 or about 1000000-2500000), for example. One or more PEGs are optionally present in a total amount of about 0.1-10 wt % (e.g. about 0.2-5.0 wt % or about 0.25-2.0 wt %), for example, in the disclosed oral care composition.

An oral care composition in certain embodiments may comprise at least one humectant. A humectant in certain embodiments may be a polyhydric alcohol such as glycerin, sorbitol, xylitol, or a low molecular weight PEG. Most suitable humectants also may function as a sweetener herein. One or more humectants are optionally present in a total amount of about 1.0-70 wt % (e.g., about 1.0-50 wt %, about 2-25 wt %, or about 5-15 wt %), for example, in the disclosed oral care composition.

A natural or artificial sweetener may optionally be comprised in an oral care composition herein. Examples of suitable sweeteners include dextrose, sucrose, maltose, dextrin, invert sugar, mannose, xylose, ribose, fructose, levulose, galactose, corn syrup (e.g., high fructose corn syrup or corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, and cyclamates. One or more sweeteners are optionally present in a total amount of about 0.005-5.0 wt %, for example, in the disclosed oral care composition.

A natural or artificial flavorant may optionally be comprised in an oral care composition herein. Examples of suitable flavorants include vanillin; sage; marjoram; parsley oil; spearmint oil; cinnamon oil; oil of wintergreen (methylsalicylate); peppermint oil; clove oil; bay oil; anise oil; eucalyptus oil; citrus oils; fruit oils; essences such as those derived from lemon, orange, lime, grapefruit, apricot, banana, grape, apple, strawberry, cherry, or pineapple; bean- and nut-derived flavors such as coffee, cocoa, cola, peanut, or almond; and adsorbed and encapsulated flavorants. Also encompassed within flavorants herein are ingredients that provide fragrance and/or other sensory effect in the mouth, including cooling or warming effects. Such ingredients include, without limitation, menthol, menthyl acetate, menthyl lactate, camphor, eucalyptus oil, eucalyptol, anethole, eugenol, cassia, oxanone, Irisone®, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), and menthone glycerol acetal (MGA). One or more flavorants are optionally present in a total amount of about 0.01-5.0 wt % (e.g., about 0.1-2.5 wt %), for example, in the disclosed oral care composition.

An oral care composition in certain embodiments may comprise at least one bicarbonate salt. Any orally acceptable bicarbonate can be used, including alkali metal bicarbonates such as sodium or potassium bicarbonate, and ammonium bicarbonate, for example. One or more bicarbonate salts are optionally present in a total amount of about 0.1-50 wt % (e.g., about 1-20 wt %), for example, in the disclosed oral care composition.

An oral care composition in certain embodiments may comprise at least one whitening agent and/or colorant. A suitable whitening agent is a peroxide compound such as any of those disclosed in U.S. Pat. No. 8,540,971, which is incorporated herein by reference. Suitable colorants herein include pigments, dyes, lakes and agents imparting a particular luster or reflectivity such as pearling agents, for example. Specific examples of colorants useful herein include talc; mica; magnesium carbonate; calcium carbonate; magnesium silicate; magnesium aluminum silicate; silica; titanium dioxide; zinc oxide; red, yellow, brown and black iron oxides; ferric ammonium ferrocyanide; manganese violet; ultramarine; titaniated mica; and bismuth oxychloride. One or more colorants are optionally present in a total amount of about 0.001-20 wt % (e.g., about 0.01-10 wt % or about 0.1-5.0 wt %), for example, in the disclosed oral care composition.

Additional components that can optionally be included in an oral composition herein include one or more enzymes (above), vitamins, and anti-adhesion agents, for example. Examples of vitamins useful herein include vitamin C, vitamin E, vitamin B5, and folic acid. Examples of suitable anti-adhesion agents include solbrol, ficin, and quorum-sensing inhibitors.

The present disclosure also concerns a method for increasing the viscosity of an aqueous composition. This method comprises contacting at least one dextran compound as presently disclosed with the aqueous composition. The contacting step in this method results in increasing the viscosity of the aqueous composition, in comparison to the viscosity of the aqueous composition before the contacting step.

An aqueous composition herein can be water (e.g., deionized water), an aqueous solution, or a hydrocolloid, for example. The viscosity of an aqueous composition before the contacting step, measured at about 20-25° C., can be about 0-10000 cPs (or any integer between 0-10000 cPs), for example. Since the aqueous composition can be a hydrocolloid or the like in certain embodiments, it should be apparent that the method can be used to increase the viscosity of aqueous compositions that are already viscous.

Contacting dextran herein with an aqueous composition increases the viscosity of the aqueous composition in certain embodiments. This increase in viscosity can be an increase of at least about 1%, 10%, 100%, 1000%, 100000%, or 1000000% (or any integer between 1% and 1000000%), for example, compared to the viscosity of the aqueous composition before the contacting step. It should be apparent that very large percent increases in viscosity can be obtained with the disclosed method when the aqueous composition has little to no viscosity before the contacting step. An increase in viscosity can be determined, for example, by comparing the viscosity of the aqueous composition obtained by the method (i.e., after the contacting step) with the viscosity of the aqueous composition as it had existed before the method (i.e., before the contacting step).

Contacting dextran herein with an aqueous composition increases the shear thinning behavior or shear thickening behavior of the aqueous composition in certain embodiments. Thus, dextran rheologically modifies the aqueous composition in these embodiments. The increase in shear thinning behavior or shear thickening behavior can be an increase of at least about 1%, 10%, 100%, 1000%, 100000%, or 1000000% (or any integer between 1% and 1000000%), for example, compared to the shear thinning behavior or shear thickening behavior of the aqueous composition before the contacting step. It should be apparent that very large percent increases in rheologic modification can be obtained with the disclosed method when the aqueous composition has little to no rheologic behavior before the contacting step.

The contacting step in a method for increasing the viscosity of an aqueous composition can be performed by mixing or dissolving any dextran as presently disclosed in the aqueous composition by any means known in the art. For example, mixing or dissolving can be performed manually or with a machine (e.g., industrial mixer or blender, orbital shaker, stir plate, homogenizer, sonicator, bead mill). Mixing or dissolving can comprise a homogenization step in certain embodiments. Homogenization (as well as any other type of mixing) can be performed for about 5 to 60, 5 to 30, 10 to 60, 10 to 30, 5 to 15, or 10 to 15 seconds (or any integer between 5 and 60 seconds), or longer periods of time as necessary to mix dextran with the aqueous composition. A homogenizer can be used at about 5000 to 30000 rpm, 10000 to 30000 rpm, 15000 to 30000 rpm, 15000 to 25000 rpm, or 20000 rpm (or any integer between 5000 and 30000 rpm), for example.

After a dextran herein is mixed with or dissolved into an aqueous composition, the resulting aqueous composition may be filtered, or may not be filtered. For example, an aqueous composition prepared with a homogenization step may or may not be filtered.

Certain embodiments of the above method can be used to prepare an aqueous composition disclosed herein, such as a food product (e.g., a confectionery such as a candy filling), pharmaceutical product (e.g., excipient), household product (e.g., laundry detergent, fabric softener, dishwasher detergent), personal care product (e.g., a water-containing dentifrice such as toothpaste), or industrial product.

The present disclosure also concerns a method of treating a material. This method comprises contacting a material with an aqueous composition comprising at least one dextran compound as disclosed herein.

A material contacted with an aqueous composition in a contacting method herein can comprise a fabric in certain embodiments. A fabric herein can comprise natural fibers, synthetic fibers, semi-synthetic fibers, or any combination thereof. A semi-synthetic fiber herein is produced using naturally occurring material that has been chemically derivatized, an example of which is rayon. Non-limiting examples of fabric types herein include fabrics made of (i) cellulosic fibers such as cotton (e.g., broadcloth, canvas, chambray, chenille, chintz, corduroy, cretonne, damask, denim, flannel, gingham, jacquard, knit, matelassé, oxford, percale, poplin, plissé, sateen, seersucker, sheers, terry cloth, twill, velvet), rayon (e.g., viscose, modal, lyocell), linen, and Tencel®; (ii) proteinaceous fibers such as silk, wool and related mammalian fibers; (iii) synthetic fibers such as polyester, acrylic, nylon, and the like; (iv) long vegetable fibers from jute, flax, ramie, coir, kapok, sisal, henequen, abaca, hemp and sunn; and (v) any combination of a fabric of (i)-(iv). Fabric comprising a combination of fiber types (e.g., natural and synthetic) include those with both a cotton fiber and polyester, for example. Materials/articles containing one or more fabrics herein include, for example, clothing, curtains, drapes, upholstery, carpeting, bed linens, bath linens, tablecloths, sleeping bags, tents, car interiors, etc. Other materials comprising natural and/or synthetic fibers include, for example, non-woven fabrics, paddings, paper, and foams.

An aqueous composition that is contacted with a fabric can be, for example, a fabric care composition (e.g., laundry detergent, fabric softener). Thus, a treatment method in certain embodiments can be considered a fabric care method or laundry method if employing a fabric care composition therein. A fabric care composition herein is contemplated to effect one or more of the following fabric care benefits (i.e., surface substantive effects): wrinkle removal, wrinkle reduction, wrinkle resistance, fabric wear reduction, fabric wear resistance, fabric pilling reduction, extended fabric life, fabric color maintenance, fabric color fading reduction, reduced dye transfer, fabric color restoration, fabric soiling reduction, fabric soil release, fabric shape retention, fabric smoothness enhancement, anti-redeposition of soil on fabric, anti-greying of laundry, improved fabric hand/handle, and/or fabric shrinkage reduction.

Examples of conditions (e.g., time, temperature, wash/rinse volumes) for conducting a fabric care method or laundry method herein are disclosed in WO1997/003161 and U.S. Pat. Nos. 4,794,661, 4,580,421 and 5,945,394, which are incorporated herein by reference. In other examples, a material comprising fabric can be contacted with an aqueous composition herein: (i) for at least about 5, 10, 20, 30, 40, 50, 60, 70, 80, 90, 100, 110, or 120 minutes; (ii) at a temperature of at least about 10, 15, 20, 25, 30, 35, 40, 45, 50, 55, 60, 65, 70, 75, 80, 85, 90, or 95° C. (e.g., for laundry wash or rinse: a "cold" temperature of about 15-30° C., a "warm" temperature of about 30-50° C., a "hot" temperature of about 50-95° C.); (iii) at a pH of about 2, 3, 4, 5, 6, 7, 8, 9, 10, 11, or 12 (e.g., pH range of about 2-12, or about 3-11); (iv) at a salt (e.g., NaCl) concentration of at least about 0.5, 1.0, 1.5, 2.0, 2.5, 3.0, 3.5, or 4.0 wt %; or any combination of (i)-(iv).

The contacting step in a fabric care method or laundry method can comprise any of washing, soaking, and/or rinsing steps, for example. Contacting a material or fabric in still further embodiments can be performed by any means known in the art, such as dissolving, mixing, shaking, spraying, treating, immersing, flushing, pouring on or in, combining, painting, coating, applying, affixing to, and/or communicating an effective amount of a dextran compound herein with the fabric or material. In still further embodiments, contacting may be used to treat a fabric to provide a surface substantive effect. As used herein, the term "fabric hand" or "handle" refers to a person's tactile sensory response towards fabric which may be physical, physiological, psychological, social or any combination thereof. In one embodiment, the fabric hand may be measured using a PhabrOmeter® System for measuring relative hand value (available from Nu Cybertek, Inc. Davis, CA) (American Association of Textile Chemists and Colorists (AATCC test method "202-2012, Relative Hand Value of Textiles: Instrumental Method")).

In certain embodiments of treating a material comprising fabric, a dextran compound component(s) of the aqueous composition adsorbs to the fabric. This feature is believed to render dextran compounds herein useful as anti-redeposition agents and/or anti-greying agents in fabric care compositions disclosed (in addition to their viscosity-modifying effect). An anti-redeposition agent or anti-greying agent herein helps keep soil from redepositing onto clothing in wash water after the soil has been removed. It is further contemplated that adsorption of one or more dextran compounds herein to a fabric enhances mechanical properties of the fabric.

Adsorption of a dextran compound to a fabric herein can be measured using a colorimetric technique (e.g., Dubois et al., 1956, *Anal. Chem.* 28:350-356; Zemljic̆ et al., 2006, *Lenzinger Berichte* 85:68-76; both incorporated herein by reference), for example, or any other method known in the art.

Other materials that can be contacted in the above treatment method include surfaces that can be treated with a dish detergent (e.g., automatic dishwashing detergent or hand dish detergent). Examples of such materials include surfaces of dishes, glasses, pots, pans, baking dishes, utensils and flatware made from ceramic material, china, metal, glass, plastic (e.g., polyethylene, polypropylene, polystyrene, etc.) and wood (collectively referred to herein as "tableware"). Thus, the treatment method in certain embodiments can be considered a dishwashing method or tableware washing method, for example. Examples of conditions (e.g., time, temperature, wash volume) for conducting a dishwashing or tableware washing method herein are disclosed in U.S. Pat. No. 8,575,083, which is incorporated herein by reference. In other examples, a tableware article can be contacted with an aqueous composition herein under a suitable set of conditions such as any of those disclosed above with regard to contacting a fabric-comprising material.

Other materials that can be contacted in the above treatment method include oral surfaces such as any soft or hard surface within the oral cavity including surfaces of the tongue, hard and soft palate, buccal mucosa, gums and dental surfaces (e.g., natural tooth or a hard surface of artificial dentition such as a crown, cap, filling, bridge, denture, or dental implant). Thus, a treatment method in certain embodiments can be considered an oral care method or dental care method, for example. Conditions (e.g., time, temperature) for contacting an oral surface with an aqueous composition herein should be suitable for the intended purpose of making such contact. Other surfaces that can be contacted in a treatment method also include a surface of the integumentary system such as skin, hair or nails.

Thus, certain embodiments of the present disclosure concern material (e.g., fabric) that comprises a dextran compound herein. Such material can be produced following a material treatment method as disclosed herein, for example. A material may comprise a dextran compound in certain embodiments if the compound is adsorbed to, or otherwise in contact with, the surface of the material.

Certain embodiments of a method of treating a material herein further comprise a drying step, in which a material is dried after being contacted with the aqueous composition. A drying step can be performed directly after the contacting step, or following one or more additional steps that might follow the contacting step (e.g., drying of a fabric after being rinsed, in water for example, following a wash in an aqueous composition herein). Drying can be performed by any of several means known in the art, such as air drying (e.g., ~20-25° C.), or at a temperature of at least about 30, 40, 50, 60, 70, 80, 90, 100, 120, 140, 160, 170, 175, 180, or 200° C., for example. A material that has been dried herein typically has less than 3, 2, 1, 0.5, or 0.1 wt % water comprised therein. Fabric is a preferred material for conducting an optional drying step.

An aqueous composition used in a treatment method herein can be any aqueous composition disclosed herein, such as in the above embodiments or in the below Examples. Thus, the dextran component(s) of an aqueous composition can be any as disclosed herein. Examples of aqueous compositions include detergents (e.g., laundry detergent or dish detergent) and water-containing dentifrices such as toothpaste.

The present disclosure also concerns an enzymatic reaction comprising water, sucrose and a glucosyltransferase enzyme comprising, or consisting of, an amino acid sequence that is at least 90% identical to SEQ ID NO:1, SEQ ID NO:2, SEQ ID NO:5, SEQ ID NO:9, SEQ ID NO:13, or SEQ ID NO:17. The glucosyltransferase enzyme synthesizes dextran as presently disclosed. Significantly, dextran synthesized in this gtf reaction exhibits high viscosity in aqueous compositions, even at relatively low concentrations of the dextran. It is believed that this high viscosity profile is unique in comparison to viscosity profiles of previously disclosed dextran polymers.

Dextran synthesized in an enzymatic reaction herein can be as characterized (e.g., molecular weight, linkage and branching profile) in the above disclosure regarding dextran as produced by a glucosyltransferase enzyme. A glucosyltransferase enzyme in an enzymatic reaction herein can be as characterized in the above disclosure regarding dextran as produced by a glucosyltransferase enzyme.

One or more different glucosyltransferase enzymes may be used in an enzymatic reaction herein. A single glucosyltransferase enzyme (e.g., gtf 0768) is used in some cases, as opposed to situations in which multiple enzymes may be present (e.g., a bacterial or yeast fermentation). An enzymatic reaction can be as characterized (e.g., initial sucrose concentration and sucrose type, pH, temperature, time) in the above disclosure regarding dextran as produced by a glucosyltransferase enzyme. Also, any features presently disclosed of a method of producing dextran can apply to a glucosyltransferase reaction.

The present disclosure also concerns a method for producing dextran comprising the step of contacting at least water, sucrose, and a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17. This contacting step results in production of dextran as presently disclosed. Dextran produced in the contacting step can optionally be isolated.

Dextran synthesized in a synthesis method herein can be as characterized (e.g., molecular weight, linkage and branching profile) in the above disclosure regarding dextran as produced by a glucosyltransferase enzyme. A glucosyltransferase enzyme in a synthesis method herein can be as characterized in the above disclosure regarding dextran as produced by a glucosyltransferase enzyme. Any features of an enzymatic reaction as disclosed above can apply to the instant synthesis method.

The contacting step in a method herein of producing dextran comprises providing an enzymatic reaction comprising water, sucrose and any glucosyltransferase enzyme disclosed herein. The contacting step of the disclosed method can be performed in any number of ways. For example, the desired amount of sucrose can first be dissolved in water (optionally, other components may also be added at this stage of preparation, such as buffer components), followed by addition of one or more glucosyltransferase enzymes. The solution may be kept still, or agitated via stirring or orbital shaking, for example.

The reaction can be, and typically is, cell-free. Thus, a dextran herein is not isolated from a cell, such as a bacteria (e.g., *L. mesenteroides*), in some aspects.

Completion of a glucosyltransferase reaction in certain embodiments can be gauged, for example, by determining whether reaction viscosity is no longer increasing and/or by measuring the amount of sucrose left in the reaction (residual sucrose), where a percent sucrose consumption of over about 90% can indicate reaction completion. Typically, a reaction of the disclosed process can take about 2, 3, 4, 5, 6, 7, 8, 9, 10, 12, 18, 24, 30, 36, 48, 60, 72, 84, or 96 hours to complete. Reaction time may depend, for example, on certain parameters such as the amount of sucrose and glucosyltransferase enzyme used in the reaction.

The yield of dextran produced in a glucosyltransferase reaction in certain embodiments can be about, or at least about, 10%, 15%, 20%, 25%, 30%, 35%, 40%, or 45%, based on the weight of the sucrose used in the reaction.

Dextran produced in the disclosed method may optionally be isolated. For example, dextran may be precipitated with alcohol (e.g., 90-100% methanol, ethanol, or isopropanol) and then separated from the supernatant, which may comprise water, fructose, and optionally one or more of residual sucrose and byproduct (e.g., glucose; leucrose and other soluble oligosaccharides). Such separation can be by centrifugation or filtration, for example. Precipitated dextran can optionally be washed one or more times (e.g., 2-4 times; 2, 3, 4 or more times) with alcohol (e.g., 70-100%, or at least 70%, 80%, 90%, 95%, or 100% methanol, ethanol, or isopropanol). In other examples, dextran isolation can comprise using an ultrafiltration and/or dialysis technique (i.e., a molecular weight cut-off technique), such as disclosed in U.S. Patent Appl. Publ. No. 2014/0142294 and U.S. Pat. No. 6,977,249, which are incorporated herein by reference. Measurements of certain dextran features herein (e.g., linkage profile, molecular weight) can be made with dextran isolated as above, if desired.

A dextran synthesis method herein is believed to be useful for producing dextran with increased or decreased viscosity, depending on the amount of sucrose used in the method. In general, the lower the sucrose concentration used in a glucosyltransferase reaction, the higher the viscosity of the dextran product, and vice versa. Any sucrose concentration disclosed herein can be used in a glucosyltransferase reaction, where the dextran product of the reaction has a viscosity that is greater than that of a dextran product produced in a reaction comprising a higher sucrose concentration, and vice versa. In certain aspects, any viscosity disclosed herein can be used to characterize embodiments of this method, and an increase in viscosity can be at least about 2-, 3-, 4-, 5-, 6-, 7-, 8-, 9-, 10-, 20-, 50-, 100-, 150-, 200-, or 250-fold higher. A glucosyltransferase enzyme in certain embodiments of this method can be gtf 0768 (comprising SEQ ID NO:1 or related sequences).

Non-limiting examples of compositions and methods disclosed herein include:

1. A composition comprising dextran, wherein the dextran comprises:
    (i) about 87-93 wt % glucose linked at positions 1 and 6;
    (ii) about 0.1-1.2 wt % glucose linked at positions 1 and 3;
    (iii) about 0.1-0.7 wt % glucose linked at positions 1 and 4;
    (iv) about 7.7-8.6 wt % glucose linked at positions 1, 3 and 6; and
    (v) about 0.4-1.7 wt % glucose linked at:
        (a) positions 1, 2 and 6, or
        (b) positions 1, 4 and 6;
   wherein the weight-average molecular weight (Mw) of the dextran is about 50-200 million Daltons, the z-average radius of gyration of the dextran is about 200-280 nm, and the dextran optionally is not a product of a *Leuconostoc mesenteroides* glucosyltransferase enzyme.

2. The composition of embodiment 1, wherein the dextran comprises:
    (i) about 89.5-90.5 wt % glucose linked at positions 1 and 6;
    (ii) about 0.4-0.9 wt % glucose linked at positions 1 and 3;
    (iii) about 0.3-0.5 wt % glucose linked at positions 1 and 4;
    (iv) about 8.0-8.3 wt % glucose linked at positions 1, 3 and 6; and
    (v) about 0.7-1.4 wt % glucose linked at:
        (a) positions 1, 2 and 6, or
        (b) positions 1, 4 and 6.

3. The composition of embodiment 1 or 2, wherein the dextran comprises chains linked together within a branching structure, wherein the chains are similar in length and comprise substantially alpha-1,6-glucosidic linkages.

4. The composition of embodiment 1, 2, or 3, wherein the average length of the chains is about 10-50 monomeric units.

5. The composition of embodiment 1, 2, 3, or 4, wherein the dextran is a product of a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17.

6. The composition of embodiment 1, 2, 3, 4, or 5, wherein the composition is an aqueous composition having a viscosity of at least about 25 cPs.

7. The composition of embodiment 1, 2, 3, 4, 5, or 6, wherein the Mw of the dextran is about 80-120 million Daltons.

8. The composition of embodiment 1, 2, 3, 4, 5, 6, or 7, wherein the z-average radius of gyration of the dextran is about 230-250 nm.

9. The composition of embodiment 1, 2, 3, 4, 5, 6, 7, or 8, wherein the composition is in the form of a food product, personal care product, pharmaceutical product, household product, or industrial product.

10. The composition of embodiment 9, wherein the composition is in the form of a confectionery.

11. A method for increasing the viscosity of an aqueous composition, the method comprising: contacting dextran according to any of embodiments 1-8 with the aqueous composition, wherein the viscosity of the aqueous composition is increased by the dextran compared to the viscosity of the aqueous composition before the contacting step.

12. A method of treating a material, the method comprising: contacting a material with an aqueous composition comprising dextran according to any of embodiments 1-8.

13. An enzymatic reaction comprising water, sucrose and a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17, wherein the glucosyltransferase enzyme synthesizes dextran according to any of embodiments 1-8.

14. A method for producing dextran, the method comprising:
    a) contacting at least water, sucrose, and a glucosyltransferase enzyme comprising an amino acid sequence that is at least 90% identical to SEQ ID NO:1, SEQ ID NO:2, SEQ ID NO:5, SEQ ID NO:9, SEQ ID NO:13, or SEQ ID NO:17, whereby dextran according to any of embodiments 1-8 is produced; and b) optionally, isolating the dextran produced in step (a).

15. The method of embodiment 14, wherein the viscosity of the dextran produced in the method is increased by decreasing the amount of sucrose in step (a).

EXAMPLES

The present disclosure is further defined in Examples 1-6 and 8-11. It should be understood that these Examples, while indicating certain preferred aspects of the disclosure, are given by way of illustration only. From the above discussion and these Examples, one skilled in the art can ascertain the essential characteristics of this disclosure, and without departing from the spirit and scope thereof, can make various changes and modifications to adapt the disclosure to various uses and conditions.

General Methods

Cloning and Expression of Glucosyltransferase Enzymes in *Bacillus subtilis*

Each glucosyltransferase used in Examples 3-6 was prepared as follows.

A plasmid encoding the gtf enzyme (pZZHB582, pZZHB583, pZZHB584, or pZZHB585, which allow for gtf expression and secretion from *B. subtilis*; see FIGS. 2A-D) was amplified using Illustra TempliPhi® 100 Amplification Kit (GE Healthcare Life Sciences, NJ). Competent *B. subtilis* cells (ΔspoIIE, ΔaprE, ΔnprE, degUHy32, ΔscoC, ΔnprB, Δvpr, Δepr, ΔwprA, Δmpr, ΔispA, Δbpr) were transformed with the amplification product. Cells were plated on Luria Agar plates supplemented with 5 ppm chloramphenicol. Colonies from the transformation plate were inoculated into 5 mL LB medium and incubated at 37° C. overnight. Aliquots (25-50 μL) from each culture were then transferred to 250-mL shake flasks containing 30 mL of Grant's II Medium supplemented with 5 ppm chloramphenicol and incubated at 30° C. with shaking (280 rpm) for 24 hours. Cells were harvested by centrifugation at 14000 rpm for 1 hour. Supernatants were analyzed by SDS-PAGE for secreted gtf product and further dialyzed three times against a solution containing 20 mM Tris, pH 7.5 for a total of 20 hours. Dialyzed samples were aliquoted at 25 mL per 50-mL conical centrifuge tube, and the tubes were placed at an angle at −80° C. for about 1 hour. Once the samples were frozen, the tube lid was removed and replaced with PARAFILM that was pierced 5-10 times with a high-gauge needle. The PARAFILM-covered frozen samples were lyophilized in a FreeZone® Freeze Dry System (Labconco Corp., Kansas City, MO) according to the manufacturer's instruction.

Stock Solutions of Glucosyltransferase Enzymes

An enzyme stock solution was made for each gtf by adding 10 mL of molecular grade $H_2O$ into each 50-mL conical centrifuge tube containing lyophilized enzyme powder.

Example 1

Expression of a Glucosyltransferase (0768) in *E. coli* and Production of Active Crude Enzyme Lysate This Example describes expression of a mature glucosyltransferase (gtf) enzyme in *E. coli*. Crude cell lysate of an *E. coli* expression strain was produced and showed gel product-forming activity in the presence of sucrose.

A putative YG repeat-containing hydrolase (categorized in GENBANK under GI number 339480768, but now having GI number 497964659) with 1484 amino acids was identified from *Leuconostoc pseudomesenteroides* strain KCTC3652 by whole genome shotgun sequencing. This putative glucosyltransferase (designated herein as gtf 0768) belongs to the GH70 family of glycosyl hydrolases containing a glucan-binding domain. The N-terminal 37 amino acid segment of gtf 0768 was deduced as the signal peptide of the enzyme by the SIGNALP 4.0 program (Petersen et al., *Nature Methods* 8:785-786). The mature form of gtf 0768 is represented by SEQ ID NO:1.

To construct a plasmid for bacterial expression of gtf 0768, a DNA sequence encoding a mature form of the gtf without the signal peptide was synthesized by GenScript USA Inc. (Piscataway, N. J.). The synthesized sequence was subcloned into the NheI and HindIII sites of the pET23D+ vector (NOVAGEN®; Merck KGaA, Darmstadt, Germany). The 0768 gtf (SEQ ID NO:2) encoded by this construct included a start methionine and 3 additional amino acids (Ala-Ser-Ala) at the N-terminus, and 6 histidine residues at the C-terminus, compared to the wild type mature (predicted) form of gtf 0768 (SEQ ID NO:1) (i.e., SEQ ID NO:1 is comprised in SEQ ID NO:2). The plasmid construct was sequence-confirmed and transformed into *E. coli* BL21 DE3 host cells with ampicillin selection, resulting in expression strain EC0052.

Cells of EC0052 and a control strain containing only empty pET23D+ vector were grown in LB medium with 100 μg/mL ampicillin to $OD_{600}$~0.5, and then induced with 1 mM IPTG at 37° C. for 3 hours or alternatively induced at 23° C. overnight. Following this induction period, cells were collected by centrifugation at 4000×g for 10 min and resuspended in PBS buffer pH 6.8. The cells were then lysed by passing through a French Press at 14,000 psi (~96.53 MPa) twice, afterwhich cell debris was pelleted by centrifugation at 15,000×g for 20 min. The supernatants of each crude cell lysate were aliquoted and frozen at −80° C.

The activity of crude cell lysate from EC0052 cells was checked by reaction with sucrose. A control reaction was set up similarly using cell lysate prepared from cells containing the empty vector. Each sucrose reaction was set up using 10% (v/v) of cell lysate with 100 g/L sucrose, 10 mM sodium citrate pH 5, and 1 mM $CaCl_2$. After incubation of the reactions at 37° C. for a few hours, a gel-like product, believed to be a dextran, was formed in the tube in which EC0052 cell lysate had been added. No gel-like product was formed in the control reaction. HPLC analysis confirmed that sucrose was consumed in the reaction containing EC0052 cell lysate, and not in the control reaction. This result suggested that the EC0052 crude cell lysate expressed active gtf 0768 enzyme, and that this gtf produced a dextran product having high viscosity.

Thus, reactions comprising water, sucrose and an enzyme comprising SEQ ID NO:1 synthesized a gelling product, believed to be a dextran. This result demonstrated that gtf 0768 likely has glucosyltransferase activity.

Example 2

Reaction of Sucrose with Gtf 0768 and Analysis of a Gelling Dextran Reaction Product This Example describes additional reactions comprising water, sucrose and gtf 0768, supplementing the results provided in Example 1. Also, this Example provides glycosidic linkage analysis of the gelling product synthesized by gtf 0768, showing that this product is a type of dextran.

Reagents for preparing gtf reactions:
Sucrose (Sigma Prod. No. S-9378).
Sodium phosphate buffer stock (200 mM) (pH 5.5): prepare 250 mL in water using sodium phosphate monobasic monohydrate (Sigma Prod. No. S9638) and sodium phosphate dibasic heptahydrate (Sigma Prod. No. S9390), accordingly.
Gtf 0768 enzyme solution (cell lysate as prepared in Example 1).

Conditions of Three Gtf Reactions:

A 1000-mL reaction was prepared containing 2.72 g of sodium phosphate buffer stock (pH 5.5), 100 g/L sucrose, and 2 mL of gtf 0768 enzyme solution. The reaction was stirred at 26° C. for 20 hours, and became viscous. The gtf enzyme was deactivated by heating the reaction at 80° C. for 10 minutes. The deactivated viscous reaction was then mixed with 3 liters of 100% methanol to precipitate the viscous product. A white precipitate was formed, which was then filtered, followed by four washes with 120 ml of 100% methanol. The solid product was dried at room temperature under vacuum in an oven for 72 hours.

A 725-mL reaction was prepared containing 1.97 g of sodium phosphate buffer, 300 g/L sucrose, and 1.45 mL of gtf 0768 enzyme solution. The reaction was stirred at 26° C. for 20 hours, and became viscous. The gtf enzyme was deactivated by adding methanol to the reaction mixture. The deactivated reaction was then mixed with 3 liters of 100% methanol to precipitate the viscous product. A white precipitate was formed, which was then filtered, followed by four washes with 120 mL of 100% methanol. The solid product was dried at room temperature under vacuum in an oven for 72 hours.

A 200-mL reaction was prepared containing 0.544 g of sodium phosphate buffer, 400 g/L sucrose, and 0.4 mL of gtf 0768 enzyme solution. The reaction was stirred at 26° C. for 20 hours, and became viscous. The gtf enzyme was deactivated by adding methanol to the reaction mixture. The deactivated reaction was then mixed with 3 liters of 100% methanol to precipitate the viscous product. A white precipitate was formed, which was then filtered, followed by four washes with 120 mL of 100% methanol. The solid product was dried at room temperature under vacuum in an oven for 72 hours.

A 200-mL reaction was prepared containing 0.544 g of sodium phosphate buffer, 800 g/L sucrose, and 0.4 mL of gtf 0768 enzyme solution. The reaction was stirred at 26° C. for 20 hours, and became viscous. The gtf enzyme was deactivated by adding methanol to the reaction mixture. The deactivated reaction was then mixed with 3 liters of 100% methanol to precipitate the viscous product. A white precipitate was formed, which was then filtered, followed by four washes with 120 ml of 100% methanol. The solid product was dried at room temperature under vacuum in an oven for 72 hours.

Samples (100 µL) of each reaction were taken at 0, 2, 4, and 18 hours, respectively. The gtf enzyme was deactivated in each sample by heating at 80° C. for 10 minutes. Each sample was then diluted 10-fold with water and centrifuged at 14,000 rpm for 5 minutes, after which 200 µl of supernatant was used for HPLC analysis to measure sucrose consumption during the reaction. The following HPLC conditions were applied for analyzing each sample: column (AMINEX HPX-87C carbohydrate column, 300×7.8 mm, Bio-Rad, No. 125-0095), eluent (water), flow rate (0.6 mL/min), temperature (85° C.), refractive index detector. HPLC analysis of the samples indicated substantial sucrose consumption during the 0768 gtf reaction (FIG. 1, reaction comprising 100 g/L sucrose) (this sucrose consumption occurred significantly faster than the sucrose consumption observed in a reaction using a dextran sucrase obtained from a commercial source—refer to Example 7).

HPLC was also used to analyze other products of the reaction comprising 100 g/L sucrose. Polymer yield was back-calculated by subtracting the amount of all other saccharides left in the reaction from the amount of the starting sucrose. The back-calculated number was consistent with the viscous product dry weight analysis. Sucrose, leucrose, glucose and fructose were quantified by HPLC with an HPX-87C column (HPLC conditions as described above). DP2-7 disaccharides were quantified by HPLC with the following conditions: column (AMINEX HPX-42A carbohydrate column, 300×7.8 mm, Bio-Rad, No. 125-0097), eluent (water), flow rate (0.6 mL/min), temperature (85° C.), refractive index detector. These HPLC analyses indicated that the glucosyl-containing saccharide products of the 0768 gtf reaction consisted of 91% polymer product, 1% glucose, 6.5% leucrose, and 1.5% DP2-7 oligosaccharides.

The glycosidic linkage profile of the gelling polymer product of the reaction comprising 100 g/L sucrose was determined by $^{13}$C NMR. Dry polymer (25-30 mg) as prepared above was dissolved in 1 mL of deuterated DMSO containing 3 wt % LiCl with stirring at 50° C. Using a glass pipet, 0.8 mL of the preparation was transferred into a 5-mm NMR tube. A quantitative $^{13}$C NMR spectrum was acquired using a Bruker Avance (Billerica, MA) 500 MHz NMR spectrometer equipped with a CPDul cryoprobe, at a spectral frequency of 125.76 MHz, using a spectral window of 26041.7 Hz. An inverse-gated decoupling pulse sequence using waltz decoupling was used with an acquisition time of 0.629 second, an inter-pulse delay of 5 seconds, and 6000 pulses. The time domain data were transformed using an exponential multiplication of 2.0 Hz.

The NMR results indicated that the gelling polymer product comprised about 90% alpha-1,6-glucosidic linkages, about 4-5% alpha-1,3-glucosidic linkages, and about 5-6% alpha-1,4 and -1,2 glucosidic linkages. The main chain(s) of the polymer product appeared to mostly comprise alpha-1,6-glucosidic linkages, but also a very small amount of alpha-1,3 and -1,4 glucosidic linkages. Other alpha-1,3 and -1,4 glucosidic linkages, and all of the alpha-1,2-glucosidic linkages, appeared to be in branches off the main chain(s). The gelling product thus appears to be a gelling dextran.

A different protocol (not the above $^{13}$C NMR procedure) is presently recommended herein for determining the linkage profile of dextran produced by gtf 0768. This protocol is disclosed below in Example 9, indicating a linkage profile similar to that disclosed in this Example.

The number-average molecular weight (Mn) and weight-average molecular weight (Mw) of the gelling dextran product of the reaction comprising 100 g/L sucrose was determined by size-exclusion chromatography (SEC). Dry polymer as prepared above was dissolved in DMAc and 5% LiCl (0.5 mg/mL) with shaking overnight at 100° C. The chromatographic system used was an Alliance™ 2695 separation module from Waters Corporation (Milford, MA) coupled with three on-line detectors: a differential refractometer 2410 from Waters, a Heleos™ 8+ multiangle light scattering photometer from Wyatt Technologies (Santa Barbara, CA), and a ViscoStar™ differential capillary viscometer from Wyatt. Columns used for SEC were four styrene-divinyl benzene columns from Shodex (Japan) and two linear KD-806M, KD-802 and KD-801 columns to improve resolution at the low molecular weight region of a polymer distribution. The mobile phase was DMAc with 0.11% LiCl. The chromatographic conditions used were 50° C. in the column and detector compartments, 40° C. in the sample and injector compartment, a flow rate of 0.5 mL/min, and an injection volume of 100 μL. The software packages used for data reduction were Empower™ version 3 from Waters (calibration with broad glucan polymer standard) and Astra® version 6 from Wyatt (triple detection method with column calibration). It was determined from this procedure that the gelling dextran product had an Mn of 2229400 and an Mw of 5365700.

A different protocol (not the above SEC procedure) is presently recommended herein for determining the molecular weight of dextran produced by gtf 0768. This protocol is disclosed below in Example 9, indicating a molecular weight more than one order of magnitude greater than the molecular weight disclosed in this Example.

Thus, reactions comprising water, sucrose and an enzyme comprising SEQ ID NO:1 synthesized a gelling dextran product, as determined by the product's predominant alpha-1,6 glucosidic linkage profile. Example 8 below discloses comparing the viscosity of this product versus the viscosities of certain commercially available dextrans. Example 9 discloses further production of dextran with a gtf enzyme comprising SEQ ID NO:1, along with yield, molecular weight, and linkage analysis of the dextran.

Example 3

Expression of a Glucosyltransferase (2919) and Use Thereof to Produce a Gelling Dextran Product This Example describes expression of a mature *Weissella cibaria* glucosyltransferase (gtf) enzyme in *B. subtilis*. Also, this Example shows that this enzyme produces a gelling product, likely a dextran, when used is a reaction containing water and sucrose.

A glucosyltransferase gene, WciGtf1, was identified from *Weissella cibaria* KACC 11862. The nucleic acid sequence of this gene (positions 23315 to 27661 of GENBANK Accession No. NZ_AEKT01000035.1) is set forth in SEQ ID NO:3 and encodes the protein sequence of SEQ ID NO:4 (GENBANK Accession No. ZP_08417432). At the N-terminus of the WciGtf1 protein (SEQ ID NO:4) is a signal peptide of 26 amino acids, as predicted by the SIGNALP 4.0 program (Petersen et al., *Nature Methods* 8:785-786). This indicates that WciGtf1 (SEQ ID NO:4) is a secreted protein. The mature, secreted form of the WciGtf1 protein is herein referred to as 2919 gtf, and is set forth in SEQ ID NO:5.

The nucleotide sequence encoding 2919 gtf was optimized for expression in *B. subtilis*. The optimized sequence (SEQ ID NO:6) was synthesized by Generay (Shanghai, China), and inserted into plasmid p2JM103BBI (Vogtentanz et al., *Protein Expr. Purif.* 55:40-52), resulting in plasmid pZZHB583 (FIG. 2A). Plasmid pZZHB583 contains an aprE promoter operably linked to a sequence encoding (i) an aprE signal sequence used to direct heterologous protein (2919 gtf in this case) secretion in *B. subtilis*, (ii) Ala-Gly-Lys to facilitate the secretion, and (iii) 2919 gtf (SEQ ID NO:5) (i-iii are fused together in the amino-to-carboxy direction).

Plasmid pZZHB583 was transformed into *B. subtilis* cells for 2919 gtf expression and purification (see General Methods).

The activity of 2919 gtf (SEQ ID NO:5) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 48 hours.

Samples (100 μL) were taken from the reaction at 0, 1, 3, 5, 24, and 48 hour time points, respectively. Enzyme was deactivated by heating each sample at 80° C. for 10 minutes. Samples were diluted 10-fold with water and centrifuged at 14000 rpm for 5 minutes. Supernatant (200 μL) was used for HPLC analysis.

The concentrations of leucrose, glucose, and fructose in the gtf reaction were determined using HPLC, which was performed with an Agilent 1260 chromatography system equipped with an AMINEX HPX-87C column (300×7.8 mm) placed in a thermostated column compartment at 85° C., and a refractive index detector. HPLC elution was carried out with Milli-Q® water at 0.6 mL/min. Sucrose, leucrose, glucose, and fructose were identified by comparison with corresponding standards. Their concentrations were calculated based on a peak area standard curves. Sucrose was consumed almost completely by the end of the reaction. Aside from a viscous dextran product, 2919 gtf (SEQ ID NO:5) produced mostly fructose (~50%), and small amounts of leucrose (~5%) and glucose (~1%).

The concentration of oligosaccharides (DP2-DP7) in the gtf reaction was determined by HPLC analysis, which was performed with an Agilent 1260 chromatography system equipped with an AMINEX HPX-42A column (300×7.8 mm) placed in a thermostated column compartment at 85° C., and a refractive index detector. HPLC elution was carried out with Milli-Q® water at 0.6 mL/min. Formation of oligosaccharides was identified by comparison with corresponding standards. The concentration of the oligosaccharides was calculated based on standard curves from peak area. 2919 gtf (SEQ ID NO:5) produced a small amount of DP2-DP7 oligosaccharides (~3%) by the end of the reaction.

Thus, reactions comprising water, sucrose and an enzyme comprising SEQ ID NO:5 synthesized a gelling product, which is believed to be a dextran polymer. Experimental results demonstrated that gtf 2919 likely has glucosyltransferase activity.

Example 4

Expression of a Glucosyltransferase (2918) and Use Thereof to Produce a Gelling Dextran Product This Example describes expression of a mature *Lactobacillus fermentum* glucosyltransferase (gtf) enzyme in *B. subtilis*. Also, this Example shows that this enzyme produces a gelling product, likely a dextran, when used is a reaction containing water and sucrose.

A glucosyltransferase gene, LfeGtf1, was identified from *Lactobacillus fermentum*. The nucleic acid sequence of this gene (positions 618 to 5009 of GENBANK Accession No. AY697433.1) is set forth in SEQ ID NO:7 and encodes the protein sequence of SEQ ID NO:8 (GENBANK Accession No. AAU08008). At the N-terminus of the LfeGtf1 protein (SEQ ID NO:8) is a signal peptide of 37 amino acids, as predicted by the SIGNALP 4.0 program. This indicates that LfeGtf1 (SEQ ID NO:8) is a secreted protein. The mature, secreted form of the LfeGtf1 protein is herein referred to as 2918 gtf, and is set forth in SEQ ID NO:9.

The nucleotide sequence encoding 2918 gtf was optimized for expression in *B. subtilis*. The optimized sequence (SEQ ID NO:10) was synthesized by Generay (Shanghai, China), and inserted into plasmid p2JM103BBI, resulting in plasmid pZZHB582 (FIG. 2B). Plasmid pZZHB582 contains an aprE promoter operably linked to a sequence encoding (i) an aprE signal sequence used to direct heterologous protein (2918 gtf in this case) secretion in *B. subtilis*, (ii) Ala-Gly-Lys to facilitate the secretion, and (iii) 2918 gtf (SEQ ID NO:9) (i-iii are fused together in the amino-to-carboxy direction).

Plasmid pZZHB582 was transformed into *B. subtilis* cells for 2918 gtf expression and purification (see General Methods).

The activity of 2918 gtf (SEQ ID NO:9) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 6 days.

Samples (100 µL) were taken from the reaction at 0, 1, 3, 5, 24, 48 and 144 hour time points, respectively. Enzyme was deactivated by heating each sample at 80° C. for 10 minutes. Samples were diluted 10-fold with water and centrifuged at 14000 rpm for 5 minutes. Supernatant (200 µL) was used for HPLC analysis.

The concentrations of sucrose, leucrose, glucose, fructose and oligosaccharides (DP2-DP7) in the gtf reaction were determined using HPLC procedures as described in Example 3. Sucrose was consumed almost completely by the end of the reaction. Aside from a viscous dextran product, 2918 gtf (SEQ ID NO:9) produced mostly fructose (~50%), and small amounts of leucrose (~5%) and glucose (~1%). 2918 gtf (SEQ ID NO:9) produced a small amount of DP2-DP7 oligosaccharides (~1%).

Thus, reactions comprising water, sucrose and an enzyme comprising SEQ ID NO:9 synthesized a gelling product, which is believed to be a dextran polymer. Experimental results demonstrated that gtf 2920 likely has glucosyltransferase activity.

Example 5

Expression of a Glucosyltransferase (2920) and Use Thereof to Produce a Gelling Dextran Product This Example describes expression of a mature *Streptococcus sobrinus* glucosyltransferase (gtf) enzyme in *B. subtilis*. Also, this Example shows that this enzyme produces a gelling product, likely a dextran, when used is a reaction containing water and sucrose.

A glucosyltransferase gene, SsoGtf4, was identified from *Streptococcus sobrinus* B13N. The nucleic acid sequence of this gene (positions 198 to 4718 of GENBANK Accession No. AY966490) is set forth in SEQ ID NO:11 and encodes the protein sequence of SEQ ID NO:12 (GENBANK Accession No. AAX76986). At the N-terminus of the SsoGtf4 protein (SEQ ID NO:12) is a signal peptide of 41 amino acids, as predicted by the SIGNALP 4.0 program. This indicates that SsoGtf4 (SEQ ID NO:12) is a secreted protein. The mature, secreted form of the SsoGtf4 protein is herein referred to as 2920 gtf, and is set forth in SEQ ID NO:13.

The nucleotide sequence encoding 2920 gtf was optimized for expression in *B. subtilis*. The optimized sequence (SEQ ID NO:14) was synthesized by Generay (Shanghai, China), and inserted into plasmid p2JM103BBI, resulting in plasmid pZZHB584 (FIG. 2C). Plasmid pZZHB584 contains an aprE promoter operably linked to a sequence encoding (i) an aprE signal sequence used to direct heterologous protein (2920 gtf in this case) secretion in *B. subtilis*, (ii) Ala-Gly-Lys to facilitate the secretion, and (iii) 2920 gtf (SEQ ID NO:13) (i-iii are fused together in the amino-to-carboxy direction).

Plasmid pZZHB584 was transformed into *B. subtilis* cells for 2920 gtf expression and purification (see General Methods).

The activity of 2920 gtf (SEQ ID NO:13) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 6 days.

Samples (100 µL) were taken from the reaction at 0, 1, 3, 5, 24, 48, 72 and 144 hour time points, respectively. Enzyme was deactivated by heating each sample at 80° C. for 10 minutes. Samples were diluted 10-fold with water and centrifuged at 14000 rpm for 5 minutes. Supernatant (200 µL) was used for HPLC analysis.

The concentrations of sucrose, leucrose, glucose, fructose and oligosaccharides (DP2-DP7) in the gtf reaction were determined using HPLC procedures as described in Example 3. Sucrose was consumed almost completely by the end of the reaction. Aside from a viscous dextran product, 2920 gtf (SEQ ID NO:13) produced mostly fructose (~50%), leucrose (~20%), and a small amount of glucose (~3%). 2920 gtf (SEQ ID NO:13) produced a small amount of DP2-DP7 oligosaccharides (~1%).

Thus, reactions comprising water, sucrose and an enzyme comprising SEQ ID NO:13 synthesized a gelling product, which is believed to be a dextran polymer. Experimental results demonstrated that gtf 2920 likely has glucosyltransferase activity.

Example 6

Expression of a Glucosyltransferase (2921) and Use Thereof to Produce a Gelling Dextran Product This Example describes expression of a mature *Streptococcus downei* glucosyltransferase (gtf) enzyme in *B. subtilis*. Also, this Example shows that this enzyme produces a gelling product, likely a dextran, when used is a reaction containing water and sucrose.

A glucosyltransferase gene, SdoGtf7, was identified from *Streptococcus downei* MFe28. The nucleic acid sequence of this gene (positions 16 to 2375 of GENBANK Accession No. AB476746) is set forth in SEQ ID NO:15 and encodes the protein sequence of SEQ ID NO:16 (GENBANK Accession No. ZP_08549987.1). At the N-terminus of the SdoGtf7 protein (SEQ ID NO:16) is a signal peptide of 44 amino acids, as predicted by the SIGNALP 4.0 program. This indicates that SdoGtf7 protein (SEQ ID NO:16) is a secreted protein. The mature, secreted form of the SdoGtf7 protein is herein referred to as 2921 gtf, and is set forth in SEQ ID NO:17.

The nucleotide sequence encoding 2921 gtf was optimized for expression in *B. subtilis*. The optimized sequence (SEQ ID NO:18) was synthesized by Generay (Shanghai, China), and inserted into plasmid p2JM103BBI, resulting in plasmid pZZHB585 (FIG. 2D). Plasmid pZZHB585 contains an aprE promoter operably linked to a sequence encoding (i) an aprE signal sequence used to direct heterologous protein (2921 gtf in this case) secretion in *B. subtilis*, (ii) Ala-Gly-Lys to facilitate the secretion, and (iii) 2921 gtf (SEQ ID NO:17) (i-iii are fused together in the amino-to-carboxy direction).

Plasmid pZZHB585 was transformed into *B. subtilis* cells for 2921 gtf expression and purification (see General Methods).

The activity of 2921 gtf (SEQ ID NO:17) was determined in a 250-mL reaction at room temperature comprising 100 g/L sucrose, 20 mM sodium phosphate buffer (pH 5.5), and 6.25 mL of enzyme stock. The reaction was carried out at room temperature with shaking (150 rpm) for 8 days.

Samples (100 μL) were taken from the reaction at the reaction start and on 1, 2, 3, 6, 7 and 8 day time points, respectively. Enzyme was deactivated by heating each sample at 80° C. for 10 minutes. Samples were diluted 10-fold with water and centrifuged at 14000 rpm for 5 minutes. Supernatant (200 μL) was used for HPLC analysis.

The concentrations of sucrose, leucrose, glucose, fructose and oligosaccharides (DP2-DP7) in the gtf reaction were determined using HPLC procedures as described in Example 3. About 43% sucrose remained in the reaction on day 8. Aside from a viscous dextran product, 2921 gtf (SEQ ID NO:17) produced mostly fructose (~31%), leucrose (~6%), and glucose (~3%). No obvious production of DP2-DP7 oligosaccharides was observed.

Thus, reactions comprising water, sucrose and an enzyme comprising SEQ ID NO:17 synthesized a gelling product, which is believed to be a dextran polymer. Experimental results demonstrated that gtf 2921 likely has glucosyltransferase activity.

Example 7 (Comparative)

Production of Dextran Using Commercially Available Dextran Sucrase

This Example describes synthesizing dextran using a commercially available dextran sucrase in reactions comprising water and sucrose. The dextran produced in this was analyzed in Example 8 in comparison to the gelling dextran products synthesized in Examples 1-6.

Reagents for Preparing Dextran Sucrase Reaction:
  Sucrose (Sigma Prod. No. S-9378). 400 g/L stock solution was prepared.
  Sodium phosphate buffer stock (200 mM) (pH 5.5): prepare 250 mL in water using sodium phosphate monobasic monohydrate (Sigma Prod. No. S9638) and sodium phosphate dibasic heptahydrate (Sigma Prod. No. S9390), accordingly.
  Dextran sucrase, lyophilized powder, 100 units/mg protein, from *Leuconostoc mesenteroides* (Sigma Prod. No. D9909).

A 50-mL reaction was prepared containing 20 mM sodium phosphate (pH 5.5), 110 g/L sucrose, and 10 units of dextran sucrase from Sigma-Aldrich. The dextran sucrase was added last when preparing the reaction. The reaction was carried out in a 125-mL capped shake flask at 26° C. with shaking (100 rpm) for 7 days. Samples (100 μL) of the reaction were taken at 0, 3, 6, 24, 48 and 168 hours, respectively. The dextran sucrase was deactivated in each sample by heating at 80° C. for 10 minutes. Each sample was then diluted 10-fold with water and centrifuged at 14,000 rpm for 5 minutes, afterwhich 200 μl of supernatant was used for HPLC analysis to measure sucrose consumption during the reaction.

The following HPLC conditions were applied for analyzing each sample: column (AMINEX HPX-87C carbohydrate column, 300×7.8 mm, Bio-Rad, No. 125-0095), eluent (water), flow rate (0.6 mL/min), temperature (85° C.), refractive index detector. HPLC analysis of the samples indicated sucrose consumption during the dextran sucrase reaction (FIG. 3). It is notable that the sucrose consumption rate by the commercial dextran sucrase was much slower compared to the sucrose consumption rate of gtf 0768 (Example 2). Specifically, while gtf 0768 depleted most sucrose after about 17-18 hours of reaction time (FIG. 1), commercial dextran sucrase depleted only about 20% of sucrose within this same time period, and required about 168 hours to deplete all or most sucrose.

HPLC was also used to analyze other products of the reaction. Dextran yield was back-calculated by subtracting the amount of all other saccharides left in the reaction from the amount of the starting sucrose. The back-calculated number was consistent with dextran dry weight analysis. Sucrose, leucrose, glucose, fructose, and DP2-7 disaccharides were quantified by HPLC as described in Example 2. These HPLC analyses indicated that the saccharide products of the commercial dextran sucrase reaction consisted of 49% dextran, 0.3% sucrose, 44% fructose, 1% glucose, 5% leucrose, and 1% DP2-7 oligosaccharides.

The dextran produced in this Example was analyzed in Example 8 in comparison to the gelling dextran products synthesized in Examples 1-6.

Example 8

Viscosity of Dextran Samples

This Example describes measuring the viscosities of the dextran polymers produced in Examples 1-7, as well as the viscosity of dextran obtained from a commercial source. Viscosity measurements were made at various shear rates.

Dextran polymer samples were prepared as described in Examples 1-7. Specifically, enzymatic reactions were conducted, afterwhich polymer was methanol-precipitated and washed with methanol (100%) four times, and then dried. Solutions (2 wt % and/or 3 wt %) of each sample were prepared by adding the appropriate amount of polymer to de-ionized (DI) water. Each preparation was then mixed using a bench top vortexer until polymer was fully in solution. Each of these samples is referred to in Tables 2 and 3 (below) as "After PPT" (after precipitation). A 2 wt % solution of dextran (Mw=956978) obtained from TCI America (Portland, OR; catalogue No. D0061) was similarly prepared; this dextran is referred to below as "commercial dextran".

To determine the viscosity of each polymer solution at various shear rates, each solution was subjected to various shear rates using a viscometer while the temperature was held constant at 20° C. Also, polymer samples obtained directly, without precipitation, from each of the enzymatic reactions described in Examples 1-7 were subjected to various shear rates (referred to in Tables 2 and 3 as "Before PPT"). The shear rate was increased using a gradient program which increased from 0-10 rpm and the shear rate was increased by 0.17 (1/s) every 30 seconds. The results of this experiment are listed in Table 2.

TABLE 2

Viscosity of Certain Dextran Solutions at Various Shear Rates

| Dextran Sample[a] | Viscosity (cPs) @ 0.17 rpm | Viscosity (cPs) @ 1.03 rpm | Viscosity (cPs) @ 2.62 rpm | Viscosity (cPs) @ 4.22 rpm |
|---|---|---|---|---|
| Gtf 0768 (SEQ ID NO: 1) Before PPT (Example 2, 100 g/L sucrose reaction) | 47976.13 | 11376.70 | 12956.11 | 14390.76 |
| Gtf 0768 (SEQ ID NO: 1) After PPT - 3 wt % (Example 2, 100 g/L sucrose reaction) | | 15778.40 | 6245.31[b] | 4119.58[b] |
| Gtf 0768 (SEQ ID NO: 1) After PPT - 2 wt % (Example 2, 100 g/L sucrose reaction) | | 4091.84 | 3417.10 | 2874.10 |
| Gtf 2918 (SEQ ID NO: 9) Before PPT (Example 4) | | n/a[b] | n/a[b] | n/a[b] |
| Gtf 2919 (SEQ ID NO: 5) Before PPT (Example 3) | | 98864 | 38671 | 25580 |
| Gtf 2920 (SEQ ID NO: 13) Before PPT (Example 5) | | 3874.85 | 4205.66 | 4119.58[b] |
| Gtf 2920 (SEQ ID NO: 13) After PPT - 3 wt % (Example 5) | | 6168.76 | 3294.43 | 2288.24 |
| Gtf 2921 (SEQ ID NO: 17) Before PPT (Example 6) | | 3533.86 | 2143.72 | 1748.95 |
| Gtf 2921 (SEQ ID NO: 17) After PPT - 3 wt % (Example 6) | | 4634.32 | 2780.4 | 1984.89 |
| Commercial dextran sucrase Before PPT (Example 7) | 16759.42 | | | |

[a]Polymer samples are listed according to the respective enzyme used to synthesize the sample.
[b]Measurement was outside the specification limits of the viscometer.

Polymer samples were also subjected to various higher shear rates using a viscometer while the temperature was held constant at 20° C. The shear rate was increased using a gradient program which increased from 10-250 rpm and the shear rate was increased by 7.36 (1/s) every 20 seconds. The results of this experiment are listed in Table 3.

TABLE 3

Viscosity of Certain Dextran Solutions at Various Shear Rates

| Dextran Sample[a] | Viscosity (cPs) @ 14.72 rpm | Viscosity (cPs) @ 102.9 rpm | Viscosity (cPs) @ 250 rpm |
|---|---|---|---|
| Gtf 2918 (SEQ ID NO: 9) After PPT - 3 wt % (Example 4) | 149.95 | 69.68 | 48.97 |
| Gtf 2919 (SEQ ID NO: 5) After PPT - 3 wt % (Example 3) | 80.82 | 41.23 | 29.49 |
| 2 wt % Commercial dextran (Example 7) | 241.41 | 105.28 | 68.88 |
| Commercial dextran sucrase After PPT - 2 wt % | 11.09[b] | 10.31[b] | 8.27 |

| Dextran Sample[a] | Viscosity (cPs) @ 14.11 rpm | Viscosity (cPs) @ 98.69 rpm | Viscosity (cPs) @ 162.1 rpm |
|---|---|---|---|
| Gtf 0768 (SEQ ID NO: 1) After PPT - 2 wt % (Example 2, 400 g/L sucrose reaction) | 49.89 | 23.61 | 18.32 |
| Gtf 0768 (SEQ ID NO: 1) After PPT - 2 wt % (Example 2, 800 g/L sucrose reaction) | 5.44 | 2.72 | 1.58 |

[a]Polymer samples are listed according to the respective enzyme used to synthesize the sample. Alternatively, dextran obtained from a commercial source was analyzed ("Commercial dextran").
[b]Measurement was outside the specification limits of the viscometer.

These data demonstrate that solutions of the dextran product of a glucosyltransferase comprising SEQ ID NO:1 can in most cases exhibit increased viscosity even after precipitation and resolvation, as compared to the viscosities of commercially obtained dextran and the dextran product of a commercially obtained dextran sucrase. This observation also appears to apply to the respective polymer products of glucosyltransferases comprising SEQ ID NO:5, 9, 13, or 17.

It is also noteworthy that, based on Tables 2-3, as the amount of sucrose in a gtf 0768 reaction is decreased from 800 g/L to 100 g/L, the viscosity of the dextran product appears to increase. Specifically, Table 3 indicates (at 14.11 rpm/2 wt % loading) viscosities of 5.44 cPs and 49.89 cPs for dextran products of reactions comprising 800 and 400 g/L sucrose, respectively, and Table 2 (gtf 0768, 2 wt % loading) may indicate a viscosity of about 957 cPs (exponential extrapolated at a rotation of 14.11 rpm) for dextran product of a reaction comprising 100 g/L sucrose. This result suggests that the viscosity of a dextran product can be controlled by modifying the level of sucrose initially provided to reaction.

Example 9

Further Production and Analysis of Dextran Synthesized by Gtf 0768

This Example is in addition to Example 2, describing another reaction comprising water, sucrose and gtf 0768. Also, this Example provides additional linkage and molecular weight analyses of the gelling product synthesized by gtf 0768, showing that this product is a type of dextran.

Reagents for Preparing Gtf Reaction:
  Sucrose (Sigma Prod. No. S-9378).
  Sodium phosphate buffer stock (1 M, pH 6.5, Teknova Cat No: S0276).
  Gtf 0768 enzyme solution (cell lysate as prepared in Example 1).

Gtf Reaction Conditions:

A 50-mL reaction was prepared containing 20 mM sodium phosphate buffer (buffer was diluted 50-fold with ddH2O from 1 M stock, pH 6.5), 100 g/L sucrose, and 0.1 mL of gtf 0768 enzyme solution. The reaction was shaken at 100 rpm in an incubator shaker (Innova, Model 4000) at 26° C. for 43 hours; the reaction became viscous after about 24 hours.

The gtf enzyme was deactivated by heating the reaction at 80° C. for 10 minutes. The deactivated viscous reaction was then mixed with 75 mL of 100% methanol to precipitate the viscous product. A white precipitate was formed. After carefully decanting the supernatant, the white precipitate was washed twice with 75 mL of 100% methanol. The solid product was dried at 45° C. under vacuum in an oven for 48 hours.

Samples (1 mL) of the reaction were taken at 0, 0.5, 1, 2, and 24 hours, respectively. The gtf enzyme was deactivated in each sample by heating at 80° C. for 10 minutes. Each sample was then diluted 10-fold with sterile water. 500 µL of diluted sample was transferred into a centrifuge tube filter (SPIN-X, 0.45-µm Nylon, 2.0 mL Polypropylene Tube, Costar #8170) and centrifuged at 12,000 rpm in a table centrifuge for 60 minutes, after which 200 µL of flowthrough was used for HPLC analysis to measure sucrose consumption during the reaction. The following HPLC conditions were applied for analyzing each sample: column (AMINEX HPX-87C carbohydrate column, 300×7.8 mm, Bio-Rad, No. 125-0095), eluent (water), flow rate (0.6 mL/min), temperature (85° C.), refractive index detector. HPLC analysis of the samples indicated substantial sucrose consumption during the 0768 gtf reaction.

HPLC was also used to analyze other products of the reaction. Polymer yield was back-calculated by subtracting the amount of all other saccharides left in the reaction from the amount of the starting sucrose. The back-calculated number was consistent with the viscous product dry weight analysis. Sucrose, leucrose, glucose and fructose were quantified by HPLC with an HPX-87C column (HPLC conditions as described above). DP2-7 oligosaccharides were quantified by HPLC with the following conditions: column (AMINEX HPX-42A carbohydrate column, 300×7.8 mm, Bio-Rad, No. 125-0097), eluent (water), flow rate (0.6 mL/min), temperature (85° C.), refractive index detector. These HPLC analyses indicated that the glucosyl-containing saccharide products of the 0768 gtf reaction consisted of 92.3% polymer product, 1.3% glucose, 5.0% leucrose, and 1.4% DP2-7 oligosaccharides.

A sample of dry dextran powder product (~0.2 g) of the above reaction was used for molecular weight analysis. Molecular weight was determined by a flow injection chromatographic method using an Alliance™ 2695 separation module from Waters Corporation (Milford, MA) coupled with three online detectors: a differential refractometer 2414 from Waters, a Heleos™_2 18-angle multiangle light scattering (MALS) photometer with quasielastic light scattering (QELS) detector from Wyatt Technologies (Santa Barbara, CA), and a ViscoStar™ differential capillary viscometer from Wyatt. The dry dextran powder was dissolved at 0.5 mg/mL in aqueous Tris (Tris[hydroxymethyl]aminomethane) buffer (0.075 M) containing 200 ppm $NaN_3$. The dissolution of dextran was achieved by shaking overnight at 50° C. Two AQUAGEL-OH GUARD columns from Agilent Technologies (Santa Clara, CA) were used to separate the dextran polymer peak from the injection peak. The mobile base for this procedure was the same as the dextran solvent, the flow rate was 0.2 mL/min, the injection volume was 0.1 mL, and the column temperature was 30° C. Empower™ version 3 software from Waters was used for data acquisition, and Astra™ version 6 software from Wyatt was used for multidetector data reduction. It was determined from this work that the dextran polymer product had a weight-average molecular weight (Mw) of $1.022$ $(+/-0.025) \times 10^8$ g/mol (i.e., roughly 100 million Daltons) (from MALS analysis), a z-average radius of gyration of 243.33 (+/−0.42) nm (from MALS analysis), and a z-average hydrodynamic radius of 215 nm (from QELS analysis). It was also determined from QELS analysis that the dextran has a standard deviation of particle size distribution (PSD) of about 0.259, indicating that the dextran likely is polydisperse in terms of hydrodynamic size.

For glycosidic linkage analysis purposes, a 50-mL gtf reaction was prepared as described above in this Example, except that the reaction time was 24 hours (reaction had become viscous). The gtf enzyme was deactivated by heating the reaction at 80° C. for 10 minutes. The deactivated viscous reaction was then placed into a regenerated cellulose sturdy dialysis tubing with a molecular weight cut-off (MWCO) of 12-14 kDa (Spectra/Por® 4 Dialysis Tubing, Part No. 132706, Spectrum Laboratories, Inc.) and dialyzed against 4 L of filter water at room temperature over one week. Water was exchanged every day during this dialysis. The dialyzed viscous reaction was then precipitated and dried as described above in this Example. About 0.2 g of dry powder was submitted for GC/MS linkage analysis.

Linkage analysis was performed according to methods described by Pettolino et al. (*Nature Protocols* 7:1590-1607), which is incorporated herein by reference. Briefly, a dry dextran sample was dissolved in dimethyl sulfoxide (DMSO) or 5% lithium chloride in DMSO, then all free hydroxyl groups were methylated by sequential addition of a sodium hydroxide/DMSO slurry followed by iodomethane. The methylated polymer was then extracted into methylene chloride and hydrolyzed to monomeric units using aqueous trifluoroacetic acid (TFA) at 120° C. The TFA was then evaporated from the sample and reductive ring opening was done using sodium borodeuteride, which also labeled the reducing end with a deuterium atom. The hydroxyl groups created by hydrolyzing the glycosidic linkages were then acetylated by treating with acetyl chloride and TFA at a temperature of 50° C. Finally, the derivatizing reagents were evaporated and the resulting methylated/acetylated monomers were reconstituted in acetonitrile and analyzed by gas chromatography with mass spectrometry (GC/MS) using a biscyanopropyl cyanopropylphenyl polysiloxane column. The relative positioning of the methyl and acetyl functionalities, along with the deuterium label, yielded species that have distinctive retention time indices and mass spectra that can be compared to published databases. In this way, the derivatives of the monomeric units indicated how each monomer was originally linked in the dextran polymer and whether the monomer was a branch point. The results of analyzing these samples (dextran initially dissolved in DMSO or DMSO/5% LiCl) are provided in Table 4.

TABLE 4

Linkage Profile of Gtf 0768 Dextran Product

| | Wt %/Mol % of Glucose Monomers in Dextran | | | | |
|---|---|---|---|---|---|
| Sample | 3-glc [a] | 6-glc [b] | 4-glc [c] | 3,6-glc [d] | 2,6- + 4,6-glc [e] |
| DMSO | 0.4 | 90.2 | 0.4 | 8.3 | 0.7 |
| DMSO/5% LiCl | 0.9 | 89.3 | 0.4 | 8.0 | 1.4 |

[a] Glucose monomer linked at carbon positions 1 and 3.
[b] Glucose monomer linked at carbon positions 1 and 6.
[c] Glucose monomer linked at carbon positions 1 and 4.
[d] Glucose monomer linked at carbon positions 1, 3 and 6.
[e] Glucose monomer linked at carbon positions 1, 2 and 6, or 1, 4 and 6.

In general, the results in Table 4 indicate that the dextran product analyzed above comprises:
(i) about 87-93 wt % glucose linked only at positions 1 and 6;
(ii) about 0.1-1.2 wt % glucose linked only at positions 1 and 3;
(iii) about 0.1-0.7 wt % glucose linked only at positions 1 and 4;
(iv) about 7.7-8.6 wt % glucose linked only at positions 1, 3 and 6; and
(v) about 0.4-1.7 wt % glucose linked only at (a) positions 1, 2 and 6, or (b) positions 1, 4 and 6.

Based on this information and some other studies (data not shown), it is contemplated that this product is a branched structure in which there are long chains (containing mostly or all alpha-1,6-linkages) of about 20 DP in length (average) that iteratively branch from each other (e.g., a long chain can be a branch from another long chain, which in turn can itself be a branch from another long chain, and so on). The branched structure also appears to comprise short branches from the long chains; these short chains are believed to be 1-3 DP in length and mostly comprise alpha-1,3 and -1,4 linkages, for example. Branch points in the dextran, whether from a long chain branching from another long chain, or a short chain branching from a long chain, appear to comprise alpha-1,3, -1,4, or -1,2 linkages off of a glucose involved in alpha-1,6 linkage. Roughly 25% of all the branch points of the dextran branched into a long chain.

Thus, reactions comprising water, sucrose and an enzyme comprising SEQ ID NO:1 synthesized a very large gelling dextran product, as determined by the product's high Mw and predominant alpha-1,6 glucosidic linkage profile.

Example 10

Formulation Comprising Dextran Synthesized by Gtf 0768

This Example discloses a formulation comprising the dextran product of gtf 0768. This formulation was shown to have better sensory characteristics (or "feel") compared to formulations comprising certain compounds (xanthan gum, Carbopol®) commonly used for providing viscosity to certain consumer products (e.g., personal care compositions such as lotion).

Three different emulsions were prepared and compared against each other in a skinfeel study, as follows.

Dextran-Based Emulsion: Dextran was produced using gtf 0768 (comprising SEQ ID NO:1) in a reaction similar to the reaction disclosed in Example 9. At room temperature, polysorbate 80, sorbitan monooleate and mineral oil (Phase B, Table 5) were combined in a small vessel, and mixed by hand until homogeneous. Phase B was slowly added to water (Phase A, Table 5) under moderate propeller mixing. The mixture was homogenized at 5000-9000 rpm for approximately 5-10 minutes. Dextran (Phase C, Table 5) was then added under moderate propeller mixing. Germaben® II (Phase D, Table 5) was then added as a preservative under moderate propeller mixing. The dextran could optionally have been pre-hydrated using a portion of the water from phase A.

TABLE 5

Dextran-Based Emulsion

| Ingredients | % Activity | wt % (Desired) | wt % (Neat) | Grams |
|---|---|---|---|---|
| Phase A | | | | |
| Water (deionized) | | | 73.50 | 73.50 |
| Phase B | | | | |
| Polysorbate 80 | 100.00 | 2.43 | 2.43 | 2.43 |
| Sorbitan Monooleate | 100.00 | 2.57 | 2.57 | 2.57 |
| Mineral Oil | 100.00 | 20.00 | 20.00 | 20.00 |
| Phase C | | | | |
| Dextran | 100.00 | 1.00 | 1.00 | 1.00 |
| Phase D | | | | |
| Germaben ® II | 100.00 | 0.50 | 0.50 | 0.50 |
| | | | 100.00 | 100.00 |

Xanthan Gum-Based Emulsion (Control 1): At room temperature, xanthan gum and water (Phase A, Table 6) were combined under moderate propeller mixing until homogeneous. Polysorbate 80, sorbitan monooleate and mineral oil (Phase B, Table 6) were combined in a small vessel, and mixed by hand until homogeneous. Phase B was slowly added to Phase A under moderate propeller mixing. The mixture was homogenized at 5000-9000 rpm for approximately 5-10 minutes. Germaben® II (Phase C, Table 6) was then added as a preservative under moderate propeller mixing.

TABLE 6

Xanthan Gum-Based Emulsion

| Ingredients | % Activity | wt % (Desired) | wt % (Neat) | Grams |
|---|---|---|---|---|
| Phase A | | | | |
| Water (deionized) | | | 74.00 | 74.00 |
| Xanthan Gum | 100.00 | 0.50 | 0.50 | 0.50 |
| Phase B | | | | |
| Polysorbate 80 | 100.00 | 2.43 | 2.43 | 2.43 |
| Sorbitan Monooleate | 100.00 | 2.57 | 2.57 | 2.57 |
| Mineral Oil | 100.00 | 20.00 | 20.00 | 20.00 |
| Phase C | | | | |
| Germaben ® II | 100.00 | 0.50 | 0.50 | 0.50 |
| | | | 100.00 | 100.00 |

Carbopol® Ultrez 10-Based Emulsion (Control 2): At room temperature, Carbopol® Ultrez 10 and water (Phase A, Table 7) were combined under moderate propeller mixing until homogeneous. Polysorbate 80, sorbitan monooleate and mineral oil (Phase B, Table 7) were combined in a small vessel, and mixed by hand until homogeneous. Phase B was slowly added to Phase A under moderate propeller mixing. The mixture was homogenized at 5000-9000 rpm for approximately 5-10 minutes. Germaben® II (Phase C, Table 7) was then added as a preservative under moderate propeller mixing. A 20-wt % solution of sodium hydroxide was used to neutralize the emulsion to pH 5.5.

TABLE 7

Carbopol ® Ultrez 10-Based Emulsion

| Ingredients | % Activity | wt % (Desired) | wt % (Neat) | Grams |
|---|---|---|---|---|
| Phase A | | | | |
| Water (deionized) | | | 74.00 | 74.00 |
| Carbopol ® Ultrez 10 | 100.00 | 0.50 | 0.50 | 0.50 |
| Phase B | | | | |
| Polysorbate 80 | 100.00 | 2.43 | 2.43 | 2.43 |
| Sorbitan Monooleate | 100.00 | 2.57 | 2.57 | 2.57 |
| Mineral Oil | 100.00 | 20.00 | 20.00 | 20.00 |
| Phase C | | | | |
| Germaben ® II | 100.00 | 0.50 | 0.50 | 0.50 |
| | | | 100.00 | 100.00 |

Skinfeel Analysis and Results: A double-blind, skinfeel analysis was performed according to ASTM E1490-3 ("Standard Practice for Descriptive Skinfeel Analysis of Creams and Lotions", ASTM International, West Conshohocken, PA, 2003, DOI: 10.1520/E1490-03, incorporated herein by reference) to compare each of the above emulsions. The primary attributes evaluated in this study were rub-out sliminess, afterfeel stickiness, pick-up stringiness and pick-up stickiness. Panelists assessed attributes on a scale from 1-5, where 1 exhibits the least of the attribute and 5 exhibits the most of the attribute. The results are reported in Table 8 below as an average value of the panelists' ratings for each attribute. The sum average of these values (Σ, Table 8) indicates that the overall sensory experience for emulsions (e.g., lotions) produced with dextran as presently disclosed exceeds the results of similar emulsions produced with either xanthan gum or Carbopol® Ultrez 10.

TABLE 8

Carbopol ® Ultrez 10-Based Emulsion

| | Average Rating | | |
|---|---|---|---|
| Skinfeel Attribute | Dextran | Xanthan Gum | Carbopol ® Ultrez 10 |
| Rub-Out Sliminess | 2 | 3 | 2 |
| Afterfeel Stickiness | 2 | 2 | 3 |
| Pick-Up Stringiness | 1 | 3 | 3 |
| Pick-Up Stickiness | 2 | 3 | 2 |
| Σ | 7 | 11 | 10 |

It is noteworthy that the dextran-containing emulsion scored better than the control emulsions in the skinfeel analysis, especially since there was two-times the amount of dextran (1 wt %) in the emulsion compared to the amount of xanthan gum (0.5 wt %) or Carbopol® Ultrez 10 (0.5 wt %) in the control emulsions.

Thus, dextran produced by gtf 0768 (comprising SEQ ID NO:1) can be suitable for use in compositions where enhanced sensory characteristics are desirable, such as in personal care and food products, for example.

Example 11

Dextran-Comprising Cleanser with Suspended Particles

This Example discloses a cleanser comprising the dextran product of gtf 0768. Jojoba ester beads could be suspended in this composition, indicating that the dextran can function as a dispersant.

Dextran was produced using gtf 0768 (comprising SEQ ID NO:1) in a reaction similar to the reaction disclosed in Example 9. At room temperature water, dextran, glycerin, polysorbate 20, cocamidopropyl betaine, PPG-2 hydroxyethyl cocamide and disodium EDTA were combined according to the formulation in Table 9, and mixed by hand until homogeneous. Jojoba beads were then added and mixing was continued until the beads were homogeneously dispersed. The dextran could optionally have been pre-hydrated using a portion of the water component.

TABLE 9

Dextran-Based Jojoba Bead Suspension

| Ingredient | % Activity | wt % (Desired) | wt % (Neat) | Grams |
|---|---|---|---|---|
| Water (deionized) | | | 22.95 | 22.95 |
| Dextran | 100 | 5 | 5 | 5 |
| Glycerin | 100 | 10 | 10 | 10 |
| Polysorbate 20 | 100 | 5.25 | 5.25 | 5.25 |
| Cocamidopropyl Betaine | 35.97 | 20 | 55.6 | 55.6 |
| PPG-2 Hydroxyethyl Cocamide | 100 | 1 | 1 | 1 |
| Disodium EDTA | 100 | 0.1 | 0.1 | 0.1 |
| Jojoba Ester Beads | 100 | 0.1 | 0.1 | 0.1 |
| | | | 100 | 100 |

Thus, dextran produced by gtf 0768 (comprising SEQ ID NO:1) can be used as a dispersant in aqueous compositions such as certain personal care products.

What is claimed is:

1. An isolated composition comprising water, sucrose and a glucosyltransferase enzyme comprising an amino acid sequence that is at least 98% identical to SEQ ID NO:1 or SEQ ID NO:2.

2. The isolated composition of claim 1, wherein the glucosyltransferase enzyme comprises the amino acid sequence that is at least 98% identical to SEQ ID NO:1.

3. The isolated composition of claim 1, wherein the glucosyltransferase enzyme comprises an amino acid sequence that is at least 99% identical to SEQ ID NO:1.

4. The isolated composition of claim 1, wherein the glucosyltransferase enzyme comprises the amino acid sequence of SEQ ID NO:1.

5. The isolated composition of claim 1, wherein the glucosyltransferase enzyme comprises the amino acid sequence that is at least 98% identical to SEQ ID NO:2.

6. The isolated composition of claim 1, wherein the glucosyltransferase enzyme comprises an amino acid sequence that is at least 99% identical to SEQ ID NO:2.

7. The isolated composition of claim 1, wherein the glucosyltransferase enzyme comprises the amino acid sequence of SEQ ID NO:2.

8. The isolated composition of claim 1, comprised within an inert vessel.

9. The isolated composition of claim 8, comprised within a stainless steel vessel, plastic vessel, or glass vessel.

10. The isolated composition of claim 1, wherein the isolated composition comprises only one type of glucosyltransferase enzyme.

11. The isolated composition of claim 1, wherein the isolated composition is cell-free.

12. The isolated composition of claim 1, wherein the isolated composition is a food product.

13. The isolated composition of claim 2, wherein the isolated composition is a food product.

14. The isolated composition of claim 3, wherein the isolated composition is a food product.

15. The isolated composition of claim 4, wherein the isolated composition is a food product.

16. The isolated composition of claim 12, wherein the food product is a cultured dairy product.

17. The isolated composition of claim 16, wherein the cultured dairy product is cottage cheese or cheese.

18. The isolated composition of claim 16, wherein the cultured dairy product is sour cream.

19. The isolated composition of claim 16, wherein the cultured dairy product is yogurt.

20. The isolated composition of claim 12, wherein the food product is a frozen dessert or ice cream.

* * * * *

UNITED STATES PATENT AND TRADEMARK OFFICE
CERTIFICATE OF CORRECTION

| | | |
|---|---|---|
| PATENT NO. | : 12,173,091 B2 | Page 1 of 1 |
| APPLICATION NO. | : 17/865904 | |
| DATED | : December 24, 2024 | |
| INVENTOR(S) | : Rakesh Nambiar et al. | |

It is certified that error appears in the above-identified patent and that said Letters Patent is hereby corrected as shown below:

In the Specification

Column 1, Lines 4-12 should read:
This application is a continuation of U.S. application Ser. No. 16/111,514 (filed Aug. 24, 2018, now U.S. Patent No. 11390692), which is a continuation of U.S. application Ser. No. 14/933,128 (filed Nov. 5, 2015, now U.S. Patent No. 10059779), which claims the benefit of U.S. Provisional Application No. 62/075,460 (filed Nov. 5, 2014), all of which prior applications are incorporated herein by reference in their entirety.

Signed and Sealed this
Fifteenth Day of April, 2025

Coke Morgan Stewart
*Acting Director of the United States Patent and Trademark Office*

SEQUENCE LISTING

```
Sequence total quantity: 18
SEQ ID NO: 1              moltype = AA  length = 1447
FEATURE                   Location/Qualifiers
REGION                    1..1447
                          note = MISC_FEATURE - mature 0768 gtf
source                    1..1447
                          mol_type = protein
                          organism = Leuconostoc pseudomesenteroides
SEQUENCE: 1
DQNVNDPSVA TTTQNVVTDQ DTSIDASVAT TVNPNLDDTQ ADNTNIQTPT DQNDESKDTT    60
PKVETGDTTN SQSTEAQETT AQTNNDVETP QNSDAAIETG LLTTNNQIRY VNPDGTVLTG   120
AYKTINGNTY YFDDDSGVAL VGLHKIGDTL KGFSLNGVQV KGDYLTAANG DKYYFDSNGN   180
AVSGVQQING KTYYFDSTGK LMKGYTAVLN GVVTFFNSTT GEADNTDAST IKTGVTIDNS   240
DYTVHNAAYD NTAASFDNIN GYLTAESWYR PKEILENGES WRPSTAEDKR PILITWQPDI   300
VTEVNYLNMM AANGLLSINA PFTTASDLAI MNDAVRAVQK NIEMRISQEK STDWLKALMT   360
QFINTQPQWN EVSESPSNDH LQGGALTYVN SPLTPDANSN FRLLNRTPTN QSGTTRYDTD   420
KSKGGFELLL ANDVDNSNPV VQAEQLNWLY YLMNFGSITA NDPTANFDGI RVDAVDNVDA   480
DLLQIASDYF KLAYGTSLSD TNANQHLSIL EDWSANDAEY MSKTGSNQLT MDTYTQQQLL   540
FSLTKQVGNR ADMRRFLEYF MINRANDSTE NVATPNYSFV RAHDSEVQTV IATIIKDLHP   600
DVVNSLAPTQ AQLEEAFAVY NADMNRVDKQ YTQYNMPSAY AMLLTNKDTI PRVYYGDLYT   660
DDGEYMGTQT PYYDAIVNLL QSRVKYVAGG QSMAVDQHDI LTSVRYGKNL ADANATSDDL   720
TSINSGIGVI VSNNPNLSLA SGETVVLHMG IAHANQVYRE ILETTDNGIA NNTDIFKTTD   780
SNGDLIFTAS EIHGYSNVQV SGFLSVWAPK DATDDQDVRT AASESTSNDG NTLHSNAALD   840
SNLIYEGFSN FQSTPQSESE FANVKIAANV NLFKSWGVTS FQMAPQYRSS TDTSFLDSII   900
QNGYAFTDRY DLGFETPTKY GTDQQLRDAI KALHANGIQA MADFVPDQIY NLPQTELVSV   960
SRTDSLGNQS ANSNAANVLY VSHTVGGGEY QSKYGGEFLA IIKSKYPSLF KTIQVSTGLP  1020
IDDSTKIKEW SAKYFNGSNI QGRGFGYVLS DGGTQNYFKV ISNSTDDDFL PNQLTGKPTM  1080
TGFEQTSKGI VYYSKSGIQA KNQFVKDDVS GNYYYFNKNG LMTVGSKTIN GKNYMFLPNG  1140
VELRGSFLQT ADGTVNYYAT NGAQVQDSYV TDTEGNSYYF DGDGEMVTGT YTVDGHAQYF  1200
DVNGVQTKGA IITLGGVQRY YQAGNGNLAT NQYVSYNNSW YYANTKGELV TGVQSINGNV  1260
QYFASNGQQI KGQIVVTGNQ KSYYDANTGN LIKNDFLTPD QGKTWYYADQ DGNLVVGAQE  1320
VNGHKLYFDD NGIQIKDQII SNDGQQYYYQ GGNGDLVTNR YISYNDSWYY ADATGVLVTG  1380
QQIINGETQY FRTDGRQVKG QIIADGDKQH YYDADSGNLV KNNFVTVDQG KTWYYADQDG  1440
NLSLVDR                                                           1447

SEQ ID NO: 2              moltype = AA  length = 1457
FEATURE                   Location/Qualifiers
REGION                    1..1457
                          note = 0768 gtf mature protein with start codon and other
                           added sequences
source                    1..1457
                          mol_type = protein
                          organism = synthetic construct
SEQUENCE: 2
MASADQNVND PSVATTTQNV VTDQDTSIDA SVATTVNPNL DDTQADNTNI QTPTDQNDES    60
KDTTPKVETG DTTNSQSTEA QETTAQTNND VETPQNSDAA IETGLLTTNN QIRYVNPDGT   120
VLTGAYKTIN GNTYYFDDDS GVALVGLHKI GDTLKGFSLN GVQVKGDYLT AANGDKYYFD   180
SNGNAVSGVQ QINGKTYYFD STGKLMKGYT AVLNGVVTFF NSTTGEADNT DASTIKTGVT   240
IDNSDYTVHN AAYDNTAASF DNINGYLTAE SWYRPKEILE NGESWRPSTA EDKRPILITW   300
QPDIVTEVNY LNMMAANGLL SINAPFTTAS DLAIMNDAVR AVQKNIEMRI SQEKSTDWLK   360
ALMTQFINTQ PQWNEVSESP SNDHLQGGAL TYVNSPLTPD ANSNFRLLNR TPTNQSGTTR   420
YDTDKSKGGF ELLLANDVDN SNPVVQAEQL NWLYYLMNFG SITANDPTAN FDGIRVDAVD   480
NVDADLLQIA SDYFKLAYGT SLSDTNANQH LSILEDWSAN DAEYMSKTGS NQLTMDTYTQ   540
QQLLFSLTKQ VGNRADMRRF LEYFMINRAN DSTENVATPN YSFVRAHDSE VQTVIATIIK   600
DLHPDVVNSL APTQAQLEEA FAVYNADMNR VDKQYTQYNM PSAYAMLLTN KDTIPRVYYG   660
DLYTDDGEYM GTQTPYYDAI VNLLQSRVKY VAGGQSMAVD QHDILTSVRY GKNLADANAT   720
SDDLTSINSG IGVIVSNNPN LSLASGETVV LHMGIAHANQ VYREILETTD NGIANNTDIF   780
KTTDSNGDLI FTASEIHGYS NVQVSGFLSV WAPKDATDDQ DVRTAASEST SNDGNTLHSN   840
AALDSNLIYE GFSNFQSTPQ SESEFANVKI AANVNLFKSW GVTSFQMAPQ YRSSTDTSFL   900
DSIIQNGYAF TDRYDLGFET PTKYGTDQQL RDAIKALHAN GIQAMADFVP DQIYNLPQTE   960
LVSVSRTDSL GNQSANSNAA NVLYVSHTVG GGEYQSKYGG EFLAIIKSKY PSLFKTIQVS  1020
TGLPIDDSTK IKEWSAKYFN GSNIQGRGFG YVLSDGGTQN YFKVISNSTD DDFLPNQLTG  1080
KPTMTGFEQT SKGIVYYSKS GIQAKNQFVK DDVSGNYYYF NKNGLMTVGS KTINGKNYMF  1140
LPNGVELRGS FLQTADGTVN YYATNGAQVQ DSYVTDTEGN SYYFDGDGEM VTGTYTVDGH  1200
AQYFDVNGVQ TKGAIITLGG VQRYYQAGNG NLATNQYVSY NNSWYYANTK GELVTGVQSI  1260
NGNVQYFASN GQQIKGQIVV TGNQKSYYDA NTGNLIKNDF LTPDQGKTWY YADQDGNLVV  1320
GAQEVNGHKL YFDDNGIQIK DQIISNDGQQ YYYQGGNGDL VTNRYISYND SWYYADATGV  1380
LVTGQQIING ETQYFRTDGR QVKGQIIADG DKQHYYDADS GNLVKNNFVT VDQGKTWYYA  1440
DQDGNLSLVD RHHHHHH                                                1457

SEQ ID NO: 3              moltype = DNA  length = 4347
FEATURE                   Location/Qualifiers
source                    1..4347
                          mol_type = unassigned DNA
                          organism = Weissella cibaria
SEQUENCE: 3
atgtacaagt ccggaaagtt ttgggtagct gccggtgctt tgtttgttgg gctggcattc    60
gctggtaaca cgcaggctga tactgtatta ccaagtgaac aacgtgcaac ggagacgaca   120
```

```
cagacgacac agaccagtga agacacgtcc gccactaaga cgccggcatc ggcgtcgact    180
tcaagctcag tcaatgttga cacgagtgac ctgcctgaca gttcaagtac ggtagttgat    240
agtacaagtg caagtgcaag cgtagtgagt gatagcgtcg ctgtgccaga tactggatca    300
caatttacga gttcgtcagg gtcaatgtca tcatcatttg ttaagtcatc actagcggca    360
acaactagtg atgcttctgg cagtcagtcg gcggcggtca ctagcgcaac cgttagttcg    420
gtggccacga gtagttcagc atcttcagtg acaacagcca caagcgaatc agcagtgata    480
agcagcgccg tgtcagatgg ttaccatgat gaaggtggtg attgggtcta ttatcgagct    540
ggaaaaaagt tagtcggtcg acaaacgatt gatacgtttg cggtttactt tgacgccgat    600
gcaaacaag tcaagggtga ttggcgtgaa agtgatggta accgtgcgta ttatgatgga    660
caagaaggac gagcattaac gcaaacgcaa gcagtcaatg gcgttatcta cggttttaat    720
caaagcggct atcaaatcaa gaatgatttc ggccaaacag cgaatcgaga tacgtattat    780
ttcgacgcac aaggtcatgt tgtcacggga atccaaacaa ttgcaaacaa ggtttatgat    840
tttgatgagc aaggtcgaat gctgaaaggc attgccacgt cagttgatga caagatgatg    900
tattttgatg atcaaacagg tgttgacaaa ccggctgatc atcctgaatt caaccctgaa    960
acggaaccgg ttcctgacga caatatcaaa cataatgcag cacatggtac gacaccagca   1020
gattttgatt cgatggctgg ctacctgacg gctgatactt ggtatcgccc aaccgatatt   1080
ttggaaaatg gtgagacgtg gcgcgaatcg caaccaactg aatttcgacc actgttagca   1140
acttggtggc caacaaaaca aactcaggcc gattacgtga actacatgaa tcacgcatta   1200
gatatgtcaa atgcaagtgt gtcagctgcc gattcagaag ccacgctaac tgcggcaacc   1260
gatgctattc aagcggccgt tgagcaccaa attacggtgc gccaatcaac ggcctggtta   1320
cgtgaattaa tggccgcgtt tgttgtgaca cagccacagt ggaataaaac cagtgaagat   1380
gttaatgatg atcatttgca aggtggggcg ctaacatttg agaataacgg cgacacagac   1440
gctaattcgg attatcgcct catgaatcgc acgccaacaa atcagactgg tgaacgcttg   1500
tatcacattg atgactcgct tggcggttac gaattattgc tggcaaatga cgttgacaat   1560
tcaaatccac aagttcaggc agaacaattg aattggttgt actacttgat gcattttggg   1620
gatattacgg tcgatgatcc ggatgcaaat tttgatgcca tacggattga tgcgtgcaga   1680
aatgtcgatg ctgatttact tcaactagca gctcagtatt tccgtgatgc ctatggcatg   1740
gccacgactg acgcgacatc aaataagcat ctttcaatac ttgaggattg gagccataac   1800
gatccggcgt atatgcaagc acacggcaat gatcaattaa cgatggatga ttatatgcac   1860
acacagttga tttggtcatt aaccaagcca gaggcacaac gtggcaccat ggcacgcttt   1920
atggacttct atctccaccaa ccgtgctaat gatgatacag aaaacacggc gcaacctagt   1980
tactcgtttg tgcgtgccca tgatagcgaa gtgcaaacag tcattgctga aatcgtgacg   2040
aagctacatc cagaagcagg aaacgggtta atgcctacgg aagaacaaat ggcagaagcg   2100
tttaagattt acaatgcgga ccaaaagaag gccgttaaca cttacacga ctacaatatg   2160
ccatctgcat acgccatgct gttaacgaac aaggatgtta ttccacgaat ttactatgct   2220
gacttgtaca ctgacgatgg gcaattcatg cgacaaaat cacccctattt tgatgcgatt   2280
tcggctatgt tacaagcgcg cacgaagtat gtagctggtg acaaacgat ggcggttgac   2340
cagcacgacg tcttgactag cgttcggttt ggtaaggtg ccatgacggc cagtgattta   2400
ggaaatgctg agactcggac tgagggtgtg ggattaatta ttagcaacaa cccaaagttg   2460
caattgggac aacaagataa cgtggtgtta cacatgggac ttgcgcacgc gaatcaagca   2520
ttccgagcag ttgtactaac gaccgcgacc ggattaacca tttataatga cgatgatgct   2580
ccaattcgtt ataccgataa taagggtgat ttaattttca ataaccatga cgtatatggc   2640
gtgttgaatc cacaagtgtc aggcttcttg gcaatgtggg tgcaactgg tgcaccagcg   2700
aaccaggatg cgcgatctac tgcgtcaacc aacagttcaa cggatggatc tgcctaccat   2760
tctaatgcgg ctttagatag tcaagtcatc tttgaatcat tttcgaattt ccaggctatg   2820
ccaacaagcc atgacacgta caccaacgtt gtgttagcca atcatgctga ccagttcac    2880
gattgggaa taacttcggt acagttagcg ccacaatacc ggtcttcaac cgacggaacc   2940
tttttggatg cgattattca aaatggctat gccttcactg accgttatga tttagggttt   3000
ggtacgccaa ctaagtatgg ggatgatacg gatttgcgga acgtcatcaa agcattgcat   3060
gcaaatggca tgcaagtaat ggctgatttt gtgccggatc aattgtatac attaccaggt   3120
aaggaattgg tacaagtcac ccgaacaaac aatatggtga agccagatac acactccgat   3180
atccaacata ttttatatgt gacgagcact cggggtggcg gtgagtatca gaaacagtac   3240
ggtggtgagt tccttgagcg gttacgtgcg ctctaccctg atttatttac gacacgtcaa   3300
atttcaaccg gacaaaccat tgatgattca gtaaaaatta agaatggtc agctaagtat   3360
ttgaatggta ccgcaattca aggccgtgga gctggctatg tgctacgtga taatggtaca   3420
aatgcttatt acaaggtgac ggcaaatgac ggtaatgtga acttaccaaa gcaattactc   3480
ggacaaccag tgatgaccgg attctatcac gaggcagatg gttatcatt tgaaacattg   3540
agtggtacgt cggccaaaga tgccttcatt atgggtgacg atggggcgct gtattatttc   3600
gatgatcagg gcgtcatggt aacgggtaag caactcgtgc accaagacca tgatttcttc   3660
ctaccaaacg gtattgctct gacggatgcg tttgtacaaa gtgcggatgg tcaacgtcag   3720
tactatgata aaacaggtcg cctggtcatt aatcaatatg tgactgacca ccaagcaaat   3780
gcgttccggg ttgatgcaga cggtaacgtt gttcgtaacc aagctttgac tgttgacggc   3840
catgaacaat atttcggcac aaacggtgtc caagcgaaaa cagtgctcat tcgaactgac   3900
gataatcaca cacggtacta cgaagccaat agtggtaatc tcgtgaagca acagttttatt   3960
cttgatacag atggacattg gttgtacgcc gatgctgcag gagacttggc acgcggacaa   4020
attacggttg gccaagacac gttgtatttt gatgataata atcatcaggt aaaagatgat   4080
tttgtctatg atactaacgg tgtgcattat tttaatggca caacaggcgc tgaaatcaaa   4140
caagattacg cgtttcttga tggcaaatgg tactatttg atgatttggg acgaatggta   4200
accggtttgc agcgtattaa tggtgagtat cgctattttg atgctaatgg tgtgcaacta   4260
aagggtggta ccgtgaccga tccactaacg caccaaacgt cacttttga tgcgcaaact   4320
ggtgttggta cgttggtgac gttttaa                                       4347
```

SEQ ID NO: 4        moltype = AA  length = 1448
FEATURE              Location/Qualifiers
source              1..1448
                    mol_type = protein
                    organism = Weissella cibaria
SEQUENCE: 4
MYKSGKFWVA AGALFVGLAF AGNTQADTVL PSEQRATETT QTTQTSEDTS ATKTPASAST    60

```
SSSVNVDTSD   LPDSSSTVVD   STSASASVVS   DSVAVPDTGS   QFTSSSGSMS   SSFVKSSLAA    120
TTSDASGSQS   AAVTSATVSS   VATSSSASSV   TTATSESAVI   SSAVSDGYHD   EGGDWVYYRA    180
GKKLVGRQTI   DTFAVYFDAD   GKQVKGDWRE   SDGNRAYYDG   QEGRALTQTQ   AVNGVIYGFN    240
QSGYQIKNDF   GQTANRDTYY   FDAQGHVVTG   IQTIANKVYD   FDEQGRMLKG   IATSVDDKMM    300
YFDDQTGVGQ   PADHPEFNPE   TEPVPDDNIK   HNAAHGTTPA   DFDSMAGYLT   ADTWYRPTDI    360
LENGETWRES   QPTEFRPLLA   TWWPTKQTQA   DYVNYMNHAL   DMSNASVSAA   DSEATLTAAT    420
DAIQAAVEHQ   ITVRQSTAWL   RELMAAFVVT   QPQWNKTSED   VNDDHLQGGA   LTFENNGDTD    480
ANSDYRLMNR   TPTNQTGERL   YHIDDSLGGY   ELLLANDVDN   SNPQVQAEQL   NWLYYLMHFG    540
DITADDPDAN   FDAIRIDAVD   NVDADLLQLA   AQYFRDAYGM   ATTDATSNKH   LSILEDWSHN    600
DPAYMQAHGN   DQLTMDDYMH   TQLIWSLTKP   EAQRGTMARF   MDFYLTNRAN   DDTENTAQPS    660
YSFVRAHDSE   VQTVIAEIVT   KLHPEAGNGL   MPTEEQMAEA   FKIYNADQKK   AVKTYTHYNM    720
PSAYAMLLTN   KDVIPRIYYG   DLYTDDGQFM   ATKSPYFDAI   SAMLQARTKY   VAGGQTMAVD    780
QHDVLTSVRF   GKGAMTASDL   GNAETRTEGV   GLIISNNPKL   QLGQQDNVVL   HMGLAHANQA    840
FRAVVLTTAT   GLTIYNDDDA   PIRYTDNKGD   LIFNNHDVYG   VLNPQVSGFL   AMWVPTGAPA    900
NQDARSTAST   NSSTDGSAYH   SNAALDSQVI   FESFSNFQAM   PTSHDTYTNV   VLANHADQLH    960
DWGITSVQLA   PQYRSSTDGT   FLDAIIQNGY   AFTDRYDLGF   GTPTKYGDDT   DLRNVIKALH   1020
ANGMQVMADF   VPDQLYTLPG   KELVQVTRTN   NMGEPDTHSD   IQHILYVTST   RGGGEYQKQY   1080
GGEFLERLRA   LYPDLFTTRQ   ISTGQTIDDS   VKIKEWSAKY   LNGTAIQGRG   AGYVLRDNGT   1140
NAYYKVTAND   GNVNLPKQLL   GQPVMTGFYH   EADGYHFETL   SGTSAKDAFI   MGDDGALYYF   1200
DDQGVMVTGK   QRVHQDQYFF   LPNGIALTDA   FVQSADGQRQ   YYDKTGRLVI   NQYVTDHQAN   1260
AFRVDADGNV   VRNQALTVDG   HEQYFGTNGV   QAKAVLIRTD   DNQARYYEAN   SGNLVKQQFI   1320
LDTDGHWLYA   DAAGDLARGQ   ITVGQDTLYF   DDNNHQVKDD   FVYDTNGVHY   FNGTTGAEIK   1380
QDYAFHDGKW   YYFDDLGRMV   TGLQRINGEY   RYFDANGVQL   KGGTVTDPLT   HQTYTFDAQT   1440
GVGTLVTF                                                                     1448

SEQ ID NO: 5            moltype = AA   length = 1422
FEATURE                 Location/Qualifiers
REGION                  1..1422
                        note = MISC_FEATURE - mature 2919 gtf
source                  1..1422
                        mol_type = protein
                        organism = Weissella cibaria
SEQUENCE: 5
DTVLPSEQRA   TETTQTTQTS   EDTSATKTPA   SASTSSSVNV   DTSDLPDSSS   TVVDSTSASA    60
SVVSDSVAVP   DTGSQFTSSS   GSMSSSFVKS   SLAATTSDAS   GSQSAAVTSA   TVSSVATSSS   120
ASSVTTATSE   SAVISSAVSD   GYHDEGGDWV   YYRAGKKLVG   RQTIDTFAVY   FDADGKQVKG   180
DWRESDGNRA   YYDGQEGRAL   TQTQAVNGVI   YGFNQSGYQI   KNDFGQTANR   DTYYFDAQGH   240
VVTGIQTIAN   KVYDFDEQGR   MLKGIATSVD   DKMMYFDDQT   GVGQPADHPE   FNPETEPVPD   300
DNIKHNAAHG   TTPADFDSMA   GYLTADTWYR   PTDILENGET   WRESQPTEFR   PLLATWWPTK   360
QTQADYVNYM   NHALDMSNAS   VSAADSEATL   TAATDAIQAA   VEHQITVRQS   TAWLRELMAA   420
FVVTQPQWNK   TSEDVNDDHL   QGGALTFENN   GDTDANSDYR   LMNRTPTNQT   GERLYHIDDS   480
LGGYELLLAN   DVDNSNPQVQ   AEQLNWLYYL   MHFGDITADD   PDANFDAIRI   DAVDNVDADL   540
LQLAAQYFRD   AYGMATTDAT   SNKHLSILED   WSHNDPAYMQ   AHGNDQLTMD   DYMHTQLIWS   600
LTKPEAQRGT   MARFMDFYLT   NRANDDTENT   AQPSYSFVRA   HDSEVQTVIA   EIVTKLHPEA   660
GNGLMPTEEQ   MAEAFKIYNA   DQKKAVKTYT   HYNMPSAYAM   LLTNKDVIPR   IYYGDLYTDD   720
GQFMATKSPY   FDAISAMLQA   RTKYVAGGQT   MAVDQHDVLT   SVRFGKGAMT   ASDLGNAETR   780
TEGVGLIISN   NPKLQLGQQD   NVVLHMGLAH   ANQAFRAVVL   TTATGLTIYN   DDDAPIRYTD   840
NKGDLIFNNH   DVYGVLNPQV   SGFLAMWVPT   GAPANQDARS   TASTNSSTDG   SAYHSNAALD   900
SQVIFESFSN   FQAMPTSHDT   YTNVVLANHA   DQLHDWGITS   VQLAPQYRSS   TDGTFLDAII   960
QNGYAFTDRY   DLGFGTPTKY   GDDTDLRNVI   KALHANGMQV   MADFVPDQLY   TLPGKELVQV  1020
TRTNNMGEPD   THSDIQHILY   VTSTRGGGEY   QKQYGGEFLE   RLRALYPDLF   TTRQISTGQT  1080
IDDSVKIKEW   SAKYLNGTAI   QGRGAGYVLR   DNGTNAYYKV   TANDGNVNLP   KQLLGQPVMT  1140
GFYHEADGYH   FETLSGTSAK   DAFIMGDDGA   LYYFDDQGVM   VTGKQRVHQD   QYFFLPNGIA  1200
LTDAFVQSAD   GQRQYYDKTG   RLVINQYVTD   HQANAFRVDA   DGNVVRNQAL   TVDGHEQYFG  1260
TNGVQAKAVL   IRTDDNQARY   YEANSGNLVK   QQFILDTDGH   WLYADAAGDL   ARGQITVGQD  1320
TLYFDDNNHQ   VKDDFVYDTN   GVHYFNGTTG   AEIKQDYAFH   DGKWYYFDDL   GRMVTGLQRI  1380
NGEYRYFDAN   GVQLKGGTVT   DPLTHQTYTF   DAQTGVGTLV   TF                      1422

SEQ ID NO: 6            moltype = DNA   length = 4269
FEATURE                 Location/Qualifiers
misc_feature            1..4269
                        note = 2919 gtf with heterologous signal sequence
source                  1..4269
                        mol_type = other DNA
                        organism = synthetic construct
SEQUENCE: 6
gacacagtcc   ttccgtcaga   acaaagagcc   acgagacgga   cacagacaac   acaaacaagc    60
gaagacacaa   gcgccacaaa   gacgcctgct   agcgcttcaa   cgagcagtc   agtgaacgtg   120
gacacatcag   atcttccgga   cagctcaagc   acggtggtga   attcaacgtc   agcctcagca   180
agcgtcgtgt   cagactccagt   cgctgtccct   gatacgggat   cacagttcac   atcatcaagc   240
ggcagcatgt   caagcagctt   tgttaaaagc   tcactggcag   ctacgacgtc   agatgcttca   300
ggctcacaaa   gcgccgctgt   gacatcagca   acagtttcaa   gcgtggcgac   gagctcatca   360
gcgtcatcag   ttacaacagc   cacgagcgaa   tcagcggtta   ttagctcagc   agttagcgat   420
ggctatcacg   atgaaggagg   cgattgggtt   tactacagag   gcgcaaaaaa   actggttgga   480
agacaaacga   ttgatacatt   tgccgtttac   ttcgatgcag   atggaaaaca   ggttaaagga   540
gactggagag   agtcagacgg   aaacagagcg   tactatgatg   gccaagaagg   cagagccctt   600
acgcaaacac   aggcagttaa   cggagtcatc   tatggattta   atcaatcagg   atatcagatt   660
aagaacgatt   tcgccagaca   ggctaacaga   gacacgtatt   actttgatgc   tcaaggacat   720
gtggttacgg   gcatccagac   aattgcaaat   aaagtttatg   atttcgatga   acaaggaaga   780
```

```
atgctgaaag gaattgccac gtcagtcgac gataaaatga tgtatttcga cgaccaaacg  840
ggcgtgggcc aacctgccga ccaccctgag tttaatccgg aaacggagcc ggtcccggat  900
gacaacatta aacataacgc tgcgcacgga acgacacctg ctgattttga tagcatggcc  960
ggataccttac cggcggatac atggtataga cctacagaca ttctggagaa tggcaaaca  1020
tggagagaaa gccagcctac ggagttcaga ccgcttcttg ccacatggcg gcctacgaaa  1080
caaacgcaag cagattatgt taattacatg aaccatgctc tggatatgtc aaatgcgagc  1140
gtgagcgctg ccgatagcga ggcaacactt acagccgcga cggatgccat ccaagctgca  1200
gtcgaacatc aaattacagt gagacagtca acggcatggc ttagaaact tatggcggca  1260
tttgtcgtga cgcaaccgca gtggaataaa acatgcagag atgtcaacga cgatcacctg  1320
caaggaggag cgcttacatt cgaaaataac ggcgatacgg acgcaaatag cgattacaga  1380
cttatgaata gaacgcctac aaaccaaaca ggagaaagac tttaccacat tgacgactca  1440
cttggaggat acgaactgct tctggccaac gatgttgata cagcaatcc tcaagtgcag  1500
gctgagcaac ttaattggct ttattacctg atgcattttg gcgatattac agctgacgac  1560
cctgacgcca acttcgacgc gattagaatc gatgcggtcg ataatgtcga cgcagacctt  1620
cttcaactgg ctgctcaata tttcagagac gcatacggaa tggcaacaac agacgctaca  1680
agcaataaac atctgtcaat tcttgaagac tggtcacata atgatccggc gtacatgcaa  1740
gctcatggaa acgatcaact tacgatggat gactatatgc acacaacaact tatttggtca  1800
ctgacaaaac cggaggctca aagaggaaca atggctgaat ttatgactt ttatcttaca  1860
aatagagcga acgatgatac agaaaatacg gctcaacctt catattcatt cgttagagca  1920
catgattcag aagttcaaac agtgattgca gaaattgtta caaaactgca tcctgaggcg  1980
ggcaatggac tgatgccgac agaagagcaa atggcagaag cctttaagat ctataatgcc  2040
gatcagaaaa aagcagtgaa aacatataca cactacaata tgccttcagc ttatgcaatg  2100
ctgcttacga ataaagacgt cattcctaga atttactatg gagatcttta tacgatgat  2160
ggacaattca tggctacaaa gtcacctat ttgacgcta tcagcgcgat gctgcaagcg  2220
agaacgaagt atgtcgcagg cggccagacg atggcagtgg atcagcacga cgtgcttaca  2280
agcgtgagat ttggcaaagg cgcaatgaca gcatccagcc tgggcaatgc agagacaaga  2340
acggagggag ttggccttat catttcaaat aatccgaaac tgcaactggg ccagcaggat  2400
aacgtcgttc ttcatatggg cctggcgcac gcaaaccagg cctttagagc agttgttctt  2460
acaacagcga cgggcctgac aatctacaat gacgatgatg caccgattag atatacagac  2520
aataaaggcg acctgattt caacaaccat gatgtctacg cgtcctgaa cccgcaggtt  2580
tcaggcttcc tggccatgtg ggttcctaca ggcgcacctg ctaaccaaga tgctagatca  2640
acagcaagca caactcatc aacgatggc tcagcatatc attcaaatgc tgcgctggat  2700
tcacaagtta ttttcgaatc attctcaaat ttccaagcaa tgccgacgtc acatgacaca  2760
tacacgaatg tggttctggc caaccacgcc gaccagcttc acgattgggg cattacatca  2820
gtgcagctgg caccgcagta tagaagctca acagacggca cgttcctgga tgcaattatc  2880
cagaatggct atgccttcac agatagatac gatcttggct ttggcacacc tacaaaatac  2940
ggcgacgaca cggatctgag aaatgtgatt aaggcgcttc atgccaacgg catgcaggtt  3000
atggccgact tcgtcccgga ccaactttat acacttccgg gaaaagagct ggtgcaagtc  3060
acgagaacga ataacatggg cgaacctgat cacactcag acattcaaca tattctgtac  3120
gttacgtcaa cgagaggcgg aggagaatat caaaaacagt atgcggcga gtttcttgaa  3180
agactgagag cactgtaccc tgacctttt acgacaagac aaattagcac aggccaaaca  3240
attgacgatt cagtgaagat caaagagtgg tcagctaagt acctgaacgg cacagctatc  3300
caaggagggg gcgcaggcta tgttctgaga gataatggca caaatgccta ctacaaagtt  3360
acagcgaatg atggaaatgt caatcttcct aaacaacttc ttggacagcc ggttatgacg  3420
ggcttctacc acgaggccga tggatatcac ttcgagacac tgtcaggaac atcagccaag  3480
gatgcgttta tcatgggaga tgacgagcg ctttattact ttgatgacca aggcgttatg  3540
gtgacaggaa aacagagat tcatcaagac cagtacttc ttctgcctaa cggaattgct  3600
ctgacagacg cgttcgttca atcagcagac ggacaaaagac agtattatga caaaacggga  3660
agacttgtta tcaaccagta tgtgacagat caccaagcta atgcttttag agtcgatgct  3720
gatggcaacg tggttagaaa ccaagcactt acagttgatg gacacgaaca atatttcgga  3780
acaaatggag tccaggctaa agcggttctg attagaacga atgataatca agcgagatat  3840
tacgaagcta actcaggcaa tctggttaag caacaattca ttcttgacac agatggccac  3900
tggctgtacg ccgatgcagc cggagatctt gctagaggac agattacagt gggacaggat  3960
acactgtatt tcgacgataa taccaccaa gttaaggatg attttgtcta tgatacaaac  4020
ggcgttcatt atttcaatgg aacgacagga gctgagatta aacaagatta cgcatttcac  4080
gacggcaaat ggtactactt cgatgatctg ggaagaatgg ttacaggact gcaaagaatt  4140
aacggcgaat atagatattt tgacgctaat ggcgttccaac ttaagggagg aacagtcacg  4200
gacccctctta cacatcaaac atatacattt gatgctcaaa caggcgttgg aacgctggtc  4260
acgttttga                                                           4269
```

SEQ ID NO: 7          moltype = DNA   length = 4392
FEATURE               Location/Qualifiers
source                1..4392
                      mol_type = unassigned DNA
                      organism = Lactobacillus fermentum

SEQUENCE: 7

```
ttgcaagacg agtcacagaa gtttagaaaa aagatgtata agtccggaaa gttttgggta   60
gctgccggtg ctttgtttgt tgggctggca ttcgctggta acgcgcaggc agatactcta  120
ttaccaagtg aacaacgtgc aacacagacg acacagacga cagacacg tgaagacacg  180
tccgccacta agacgccggc atcggcgtcg acttcaagct cagacaatgt tgacacgagt  240
gacctgcctg acagtgcaag tgcggtggtt gatagtgcag ttacaagtac aagtacaagt  300
gcaagtgtag tgagtgatag cgtcgccgtg ccagatactg gatcacaatt tatgagttcg  360
tcagcgccag cgtcatcagc gttttgttaaa ccgtcactaa cgtcaacaac tagtggtgct  420
tccggcagtc agtcatcagc ggtgactagc gcaaacgatca gttcggtggc aactagtagt  480
tcagcatctt cagtgacaac agccacaagt gaatcggctg tggtaagcag cgccgtgtca  540
gatggttacc atgatgaagg tggtgattgg gtcattatc gagctgggaa aaagttactc  600
ggtcgacaaa cgattgatac gtttgcggtt tactttgacg ccgatggcaa acaagtcaag  660
ggtgattggc gtgaaagtga tggtaaacgt gcgtattatg atgggcaaga aggacgagca  720
ttaacgcaaa cgcaagcagt caatggcgtt atctacggtt ttaatcaaag cggctatcaa  780
```

-continued

```
atcaagaatg atttcggcca aacagcgaat cgagatacgt attatttcga cgcacaaggt    840
catgttgtca cgggaatcca aacaattgca aacaaggttt atgattttga tgagcaaggt    900
cgaatgctga aaggcattgc cacgtcagtt gatgacaaga tgatgtattt tgatgatcaa    960
acaggtgttg acaaccggc tgatcatcct gaattcaacc ctgaaacgga accggttcct   1020
gacgacaata tcaaacataa tgcagcacat ggtacgacac cagaagattt tgattcgatg   1080
gctgactacc tgacggctga tacttggtat cgcccaaccg atattttgga aaatggtgag   1140
acgtggcgcg aatcgcaacc aactgaattt cgaccactgt tagcaacttg gtggccaaca   1200
aaacaaaccc aggccgatta cgtgaactac atgaatcacg cattagatat ggcaaatgca   1260
ggtgtgtcag ctgctgattc agaagccacg ttaactgcgg caaccgatgc tattcaagcg   1320
gttgttgagc accaaatcac ggtgcgtcaa tcaacgcgtt ggttacgtga attaatggcc   1380
gcatttgttg tgacacagcc acagtggaat aaaacaagtg aagatgtgaa tgatgatcat   1440
ttgcaaggtg gggcattaac atttgaaaat aacggcgaca cagacgctaa ttcgattat    1500
cgcctcatga accgcacgcc aacaaatcag actggcgaac gcttgtacca cattgatgac   1560
tcacttggtg gttacgaatt attgctggca aatgacgttg acaattcaaa tccacaagtt   1620
caggcagaac aattgaattg gttgtactac ttaatgcatt ttggggatat tacagctgat   1680
gatccggacg caaattttga tgccatacgg attgatgcgg tcgataatgt cgatgctgat   1740
ttacttcaac tagcagccca gtatttccgg gatgcctatg gcatggctac aactgacgca   1800
acatcaaata gcatctttc aattcttgag gattgggagc ataacgatcc ggcgtatatg   1860
caagcacacg gcaatgatca attaacgatg gatgattata tgcacacaca gttgatttgg   1920
tcattaacca agcccgaggc acaacgcggg accatggcac gctttatgga cttctatctc   1980
accaaccgtg ctaatgatga tacagaaaac acggcgcaac tagttactc gtttgtgcgt   2040
gcccatgata gcgaagtaca acagtcatt gctgagatcg tgacgaagct gcatccagaa   2100
gcaggaaatg ggttaatgcc tacgaagaa caaatggcag aagcgtttaa gatttacaat   2160
gcggaccaaa agaaggccgt taagacttac acacattaca atatgccatc tgcatacgcc   2220
atgctgttaa cgaacaagga tgttattcca cgaattact atggtgactt gtacactgat   2280
gatgggcaat tcatgcgac aaaatcacct tattttgatc catgttacaa   2340
gcacgcacga agtatgtagc tggtggacag acgatggcgg ttgaccagca cgacgtcttg   2400
actagcgttc ggtttggtaa gggggccatg acggccaatg atttaggga tgctgagacc   2460
cggactgagg gtgtgggatt aattattagc aacaacccaa agttgcaatt gggacaacaa   2520
gacaacgtgg tgttacacat gggacttgcg cacgcgaatg gtcagtcgta   2580
ctaacgaccg cgaccggatt aaccattat aatgacgatg atgctccgat tcgttatacc   2640
gataataagg gtgatttaat tttcactaac catgacgtat atggcgtgtt gaatccacaa   2700
gtgtcaggct tcttggcaat gtgggtgcca actggtgcac cagcgaacca ggatgcgcga   2760
tctactgcgt caaccaacat gtcaacggat ggatctgcct accattctaa tgcggctttg   2820
gatagtcaag taatctttga atcattttcg aatttccagg ctatgccaac aagtcatgac   2880
acatacacca acgttgtgtt agccaatcat gctgaccagt tgcacgattg gggaataact   2940
tcggtacagt tagcaccaca ataccggtct caaccgacg gtacctttt agacgcgatt   3000
attcaaaatg gctatgcctt cactgaccgt tatgatttag ggtttggtac gccaactaaa   3060
tacggggatg atacggattt gcggaacgtc atcaaagcat tgcatgcaaa tggcatgcaa   3120
gtaatggctg attttgtgcc ggatcaattg tatacattac caggtaagga attggtacaa   3180
gtcacccgaa caaacaatat gggtgagcca gatacgcatt ctgacatcca acatattta   3240
tatgtgacga gcactcgtgg tggtggtgac tatcagaaac agtacggtgg tgagttcctt   3300
gcacgattgc gtgaacgata cccagattta tttacgaac tgcaaatttc gaccggacaa   3360
acaattgatg attcagtaaa aattaaagaa tggtcagcta agtatttgaa tggtaccgca   3420
attcaaggac gtggagctgg ctatgtgctg cgtgataatg gtacaaatgc ttattacaag   3480
gtgacagcaa atgacggtaa tgtgaactta ccaaagcaat tactcggcca accggtgatg   3540
accggattct atcacgaggc agatgtttat cattttgata tcagtgg tacgtcggcc   3600
aaagatgcct ttattatggg cgacgatggg gcactgtatt attttgatga tcagggtgtt   3660
atggtaacgg gtaagcaacg tgtgcaccaa gatcagtatt tcttcctgcc aaatggtatt   3720
gctttgcagag atgctttcgt acaaactgct gatggtcaac gtcagtacta tgataaaaca   3780
ggtcgtctgg tcattaatca atatgtgact gaccaccaag cgaatgcgtt ccgggttgat   3840
gcagacggta acgttgtccg caatcaagct ttgactgttg acggccatga acaatatttc   3900
ggcacaaacg tgtccaagc gaaagcagtg ctcattcgaa ctgacgataa tcaggcgcgc   3960
tactacgaag ccaatagtgg taatctcgtg aagcaacagt ttattcttga tacagatgga   4020
cattggttgt acgcggatgc tgcaggtgac ttggcacgcg gacaaattac aattggcaa    4080
gacacgttgt atttttgatga taataatcac caggtaaaag atgatttcgt ctatgatact   4140
aacggtgtgc attatttaa tggcacaaca ggcgctgaaa tcaaacaaga ttacgcgttt   4200
catgatggca aatggtacta ttttgatgat ttgggacgaa tggtaaccgg cttgcagcgt   4260
attaatggtg agtatcgcta ttttgatgct aatggtgtgc aactaaaggg cggtaccgtg   4320
accgatccac taacgcacca aacgtacact tttgatgcga aaactggtgc tggtacgttg   4380
gtgacgattt aa                                                        4392
```

SEQ ID NO: 8           moltype = AA   length = 1463
FEATURE                Location/Qualifiers
source                 1..1463
                       mol_type = protein
                       organism = Lactobacillus fermentum
SEQUENCE: 8
MQDESQKFRK KMYKSGKFWV AAGALFVGLA FAGNAQADTV LPSEQRATQT TQTTQTSEDT    60
SATKTPASAS TSSSDNVDTS DLPDSASAVV DSAVTSTSTS ASVVSDSVAV PDTGSQFMSS   120
SAPASSAFVK PSLTSTTSGA SGSQSSAVTS ANDSSVATSS SASSVTTATS ESAVVSSAVS   180
DGYHDEGGDW VYYRAGKKLL GRQTIDTFAV YFDADGKQVK GDWRESDGKR AYYDGQEGRA   240
LTQTQAVNGV IYGFNQSGYQ IKNDFGQTAN RDTYYFDAQG HVVTGIQTIA NKVYDFDEQG   300
RMLKGIATSV DDKMMYFDDQ TGVGQPADHP EFNPETEPVP DDNIKHNAAH GTTPEDFDSM   360
ADYLTADTWY RPTDILENGE TWRESQPTEF RPLLATWWPT KQTQADYVNY MNHALDMANA   420
GVSAADSEAT LTAATDAIQA VVEHQITVRQ STAWLRELMA AFVVTQPQWN KTSEDVNDDH   480
LQGGALTFEN NGDTDANSDY RLMNRTPTNQ TGERLYHIDD SLGGYELLLA NDVDNSNPQV   540
QAEQLNWLYY LMHFGDITAD DPDANFDAIR IDAVDNVDAD LLQLAAQYFR DAYGMATTDA   600
TSNKHLSILE DWSHNDPAYM QAHGNDQLTM DDYMHTQLIW SLTKPEAQRG TMARFMDFYL   660

```
TNRANDDTEN  TAQPSYSFVR  AHDSEVQTVI  AEIVTKLHPE  AGNGLMPTEE  QMAEAFKIYN   720
ADQKKAVKTY  THYNMPSAYA  MLLTNKDVIP  RIYYGDLYTD  DGQFMATKSP  YFDAISTMLQ   780
ARTKYVAGGQ  TMAVDQHDVL  TSVRFGKGAM  TANDLGDAET  RTEGVGLIIS  NNPKLQLGQQ   840
DNVVLHMGLA  HANQAFRAVV  LTTATGLTIY  NDDDAPIRYT  DNKGDLIFTN  HDVYGVLNPQ   900
VSGFLAMWVP  TGAPANQDAR  STASTNMSTD  GSAYHSNAAL  DSQVIFESFS  NFQAMPTSHD   960
TYTNVVLANH  ADQLHDWGIT  SVQLAPQYRS  STDGTFLDAI  IQNGYAFTDR  YDLGFGTPTK  1020
YGDDTDLRNV  IKALHANGMQ  VMADFVPDQL  YTLPGKELVQ  VTRTNNMGEP  DTHSDIQHIL  1080
YVTSTRGGGD  YQKQYGGEFL  ARLRERYPDL  FTTRQISTGQ  TIDDSVKIKE  WSAKYLNGTA  1140
IQGRGAGYVL  RDNGTNAYYK  VTANDGNVNL  PKQLLGQPVM  TGFYHEADGY  HFETLSGTSA  1200
KDAFIMGDDG  ALYYFDDQGV  MVTGKQRVHQ  DQYFFLPNGI  ALTDAFVQTA  DGQRQYYDKT  1260
GRLVINQYVT  DHQANAFRVD  ADGNVVRNQA  LTVDGHEQYF  GTNGVQAKAV  LIRTDDNQAR  1320
YYEANSGNLV  KQQFILDTDG  HWLYADAAGD  LARGQITIGQ  DTLYFDDNNH  QVKDDFVYDT  1380
NGVHYFNGTT  GAEIKQDYAF  HDGKWYYFDD  LGRMVTGLQR  INGEYRYFDA  NGVQLKGGTV  1440
TDPLTHQTYT  FDAKTGAGTL  VTI                                             1463

SEQ ID NO: 9           moltype = AA   length = 1426
FEATURE                Location/Qualifiers
REGION                 1..1426
                       note = MISC_FEATURE - mature 2918 gtf
source                 1..1426
                       mol_type = protein
                       organism = Lactobacillus fermentum
SEQUENCE: 9
DTVLPSEQRA  TQTTQTTQTS  EDTSATKTPA  SASTSSSDNV  DTSDLPDSAS  AVVDSAVTST    60
STSASVVSDS  VAVPDTGSQF  MSSSAPASSA  FVKPSLTSTT  SGASGSQSSA  VTSANDSSVA   120
TSSSASSVTT  ATSESAVVSS  AVSDGYHDEG  GDWVYYRAGK  KLLGRQTIDT  FAVYFDADGK   180
QVKGDWRESD  GKRAYYDGQE  GRALTQTQAV  NGVIYGFNQS  GYQIKNDFGQ  TANRDTYYFD   240
AQGHVVTGIQ  TIANKVYDFD  EQGRMLKGIA  TSVDDKMMYF  DDQTGVGQPA  DHPEFNPETE   300
PVPDDNIKHN  AAHGTTPEDF  DSMADYLTAD  TWYRPTDILE  NGETWRESQP  TEFRPLLATW   360
WPTKQTQADY  VNYMNHALDM  ANAGVSAADS  EATLTAATDA  IQAVVEHQIT  VRQSTAWLRE   420
LMAAFVVTQP  QWNKTSEDVN  DDHLQGGALT  FENNGDTDAN  SDYRLMNRTP  TNQTGERLYH   480
IDDSLGGYEL  LLANDVDNSN  PQVQAEQLNW  LYYLMHFGDI  TADDPDANFD  AIRIDAVDNV   540
DADLLQLAAQ  YFRDAYGMAT  TDATSNKHLS  ILEDWSHNDP  AYMQAHGNDQ  LTMDDYMHTQ   600
LIWSLTKPEA  QRGTMARFMD  FYLTNRANDD  TENTAQPSYS  FVRAHDSEVQ  TVIAEIVTKL   660
HPEAGNGLMP  TEEQMAEAFK  IYNADQKKAV  KTYTHYNMPS  AYAMLLTNKD  VIPRIYYGDL   720
YTDDGQFMAT  KSPYFDAIST  MLQARTKYVA  GGQTMAVDQH  DVLTSVRFGK  GAMTANDLGD   780
AETRTEGVGL  IISNNPKLQL  GQQDNVVLHM  GLAHANQAFR  AVVLTTATGL  TIYNDDDAPI   840
RYTDNKGDLI  FTNHDVYGVL  NPQVSGFLAM  WVPTGAPANQ  DARSTASTNM  STDGSAYHSN   900
AALDSQVIFE  SFSNFQAMPT  SHDTYTNVVL  ANHADQLHDW  GITSVQLAPQ  YRSSTDGTFL   960
DAIIQNGYAF  TDRYDLGFGT  PTKYGDDTDL  RNVIKALHAN  GMQVMADFVP  DQLYTLPGKE  1020
LVQVTRTNNM  GEPDTHSDIQ  HILYVTSTRG  GGDYQKQYGG  EFLARLRERY  PDLFTTRQIS  1080
TGQTIDDSVK  IKEWSAKYLN  GTAIQGRGAG  YVLRDNGTNA  YYKVTANDGN  VNLPKQLLGQ  1140
PVMTGFYHEA  DGYHFETLSG  TSAKDAFIMG  DDGALYYFDD  QGVMVTGKQR  VHQDQYFFLP  1200
NGIALTDAFV  QTADGQRQYY  DKTGRLVINQ  YVTDHQANAF  RVDADGNVVR  NQALTVDGHE  1260
QYFGTNGVQA  KAVLIRTDDN  QARYYEANSG  NLVKQQFILD  TDGHWLYADA  AGDLARGQIT  1320
IGQDTLYFDD  NNHQVKDDFV  YDTNGVHYFN  GTTGAEIKQD  YAFHDGKWYY  FDDLGRMVTG  1380
LQRINGEYRY  FDANGVQLKG  GTVTDPLTHQ  TYTFDAKTGA  GTLVTI                  1426

SEQ ID NO: 10          moltype = DNA   length = 4281
FEATURE                Location/Qualifiers
misc_feature           1..4281
                       note = 2918 gtf with heterologous signal sequence
source                 1..4281
                       mol_type = other DNA
                       organism = synthetic construct
SEQUENCE: 10
gatacagtgc  tgcctagcga  gcaaagagca  acacagacga  cacaaacaac  gcagacatca    60
gaggatacga  gcgcgacgaa  gacaccggca  agcgcatcaa  cgtcaagcag  cgataacgtg   120
gatacgtcag  atcttccgga  tagcgccagc  gcagttgtcg  attcagcggt  tacatcaaca   180
agcacgtcag  cctcagtggt  gagcgatagc  gttgcagtcc  cggatacggg  atcacaattt   240
atgtcatcat  cagctcctgc  gagcagcgcg  tttgttaaac  ctagccttac  gtcaacgacg   300
tcaggagcga  gcggctcaca  gagctcagca  gtgacaagcg  ccaatgattc  aagcgtcgct   360
acaagctcat  cagcttcatc  agttacgaca  gcaacaagcg  agtcagccgt  tgtctcaagc   420
gcggtcacag  acggctatca  tgacgaagga  ggagattgga  tttactacag  agcaggaaga   480
aaactgcttg  gaagacagac  aattgatacg  tttgctgttt  actttgatgc  tgacggaaaa   540
caagtgaaag  cgactggag  agaatcagat  ggaaagagag  cgtattatga  tggacaagaa   600
ggaagagccc  ttacgcaaac  gcaagccgtt  aatgagtga  tctatggatt  caatcaatca   660
ggataccaga  tcaaaacga  ttttggccag  acagcgaaca  gagatacata  ctacttcgac   720
gcacaggcac  atgtggttac  aggcatccaa  acaatcgcaa  ataaagttta  tgacttcgat   780
gaacaaggca  gaatgcttaa  aggaattgcc  acatcagtcg  atgacaagat  gatgtatttt   840
gacgatcaaa  caggcgtggg  acaacctgca  gatcaccctg  agtttaaccc  ggaaacagaa   900
ccggtgcctg  acgataacat  caagcataat  gcagcccacg  gcacaacacc  tgaagatttt   960
gatagcatgg  cggactatct  gacagctgat  acatggtata  gacctacaga  tattctggag  1020
aatggagaa  catggagaga  gagccaaccg  acggaattca  gaccgctgct  tgcaacttgg  1080
tggcctacaa  aacagacaca  agcagattat  gtgaactata  tgaaccacgc  acttgacatg  1140
gctaatgctg  gcgttagcgc  tgcggattca  gaggcaacac  ttacagcggc  tacggatgcc  1200
attcaggctg  ttgttgagca  ccaaattacg  gttagacaaa  gcacggcctg  cttagaaaa  1260
cttatggcgg  cttttgttgt  tacacaacct  caatggaata  agacgagcga  agatgtcaat  1320
gatgatcacc  ttcaaggagg  cgcactgaca  tttgagaata  acggagacac  agatgcaaat  1380
```

```
agcgattata gacttatgaa tagaacaccg acaaatcaaa cgggcgagag actttatcat   1440
attgatgact cactgggagg ctacgagctg cttcttgcaa acgatgtgga caactcaaac   1500
ccgcaggttc aggcggaaca acttaactgg ctttactatc ttatgcattt cggagatatt   1560
acagccgatg acccggatgc taactttgac gcgatcagaa ttgacgccgt tgataatgtc   1620
gacgctgacc tgcttcagct tgctgcccaa tactttagag atgcatatgg aatggccaca   1680
acagacgcca cgagcaataa acaccttca atccttgagg attggagcca taacgatcct   1740
gcttatatgc aggcacatgg aaatgaccag cttacaatgg atgactacat gcacacacaa   1800
ctgatttggt cactgacgaa accggaagca caaagaggaa cgatggcaag atttatggac   1860
ttttatctta caaatagagc taacgatgat acagaaaaca cagcgcaacc ttcatattca   1920
tttgttagag cacacgactc agaagtgcag acagttattg cagaaattgt tacgaaactt   1980
cacccggagg caggcaacgg ccttatgcct acggaggaac agatggcaga ggcgtttaag   2040
atctacaatg cagaccaaaa gaaagcggtg aaaacatata cacactataa catgccttca   2100
gcctacgcta tgctgctgac aaataaggat gtgattccta gaatctacta cggcgatctt   2160
tacacggacg acggccagtt catggcaaca aagtcaccgt atttcgatgc aatttcaaca   2220
atgctgcaag caagaacaaa atatgttgca ggcggacaaa cgatggcggt tgaccaacat   2280
gatgtcctga cgagcgtgag atttggcaaa ggcgcgatga cagcaaatga ccttggagac   2340
gcggaaacga gaacagaggg cgtgggactg atcatcagca caaccctaa gctgcaactg   2400
ggacagcagg ataacgtggt ccttcatatg ggcctgccaa cgcgaatca ggcttcaga   2460
gcagtcgtgc ttacaacagc cacaggactg acgatctaca acgacgatga cgctcctatt   2520
agatatacgg acaataaggg cgacctgatc tttacgaatc acgatgttta cggcgttctg   2580
aacccgcagg ttagcggctt ccttgctatg tgggttccga cgggcgcacc tgccaatcaa   2640
gacgcaagaa gcacggcttc aacgaatatg tcaacggatg gatcagctta tcattcaaac   2700
gcagctctgg attcacaagt tatctttgag tcatttagca actttcaagc aatgccgaca   2760
tcacacgata catacacgaa tgttgtcctt gcaaaccatg cagaccaact tcacgattgg   2820
ggaattacgt cagtgcaact tgcaccgcaa tatagatcaa gcacagacgg aacgtttctg   2880
gatgcaatta ttcaaaatgg atatgctttt acagatagat attgatcttgg ctttggaaca   2940
cctacgaagt acggcgacga cacgaccctg agaaatgtga tcaaagccct tcatgcaaac   3000
ggcatgcaag tcatggcaga ttttgttcct gatcaactgt acacacttcc gggcaaagaa   3060
ctggttcaag tgacaagaac aaataacatg ggcgaaccgg atacacacag cgatattcaa   3120
cacatcctgt atgttacatc aacaagagga ggcggagact atcagaaaca atatggcgga   3180
gaatttctgg ctagacttag agaaagatac ccgggaccttt ttacgacgag acaaattagc   3240
acaggccaaa caattgacga cagcgttaag attaaggagt ggtcagcgaa atatctgaac   3300
ggcacagcaa ttcaaggcag aggcgctggc tatgttctga gagataatgg aacgaatgca   3360
tactataaag ttacggccaa tgatgaaaac gtcaatcttc ctaagcaact gctgggcgat   3420
ccggttatga caggcttcta tcacgaagca gacggctacc acttcgagac actgtcaggc   3480
acatcagcca aggacgcatt tatcatggga gatgatggcg cactgtacta tttcgatgac   3540
caaggcgtga tggttacagg aaaacaaaga gttcatcagg atcaatactt ttttctgccg   3600
aatggcatcg ctctgacgga cgctttcgtt caaacagctg atggacagag acagtactac   3660
gataaaacag gcagactggt tattaaccaa tatgtgacaa ccatcaggc gaatgccttc   3720
agagttgatg cggacggaaa tgtcgttaga aaccaagcac ttacagtgga cggacatgaa   3780
cagtatttcg gcacgaacgg agtgcaggca aaagcagttc tgattagaac ggacgataat   3840
caagcgagat attatgaggc aaattcaggc aatctggtga acaacaatt tatccttgac   3900
acagatggcc actggctgta cgcagacgca gcaggcgatc ttgctagagg ccagattaca   3960
atcggccagg atacgctgta ttttgatgat aacaatcacc aagttaaaga tgacttcgtt   4020
tatgatacga atggagtcca ttactttaat ggcacaacag gagcagagat taaacaagat   4080
tacgcattcc atgacggcaa atggtactac ttcgacgacc tgggaagaat ggtcacggga   4140
cttcaaagaa ttaatggaga gtatagatac tttgacgcga acggcgtcca actgaaagga   4200
ggcacagtga cggatcctct gacacatcaa acatatacat ttgatgcaaa aacgggagcc   4260
ggcacgcttg ttacaatttg a                                             4281

SEQ ID NO: 11          moltype = DNA   length = 4521
FEATURE                Location/Qualifiers
source                 1..4521
                       mol_type = unassigned DNA
                       organism = Streptococcus sobrinus
SEQUENCE: 11
atggaaagaa aattgcatta caaattacac aaggtaaaaa aacagtgggt aacgattgcc   60
gttgcctctg ctggtttggc tagcattgtt ggtgctggtt cattaagcca aactgttttct  120
gccgatgact tagccaagga acaagctgcg gctagtcaac aaaaggcagc agccaatcag   180
aatgaggacg aagtggcttc tgatgcagct gatactgcta gtgcaaaagc gacttccgaa   240
aaagaagttg tccaatcttc tgatacaaat tcagaaacta accaagttga aactaaagat   300
caagctagcg ctaaggaaag tgctgacgca gtagccaagc aagcaccaca agctggccct   360
gcaaccacta gccaggttgc aagctcagaa agcagctctg tagcgcctag caaggaagct   420
gataaggcag ctgctggatc agttagccaa aatgaagaag cagcgccct atcgctgcct   480
aatattaaaa agattgatgg taagtattac tatgttatgg cagacggttc ttataagaag   540
aactttgcca ttacagttga tggtcaaatg ctttactttg atgccaaaac aggtgccctg   600
tcttcaacct ctaccttattc tttcagtcaa ggtttgacac caattgtttc tgatttctca   660
gtcaacaaca aggctttcga ttcttctgaa aagagttttta aattggttga tggctatttg   720
acagctgaaa gctggtaccg tcctgctaag atccttgaaa atggtaaaac ttgggttgat   780
tctaaagaaa ctgacctacg cccagttctg atgagctggt ggccaaacaa ggatacgcaa   840
gttgcctacc ttaactacat gagcaaggca cttggtggca aggaagaatt cacaactgaa   900
acctcccaat tgaccttgaa tacagccgct gagttgattc aagctaaaat tgaagctcgc   960
gtttctaaag aacaaggaac aaagtggttg cgtgaagcta tggcagcctt cgttgctacc   1020
caatctcgtt ggaataagga cagcgaacaa tacgataagc tgcaaggcgga              1080
gccctgctct ataccaataa caacttgaca gagtgggcaa attcaaactg gcgcctgctt   1140
aaccgtaccc caactcgtca agatggtaaa acccattact ctaaggctga caaatacggt   1200
ggttatgaat tcctcttggc caacgacgtg gataactcta acccagtcgt tcaagcgaa   1260
atgctcaacc aaatccacta cctcatgaac tggggtgaaa ttgtgatggg tgataagaat   1320
gccaactttg atggtattcg tgtcgatgcc gtggataacg tcaatgcaga tactctgcaa   1380
```

-continued

```
ctctacacca actactttaa ttctgtttat ggtgtcaaca agtctgaagc ccaagccctg 1440
gctcacatct cagtcttgga agcatggtct tacaatgata atgactataa ccaagcacc  1500
aacgggctg  ccctggctat ggacaatggt ctacgctttt ccctgcttta taccttgacc 1560
cgtccgatca atgaacggac acctggtatg tcaaccctga ttaaatcaga atatggtttg 1620
actgaccgga ctaagaatga taagtatgga gatacccaac catctatgt  ttttgttcgg 1680
gcgcatgact cagaagtgca aaccgttatt gcacaaatca tcaaggaaaa aattgatcca 1740
acaaccgatg gtttcacctt caccttggac caattgaaac aggcctttga aatctacaac 1800
aaggatatga atagtgttaa caagcactat acccactata atatcccagc agcctacgct 1860
gtcatgttgt ctaatatgga atccgtaacc cgggttact  atggtgacct cttcaccgat 1920
gatggtcaat acatggcatc taaatctcca tattatgatg ccatcaacac tctccttgcgg 1980
gctcgcattc gttacgcagc cggtggtcaa attatggaac acaattccta caaaccatca 2040
gcagccatga aggcagctca tccagatgct ggtaatgtcc ttggtaacag cgaagtcttg 2100
gtatcggttc gtttcggtca agatgtcatg tctgccgatg atatgactgg tggtaagctg 2160
gctaagacct ctggtatgtt caccctgatt tctaacaacc ctgaattgga attggatgtc 2220
aatgaagaaa tcaaggttaa cgttggtaaa atccatgctg gccaagccta ccgtcccttg 2280
cttttgacaa ctgataaggg tctgcaaaag tatctcaatg attctgatac caagttgacc 2340
aagattgcta caaggatgg  tttcattacc ttcaaggta  gcgaaatcaa gggttacaaa 2400
caagtcgaag tcaatggtta cctctcagtt tgggtaccag ttggtgctaa ggctgaccaa 2460
gacattcgtg tggcccctc  aacagcggct aagggtgaaa aggccaagac ttacacagct 2520
agccaagctt tggaatcgca attaatctac gaaggcttct caaacttcca agattttgtt 2580
caaaaagatt cccaatacac caacaagaag attgctgaaa atactgacct cttcaaggct 2640
tggggtgtta cctcatttga aatggcacca caatacgttt cgcaaccgga tggaaccttc 2700
ctggattcta tcattgaaaa cggttatgcc ttcaccgacc gttatgacct tgccatgagc 2760
aagaacaata aatacggttc taaggaagat ttggccaacg ccctcaaggc ccttcacgca 2820
gctggtattc aagccattgc tgactgggta ccagaccaaa tttaccaact gcctggtaag 2880
gaagttgtta ccgctagccg ggttgacaac tacggtcgtg tgaaagttga ccaaccacta 2940
gttgaaaaac tttatctggc caacaccaag agctcaggaa aagatttcca agctaaatac 3000
ggtggtgaat cttagcaga  actgcaaaag aaatatcctg aaatgttcac gactaagatg 3060
atttcaactg gtaaaaccat tgatccatct gtcaaattga aagaatggtc tgctaagtac 3120
ttcaacggaa ccaacgtcct tgatcgtggt acggactata tcctcagtga tgaaggtact 3180
ggtaaatact ttaccgtcaa tgaaaaaggt gacttcttac ctgcctcatt gactggtaat 3240
aaggatgcca agactggttt ctacaacgat ggtaagggca ttgtttacta cacaaccgcc 3300
ggtaacaagc ctagatcagc cttcgtaaca gaagcaggta atacctatta cttcgactac 3360
accggccata tggtaacagg ccctaacgtt attaacacta aattcatta  cttcttgcca 3420
aatggtatca tgcttaagga tgctattaag caggatgaaa aaggtcgttc cgtatactac 3480
ggtaagactg tgttatgta  caagggtggc cgcgataatg aatggttcgc catgacagac 3540
tctaaggggtc aaatgcgttt ccgtcacttt gacaggtacg gcttcatgtc tatcggtttg 3600
gtaaccatca accaaaatgt tcagtattat gatgaaaatg gtttccaagt taaaggtgaa 3660
tttgtaaccg tcaggatgg  acaaaaccgt tacttcgacc aaggttcagg taacttggtt 3720
aagggacaat tcctcaacaa ggatggcaac tggtactacc ttgatgacca agggctagtt 3780
gctaaaggag ctcagacaat taaggtcaa  aagcttact  ttgacacaaa accggtgtc  3840
caagttaaag gggattttgt aacggataaa gatggcaata ccttcttta  cagtggagat 3900
actggcgatt taatccttgg tcagttcttc tcaactggaa ataacgcttg gttctatgct 3960
gatgaaaatg gtcatgtcgc taagggagct aagactatca gaggtcagaa gtctctactt 4020
gatacaaaaa caggtcagca agctaaggga cgctttatcc gtgatgacaa gggggttcgt 4080
tactatgatg ctgacacagg taccttggta accaacgctt tccttgaaac taaggctggt 4140
tctaaccaat ggtattacat gggagcagat gggtatgctg gtaatgggaa ccagaccata 4200
aaaaatcagc acatgtattt tgatgctgaa actggccaac aagctaaggg aattatagtg 4260
acagatgcca atggtcgcaa gtatttctat gatacttta  ctgcagtcg  tgttgtaaac 4320
caatttgttt tggttaatgg aaattggtat ttctttggtt atgatggagc tgcagtaaca 4380
ggtttccatg atatcaaggg acaacacctt tacttcaatt ccgatggaac acaggccaaa 4440
gggactacgg taaaaattgg caatcgcagc tatacccttg atgctcacac tggtgagctg 4500
acatctgttc attatggctg a                                          4521
```

```
SEQ ID NO: 12          moltype = AA   length = 1506
FEATURE                Location/Qualifiers
source                 1..1506
                       mol_type = protein
                       organism = Streptococcus sobrinus
SEQUENCE: 12
MERKLHYKLH KVKKQWVTIA VASAGLASIV GAGSLSQTVS ADDLAKEQAA ASQQKAAANQ  60
NEDEVASDAA DTASAKATSE KEVVQSSDTN SETNQVETKD QASAKESADA VAKQAPQAGP 120
ATTSQVASSE SSSVAPSKEA DKAAAGSVSQ NEEEAALSLA NIKKIDGKYY YVMADGSYKK 180
NFAITVDGQM LYFDAKTGAL SSTSTYSFSQ GLTPIVSDFS VNNKAFDSSE KSFELVDGYL 240
TAESWYRPAK ILENGKTWVD SKETDLRPVL MSWWPNKDTQ VAYLNYMSKA LGGKEEFTTE 300
TSQLTLNTAA ELIQAKIEAR VSKEQGTKWL REAMAAFVAT QSRWNKDSEQ YDKADHLQGG 360
ALLYTNNNLT EWANSNWRLL NRTPTRQDGK THYSKADKYG GYEFLLANDV DNSNPVVQAE 420
MLNQIHYLMN WGEIVMGDKN ANFDGIRVDA VDNVNADTLQ LYTNYFNSVY GVNKSEAQAL 480
AHISVLEAWS YNDNDYNQDT NGAALAMDNG LRFSLLYTLT RPINERTPGM STLIKSEYGL 540
TDRTKNDKYG DTQPSYVFVR AHDSEVQTVI AQIIKEKIDP TTDGFTFTLD QLKQAFEIYN 600
KDMNSVNKHY THYNIPAAYA VMLSNMESVT RVYYGDLFTD DGQYMASKSP YYDAINTLLR 660
ARIRYAAGGQ IMEHNSYKPS AAMKAAHPDA GNVLGNSEVL VSVRFGQDVM SADDMTGGKL 720
AKTSGMFTLI SNNPELELDV NEEIKVNVGK IHAGQAYRPL LLTTDKGLQK YLNDSDTKLT 780
KIADKDGFIT FKGSEIKGYK QVEVNGYLSV WVPVGAKADQ DIRVAPSTAA GKEKAKTYTA 840
SQALESQLIY EGFSNFQDFV QKDSQYTNKK IAENTDLFKA WGVTSFEMAP QYVSATDGTF 900
LDSIIENGYA FTDRYDLAMS KNNKYGSKED LANALKALHA AGIQAIADWV PDQIYQLPGK 960
EVVTASRVDN YGRVKVDQPL VEKLYLANTK SSGKDFQAKY GGEFLAELQK KYPEMFTTKM 1020
ISTGKTIDPS VKLKEWSAKY FNGTNVLDRG TDYILSDEGT GKYFTVNEKG DFLPASLTGN 1080
KDAKTGFYND GKGIVYYTTA GNKARSAFVT EAGNTYYFDY TGHMVTGPNV INTKFYYFLP 1140
```

```
NGIMLKDAIK QDEKGRSVYY GKTGVMYKGG RDNEWFAMTD SKGQMRFRHF DRYGFMSIGL    1200
VTINQNVQYY DENGFQVKGE FVTDQDGQTR YFDQGSGNLV KGQFLNKDGN WYYLDDQGLV    1260
AKGAQTIKGQ KLYFDTKTGV QVKGDFVTDK DGNTFFYSGD TGDLILGQFF STGNNAWFYA    1320
DENGHVAKGA KTIRGQKLYF DTKTGQQAKG RFIRDDKGVR YYDADTGTLV TNAFLETKAG    1380
SNQWYYMGAD GYAVKGNQTI KNQHMYFDAE TGQQAKGIIV TDANGRKYFY DTFTGSRVVN    1440
QFVLVNGNWY FFGYDGAAVT GFHDIKGQHL YFNSDGTQAK GTTVKIGNRS YTFDAHTGEL    1500
TSVHYG                                                              1506

SEQ ID NO: 13           moltype = AA   length = 1465
FEATURE                 Location/Qualifiers
REGION                  1..1465
                        note = MISC_FEATURE - mature 2920 gtf
source                  1..1465
                        mol_type = protein
                        organism = Streptococcus sobrinus
SEQUENCE: 13
DDLAKEQAAA SQQKAAANQN EDEVASDAAD TASAKATSEK EVVQSSDTNS ETNQVETKDQ     60
ASAKESADAV AKQAPQAGPA TTSQVASSES SSVAPSKEAD KAAAGSVSQN EEEAALSLAN    120
IKKIDGKYYY VMADGSYKKN FAITVDGQML YFDAKTGALS STSTYSFSQG LTPIVSDFSV    180
NNKAFDSSEK SFELVDGYLT AESWYRPAKI LENGKTWVDS KETDLRPVLM SWWPNKDTQV    240
AYLNYMSKAL GGKEEFTTET SQLTLNTAAE LIQAKIEARV SKEQGTKWLR EAMAAFVATQ    300
SRWNKDSEQY DKADHLQGGA LLYTNNNLTE WANSNWRLLN RTPTRQDGKT HYSKADKYGG    360
YEFLLANDVD NSNPVVQAEM LNQIHYLMNW GEIVMGDKNA NFDGIRVDAV DNVNADTLQL    420
YTNYFNSVYG VNKSEAQALA HISVLEAWSY NDNDYNQDTN GAALAMDNGL RFSLLYTLTR    480
PINERTPGMS TLIKSEYGLT DRTKNDKYGD TQPSYVFVRA HDSEVQTVIA QIIKEKIDPT    540
TDGFTFTLDQ LKQAFEIYNK DMNSVNKHYT HYNIPAAYAV MLSNMESVTR VYYGDLFTDD    600
GQYMASKSPY YDAINTLLRA RIRYAAGGQI MEHNSYKPSA AMKAAHPDAG NVLGNSEVLV    660
SVRFGQDVMS ADDMTGGKLA KTSGMFTLIS NNPELELDVN EEIKVNVGKI HAGQAYRPLL    720
LTTDKGLQKY LNDSDTKLTK IADKDGFITF KGSEIKGYKQ VEVNGYLSVW VPVGAKADQD    780
IRVAPSTAAK GEKAKTYTAS QALESQLIYE GFSNFQDFVQ KDSQYTNKKI AENTDLFKAW    840
GVTSFEMAPQ YVSATDGTFL DSIIENGYAF TDRYDLAMSK NNKYGSKEDL ANALKALHAA    900
GIQAIADWVP DQIYQLPGKE VVTASRVDNY GRVKVDQPLV EKLYLANTKS SGKDFQAKYG    960
GEFLAELQKK YPEMFTTKMI STGKTIDPSV KLKEWSAKYF NGTNVLDRGT DYILSDEGTG   1020
KYFTVNEKGD FLPASLTGNK DAKTGFYNDG KGIVYYTTAG NKARSAFVTE AGNTYYPDYT   1080
GHMVTGPNVI NTKFYYFLPN GIMLKDAIKQ DEKGRSVYYG KTGVMYKGGR DNEWFAMTDS   1140
KGQMRFRHFD RYGFMSIGLV TINQNVQYYD ENGFQVKGEF VTDQDGQTRY FDQGSGNLVK   1200
GQFLNKDGNW YYLDDQGLVA KGAQTIKGQK LYFDTKTGVQ VKGDFVTDKD GNTFFYSGDT   1260
GDLILGQFFS TGNNAWFYAD ENGHVAKGAK TIRGQKLYFD TKTGQQAKGR FIRDDKGVRY   1320
YDADTGTLVT NAFLETKAGS NQWYYMGADG YAVKGNQTIK NQHMYFDAET GQQAKGIIVT   1380
DANGRKYFYD TFTGSRVVNQ FVLVNGNWYF FGYDGAAVTG FHDIKGQHLY FNSDGTQAKG   1440
TTVKIGNRSY TFDAHTGELT SVHYG                                        1465

SEQ ID NO: 14           moltype = DNA   length = 4398
FEATURE                 Location/Qualifiers
misc_feature            1..4398
                        note = 2920 gtf with heterologous signal sequence
source                  1..4398
                        mol_type = other DNA
                        organism = synthetic construct
SEQUENCE: 14
gatgacctgg cgaaggaaca agcagccgcc tcacagcaaa aagcagcggc taaccagaat     60
gaagacgaag ttgcatcaga tgcagccgat acagctagcg ccaaagccac gtcagagaaa    120
gaagtggttc agtcaagcga tacaaactca gaaacaaatc aggttgagac gaaagaccaa    180
gcatcagcta aggagagcgc agacgcagtc gcgaaacaag ctcctcaagc aggaccggca    240
acaacgtcac aggtcgccag ctcagagagc agcagcgtgg caccgagcaa ggaggctgac    300
aaggctgccg caggctcagt ctcacagaac gaggaggagg cagcccttc acttgccaac    360
atcaagaaga ttgacggaaa atactattac gttatggccg atggaagcta caagaaaaac    420
tttgcgatta cggttgatgg acagatgctt tactttgacg caaaaacagg cgcactttca    480
tcaacgagca cgtatagctt tcacaaggc ctgacgccga ttgtctcaga cttttagcgtg    540
aacaataagg ctttcgattc atcagaaaag tcatttgaat tgtggacgtg ctacctgaca    600
gccgaaagct ggtacagacc ggccaaaatc ctggaaaacg gaaagacgtg ggtcgactca    660
aaagaaacag atcttagacc tgtcctgatg tcatggtggc cgaacaaaga cacacaagtc    720
gcatatctga attcatgtc aaaagctctg ggaggcaaag aagagtttac gacagagaca    780
tcaactga cactgaatac agcggcagaa cttatccagg cgaagatcga agctagagtg    840
agcaaagagc agggcacaaa atggctgaga gaagcaatgg cagcatttgt ggcgacgcaa    900
tcaagatgga taaagattc agagcaatat gataaagcag atcatcttca aggcggagct    960
ctgctgtaca caaacaacaa ccttacagaa tgggctaatt caaattggag actgcttaat   1020
agaacaccga cgagacagga tggaaaaaca cattactgaa aaggcggata gtatggcgga   1080
tatgagtttc tgctggctaa tgatgtcgat aactcaaatc cggttgtcca agctgaaatg   1140
cttaaccaaa ttcattatct tatgaattgg ggcgaaattg ttatgggcga taagaatgct   1200
aacttcgacg gaatcagagt tgatgcagtt gacaacgtta atgcagatac actgcagctt   1260
tatacaaatt actttaatag cgtttatgga gtcaacaagt cagaagcaca ggcccttgca   1320
catatttcag tccttgaggc atggtcatat aatgataacg actataatca ggatacgaat   1380
ggcgcagcac ttgccatgga taatggcctg agattctaac ttctgtatac gttacaaaga   1440
ccgattaatg aaagaacgcc tggcatgagc acactgatta agagcgaata cggactgacg   1500
gatagaacga aaaacgacaa gtacggcgac acgcaaccta gctatgtctt cgttagagca   1560
catgatagca aggttcaaac ggttattgcc caaattatca aggagaaaat cgatcctaca   1620
acagatggct ttacatttac gctggatcaa ctgaagcaag cctttgaaat ctataacaag   1680
gacatgaact cagtgaataa gcactacacg cattacaata ttcctgctgc atacgctgtt   1740
```

```
atgctgagca acatggaaag cgtgacaaga gtgtactacg gcgaccttt tacggatgac    1800
ggccagtata tggcaagcaa gtcaccttat tatgatgcta tcaatacact tcttagagcg    1860
agaattagat acgccgctgg aggacaaatc atggaacata attcatataa gccgagcgcc    1920
gcaatgaaag ctgcacaccc ggacgccggc aacgtcctgg gcaattcaga ggtcctggtc    1980
tcagtgagat tcggccaaga cgtgatgtca gcagatgata tgacaggcgg aaaacttgga    2040
aaaacatcag gcatgtttac gcttattagc aataacccgg aactggaact tgacgttaat    2100
gaggagatca aagtgaatgt gggcaaaatc catgctggac aagcttatag accgcttctg    2160
cttacaacag ataagggact tcagaagtac cttaatgatt cagacacaaa actgacgaag    2220
atcgctgaca aagacggatt cattacattc aaaggatcag aaattaaggg ctataaacaa    2280
gttgaggtta atggctacct ttcagtttgg gtcccggttg gcgctaaagc agaccaagat    2340
attagagttg ccccgagcac agccgcaaaa ggagaaaagg ctaaaacgta tacagcatca    2400
caggctctgg aatcacagct tatctatgaa ggcttctcaa actttcaaga ctttgttcaa    2460
aaagatagcc aatatacgaa taagaaaatt gcagagaaca cagaccgtgt taaagcatgg    2520
ggagttacgt cattcgagat ggctcctcaa tatgttagcg cacggatgg cacattcctg    2580
gattcaatca ttgaaaacgg ctatgcattc acagacagat acgaccttgc tatgagcaag    2640
aataacaaat atggatcaaa agaggatctg gctaacgcac ttaaggcact tcacgcagct    2700
ggcattcaag ctattgcgga ttgggtgcct gaccaaatct accaactgcc gggcaaagag    2760
gttgtgacag ccagcagagt ggataactat gcagagtta aggtgacca gccgcttgtc    2820
gagaagctgt atctggcgaa tacgaaatca tcaggaaaag atttccaggc taagtacggc    2880
ggagagttcc ttgcggagct gcagaagaaa tacccggaga tgttcacgac aaaaatgatc    2940
agcacaggaa agacaatcga cccgtcagtg aagctgaaag agtggtcagc caagtacttc    3000
aatggaacga acgtgctgga tagaggcaca gactatattc ttagcgatga gggaacggga    3060
aagtatttca cagtcaacga gaagggcgat ttcctgcctg cgagccttac aggcaacaag    3120
gatgccaaaa caggctttta caatgacgga aaaggaattg tttactacac aacagctgga    3180
aacaaggcta agacgcgtt cgtgacagag gctggcaaca catactattt cgactatacg    3240
ggccacatgg tgcaggacc gaatgttatc aacacgaagt tctattactt tcttcctaac    3300
ggcatcatgc tgaaggacgc aattaagcaa gatgaaaagt gaagaagcgt ttattacggc    3360
aagacaggag ttatgtacaa gggcggcaga gataacgaat ggtttgcaat gacagactca    3420
aagggacaga tgagatttag acatttcgat agatatggct tcatgtcaat ggacttgtt    3480
acaatcaacc agaatgttca atactatgat gagaattgcc ttcaggtgaa aggcgaattt    3540
gtcacagatc aggatggaca aacgagatac ttcgaccaag gctcaggcaa tcttgttaaa    3600
ggacagtttc ttaacaaaga tggaaattgg tattatctgg atgatcaagg actggttgct    3660
aaaggagctc aaacgattaa aggccaaaaa ctgtattttg atacgaagac gggcgtgcag    3720
gttaaggagg attttgtgac ggacaaggac ggcaatacat tcttctatag cggagatacg    3780
ggagatctga ttctgggaca attctttca acgggcaata atgcatggtt ttatgcggac    3840
gagaacggac acgtcgccaa aggcgcaaaa acaatcagag acagaagct ttacttcgat    3900
acaaaaacgg gacaacaagc caagggcaga ttcatcagag acgacaaggg agtcagatac    3960
tacgatgcag acacgggcac actggttaca aacgcatttc tggagacgaa ggcgggaagc    4020
aatcagtggt actacatggg cgctgatgga tatgccgtga agggaaacca gacgatcaag    4080
aaccagcata tgtactttga cgctgaaaca ggacagcaag ctaagggaat catcgttacg    4140
gacgcgaacg gcagaaaata cttctatgac acgtttacgg gctcaagagt tgttaatcaa    4200
ttcgttcttg tgaacggaaa ctggtacttt ttgatacg atggagcagc agttacagga    4260
ttccacgata tcaagggcca acatctttat ttcaactcag acggaacgca agcgaaaggc    4320
acgacagtta agatcggaaa tagaagctac acattcgacg cacacacagg cgagcttaca    4380
tcagtccatt acggatga                                                  4398

SEQ ID NO: 15         moltype = DNA   length = 4360
FEATURE               Location/Qualifiers
source                1..4360
                      mol_type = unassigned DNA
                      organism = Streptococcus downei
SEQUENCE: 15
atgattttca tggaaagaaa attacattac aaattacaca aggtcaagaa gcagtgggtg      60
accatcgctg tcgcctctgc tggtttggcc agcgtagtcg gtgctggctc cttgagccaa     120
accgtttctg ctgacgatct tgctaaggac caagcggacg cgactgagca aaaggcatca     180
gccaatcagg aaaagaaga agtagttctt gatcaggttg acacgaccag tgccaaagca     240
acctctgaga aggaagttgc tcaagcttcg gacactagtt cagaagccaa ccaagttcca     300
gcccaagaag aaaagaaggc tgaaaaggca gctgctcctg cgacagcgac accagctcca     360
cagactggtg caaaaaacag ccaaacagct agttcagaag caccagcgac aagcaatcaa     420
gcaagtgaga cagctgaaac tggtgcctta agccaaaaag aagaagcagc agttctttcg     480
cttgataata tcaagaagat tgatggaaag tattactatg ttatggcaga cggctcttat     540
aagaagaact ttgccattac tgttgatggg caaatgcttt actttgatgc caaaacaggt     600
gccctgtctt caacctctac ctattctttc agtcaaggtt tgacaccaat tgtttctgat     660
ttctcagtca acaataaggc ttttgattct tctgaaaaga tttttgaact ggtagatgtt     720
tacctgacag ctgaaagctg gtaccgtcct gctaagattc ttgaaaatgg caagacctgt     780
gtggactcca agaaactgac ccttgtcca gttctcatga gctggtgcc aaacaaggat     840
acccaagttg cctacctcaa ctatatgtcc aaggcgcttg gtggcaagga agagtttaca     900
acagaaacct ctcaaacaac cttgaataca gctgctgagt tgattcaaac caagattgaa     960
gctcgtattt ctaaggaaca agggaccaaa tggcttcgtg aagctatgc tgcttttgta    1020
gcgactcagt ctcgttggag ttacgctagt gagcaatttg ataaaaacga ccacttgcaa    1080
ggtggtgctc tcctttatac taataataaa ttgacccaat gggcagattc taactatcgt    1140
ttgcttaacc gcacccctac ccgacaggat ggcaagcctc attattctaa agctgacgaa    1200
tacggtggtt acgaattcct cttggctaat gacgtggata ctccaacccc agtcgttcaa    1260
gcggaaatgc tcaaccaaat ccactaccatg atgaactggg gctctattgt catgaatgac    1320
aaggatgcca actttgatgg tatccgtgtg gatgcgtgg ataatgtcaa tgcggatacc    1380
ctgcaactct acactaacta ttttaattcg gtttatggtg tcaacaagtc agaagcccaa    1440
gccctagctc acatttcagt attagaagct tggtcttata tgataatga ctataaccaa    1500
gataccaatg gtgcggcctt ggctatggac aatggtctac gcttctccct gctttatacc    1560
ctgacacgtc cacttaatga gcggactcct ggtatgtcaa ccttgattaa gtcacaatat    1620
```

-continued

```
ggtttgactg accggaccaa ggatgacaag tatggcgata ctcagccatc ctatgtcttt   1680
gttcgggctc atgactcaga agtgcaaacc gttattgcgc aaatcatcaa gaaaaaaatt   1740
gatccaacga ctgatggctt taccttcacc ttggaccaat tgaaacaggc ctttgacatc   1800
tacaataagg atatgaatag tgttgataag cactataccc actacaatat tccagcagcc   1860
tacgctgtta tgttgtccaa catggaatca gtaactcggg tttactatgg agacctcttt   1920
accgatgatg tcaatacat ggaaaccaag tctccttact acgatgctat caataccctc   1980
cttagggccc ggattcgtta cgccgctggt ggtcaaacca tggaacacaa ttcctataag   2040
gcatcagcag ctatgaaagc taaaaatcct gatagtggta gtgtgcttgg caacagcgaa   2100
gttctttgtct ctgttcgttt tggtcaagat gtgatgctg ctgacgatat gactggtggt   2160
aagctggcta aaacctctgg tatgttcagc ctgatttcca acaaccctga attagaattg   2220
gatgccaatg aagaaatcag ggtcaatgtt ggtaagattc atgctggtca aacctaccgt   2280
ccattgcttt tgacaaccga taagggtctg caaaagtacc tcaatgattc tgatactaag   2340
ctgaccaagg ttgccgataa ggatggttat atcaccttca agggcagtga aatcaagggc   2400
tacaagcagg ttgaagtcaa tggttaccct tctgtttggg taccagtcgg cgcaaaggca   2460
gatcaagata ttcgtgtggc agcttcaact aaggttaatg gtaaggatca caagacttat   2520
acagctagtc aagcctctaga atcacaatta atctacgaag tttctcaaa cttccaagat   2580
ttcgttaaga aggactccca atataccaat aagaagattg ctgaaaatac cgacctcttt   2640
aaggcctggg gcgtgacctc atttgaaatg gcgccacaat acgtttccgc aactgatggt   2700
accttcctgg attctattat tgaaaatggt tatgccttca ccgaccgtta tgaccttgcc   2760
atgagcaaga caacaagta cggttctaag gaagacttgg ccaatgctct taaggccctc   2820
cacgctgctg gtatccaagc tatcgcagac tgggttccag accaaattta ccaactccca   2880
ggtaaggaag tggtaactgc aagtcgtgtt gataactatg gccgtgttaa gattgaccaa   2940
ccattggttg aaaaacttta cttggccaat accaagagct caggaaaaga cttccaggtc   3000
aaatatggtg gtgaattctt agaagacctg caaaagcaat accctgaaat gtttaccgct   3060
aagatgatt caaccggtaa aaccattgat ccatctgtca aattgaagga atggtcagct   3120
aagtacttga acggaacaaa tgttctgggt cgtggtacag actatgtcct cagcgatgaa   3180
ggaactggca atacttcac tgttaatgaa aagggtgact tcctaccagc agccctgaca   3240
ggtgataggg aagccaagac tggtttctac aatgatggta agggaatgac ctactataca   3300
acggctggta acaaggctaa atctgccttt gtaaccgtag ctggaaatac ctattacttt   3360
gactatactg gttatatggt aacaggacca aacacgatta acagcaaatt ctattacttc   3420
ctgccaaatg gggtaatgct caaggatgct attaagcaag atgagttggg ccgttcggtt   3480
tactatggta aaactggtac catgtacaag gcgacagata aatctcaatg gttgccatg   3540
accgactcta agggtcaaca acgcttccgt cactttgacc gcttcggtat catgtctgta   3600
ggactggtta ccatcaatgg tagtgttcaa tattacgatg aagaaggctt ccaagttaag   3660
ggcgaatttg tcactgataa ggatggtcaa accgttact ttgacgaagg ttctggtaat   3720
ctggttaagg accgcttcct caataaggat ggcaagtggt actatcttga tgataaaggc   3780
ttgctggtca aggggggctca aaccattaag ggtcaaaaac tctactttga caccaagacc   3840
ggtgccaag tcaagggtga ctttgttgcc gacaaggatg caacctgac cttctatagt   3900
ggtgatagtg gtcaaatggt tcaaagtgat ttcttctcaa caggaaataa tgcttggttc   3960
tatgccgatg aaaatggtca tgtcgctaag ggagctaaga ctatcagagg tcagaagctc   4020
tactttgata caaaaacagg tcagcaagct aagggacgct ttatccgtga tgacaagggg   4080
gttcgttact atgatgctga cacaggtgcc ttggtaacca acgctttcct tgaaactaag   4140
gctggttcta accaatggta ttacatggga gcagatggtt atgctgtcaa ggggaaccaa   4200
accataaaaa atcagcacat gtatttgat gctgaaactg gccaacaagc taagggaatt   4260
atagtgacag atgccaatgg tcgcaagtat ttctatgata ctttactgg cagtcgtgtt   4320
gtaaaccaat ttgtttttggt taatggaaat tggtatttct                        4360
```

SEQ ID NO: 16        moltype = AA  length = 1453
FEATURE                Location/Qualifiers
source                 1..1453
                         mol_type = protein
                         organism = Streptococcus downei

SEQUENCE: 16

```
MIFMERKLHY KLHKVKKQWV TIAVASAGLA SVVGAGSLSQ TVSADDLAKD QAAATEQKAS     60
ANQEKEEVVS DQVDTTSAKA TSEKEVAQAS DTSSEANQVP AQEEKKAEKA AAPATATPAP    120
QTGAKNSQTA SSEAPATSNQ ASETAETGAL SQKEEAAVLS LDNIKKIDGK YYYVMADGSY    180
KKNFAITVDG QMLYFDAKTG ALSSTSTYSF SQGLTPIVSD FSVNNKAFDS SEKSFELVDG    240
YLTAESWYRP AKILENGKTW VDSKETDLRP VLMSWWPNKD TQVAYLNYMS KALGGKEEFT    300
TETSQTTLNT AAELIQTKIE ARISKEQGTK WLREAMAAFV ATQSRWSYAS EQFDKNDHLQ    360
GGALLYTNNK LTQWADSNYR LLNRTPTRQD GKPHYSKADE YGGYEFLLAN DVDNSNPVVQ    420
AEMLNQIHYL MNWGSIVMND KDANFDGIRV DAVDNVNADT LQLYTNYFNS VYGVNKSEAQ    480
ALAHISVLEA WSYNDNDYNQ DTNGAALAMD NGLRFSLLYT LTRPLNERTP GMSTLIKSQY    540
GLTDRTKDDK YGDTQPSYVF VRAHDSEVQT VIAQIIKKKI DPTTDGFTFT LDQLKQAFDI    600
YNKDMNSVDK HYTHYNIPAA YAVMLSNMES VTRVYYGDLF TDDGQYMETK SPYYDAINTL    660
LRARIRYAAG GQTMEHNSYK ASAAMKAKNP DSGSVLGNSE VLVSVRFGQD VMSADDMTGG    720
KLAKTSGMFS LISNNPELEL DANEEIRVNV GKIHAGQTYR PLLLTTDKGL QKYLNDSDTK    780
LTKVADKDGY ITFKGSEIKG YKQVEVNGYL SVWVPVGAKA DQDIRVAAST KVNGKDDKTY    840
TASQALESQL IYEGFSNFQD FVKKDSQYTN KKIAENTDLF KAWGVTSPFM APQYVSATDG    900
TFLDSIIENG YAFTDRYDLA MSKNNKYGSK EDLANALKAL HAAGIQAIAD WVPDQIYQLP    960
GKEVVTASRV DNYGRVKIDQ PLVEKLYLAN TKSSGKDFQA KYGGEFLEDL QKQYPEMFTA   1020
KMISTGKTID PSVKLKEWSA KYLNGTNVLG RGTDYVLSDE GTGKYFTVNE KGDFLPAALT   1080
GDREAKTGFY NDGKGMTYYT TAGNKAKSAF VTVAGNTYYF DYTGYMVTGP NTINSKFYYF   1140
LPNGVMLKDA IKQDELGRSV YYGKTGTMYK ATDKSQWFR HFDRFGIMSV                1200
GLVTINGSVQ YYDEEGFQVK GEFVTDKDGQ TRYFDEGSGN LVKDRFLNKD GKWYYLDDKG   1260
LLVKGAQTIK GQKLYFDTKT GAQVKGDFVA DKDGNLTFYS GDSGQMVQSD FFSTGNNAWF   1320
YADENGHVAK GAKTIRGQKL YFDTKTGQQA KGRFIRDDKG VRYYDADTGA LVTNAFLETK   1380
AGSNQWYYMG ADGYAVKGNQ TIKNQHMYFD AETGQQAKGI IVTDANGRKY FYDTFTGSRV   1440
VNQFVLVNGN WYF                                                      1453
```

```
SEQ ID NO: 17            moltype = AA   length = 1409
FEATURE                  Location/Qualifiers
REGION                   1..1409
                         note = MISC_FEATURE - mature 2921 gtf
source                   1..1409
                         mol_type = protein
                         organism = Streptococcus downei
SEQUENCE: 17
DDLAKDQAAA TEQKASANQE KEEVVSDQVD TTSAKATSEK EVAQASDTSS EANQVPAQEE    60
KKAEKAAAPA TATPAPQTGA KNSQTASSEA PATSNQASET AETGALSQKE EAAVLSLDNI   120
KKIDGKYYYV MADGSYKKNF AITVDGQMLY FDAKTGALSS TSTYSFSQGL TPIVSDFSVN   180
NKAFDSSEKS FELVDGYLTA ESWYRPAKIL ENGKTWVDSK ETDLRPVLMS WWPNKDTQVA   240
YLNYMSKALG GKEEFTTETS QTTLNTAAEL IQTKIEARIS KEQGTKWLRE AMAAFVATQS   300
RWSYASEQFD KNDHLQGGAL LYTNNKLTQW ADSNYRLLNR TPTRQDGKPH YSKADEYGGY   360
EFLLANDVDN SNPVVQAEML NQIHYLMNWG SIVMNDKDAN FDGIRVDAVD NVNADTLQLY   420
TNYFNSVYGV NKSEAQALAH ISVLEAWSYN DNDYNQDTNG AALAMDNGLR FSLLYTLTRP   480
LNERTPGMST LIKSQYGLTD RTKDDKYGDT QPSYVFVRAH DSEVQTVIAQ IIKKKIDPTT   540
DGFTFTLDQL KQAFDIYNKD MNSVDKHYTH YNIPAAYAVM LSNMESVTRV YYGDLFTDDG   600
QYMETKSPYY DAINTLLRAR IRYAAGGQTM EHNSYKASAA MKAKNPDSGS VLGNSEVLVS   660
VRFGQDVMSA DDMTGGKLAK TSGMFSLISN NPELELDANE EIRVNVGKIH AGQTYRPLLL   720
TTDKGLQKYL NDSDTKLTKV ADKDGYITFK GSEIKGYKQV EVNGYLSVWV PVGAKADQDI   780
RVAASTKVNG KDDKYTASQ ALESQLIYEG FSNFQDFVKK DSQYTNKKIA ENTDLFKAWG   840
VTSFEMAPQY VSATDGTFLD SIIENGYAFT DRYDLAMSKN NKYGSKEDLA NALKALHAAG   900
IQAIADWVPD QIYQLPGKEV VTASRVDNYG RVKIDQPLVE KLYLANTKSS GKDFQAKYGG   960
EFLEDLQKQY PEMFTAKMIS TGKTIDPSVK LKEWSAKYLN GTNVLGRGTD YVLSDEGTGK  1020
YFTVNEKGDF LPAALTGDRE AKTGFYNDGK GMTYYTTAGN KAKSAFVTVA GNTYYFDYTG  1080
YMVTGPNTIN SKFYYFLPNG VMLKDAIKQD ELGRSVYYGK TGTMYKATDK SQWFAMTDSK  1140
GQQRFHFDR FGIMSVGLVT INGSVQYYDE EGFQVKGEFV TDKDGQTRYF DEGSGNLVKD  1200
RFLNKDGKWY YLDDKGLLVK GAQTIKGQKL YFDTKTGAQV KGDFVADKDG NLTFYSGDSG  1260
QMVQSDFFST GNNAWFYADE NGHVAKGAKT IRGQKLYFDT KTGQQAKGRF IRDDKGVRYY  1320
DADTGALVTN AFLETKAGSN QWYYMGADGY AVKGNQTIKN QHMYFDAETG QQAKGIIVTD  1380
ANGRKYFYDT FTGSRVVNQF VLVNGNWYF                                    1409

SEQ ID NO: 18            moltype = DNA   length = 4230
FEATURE                  Location/Qualifiers
misc_feature             1..4230
                         note = 2921 gtf with heterologous signal sequence
source                   1..4230
                         mol_type = other DNA
                         organism = synthetic construct
SEQUENCE: 18
gatgatctgg caaaggacca agcggctgcc acgaacaga aggcatcagc gaatcaagaa     60
aaggaggaag ttgtttcaga tcaagttgat acgacacgcg ccaaagcaac gtcagaaaaa    120
gaggtggcac aggctagcga tacatcatca gaggccaacc aggttccggc ccaagaggaa    180
aagaaagccg agaaggccgc agcacctgcg acagctacgc cggcaccgca aacgggagcc    240
aaaaatagcc aaacagcctc aagcgaggca ccggctacat caaatcaagc atcagaaacg    300
gcggaaacag gcgcactgtc acaaaaggaa gaagcagctg tccttttcact tgataatatc    360
aaaaagattg acgaaaaata ctactatgtt atggctgatg gatcatataa gaaaaacttt    420
gcgattacag tcgatggcca aatgctgtat tttgatgcaa aaacaggagc tctttcaagc    480
acatcaacat attcattttc acaaggcctg acaccgattg ttagcgactt ctcagtcaat    540
aacaaggcat ttgatagcag cgagaaatca ttcgaacttg tggatggata tcttacgagc    600
gagagctggt acagaccggc aaaaattctg gagaatggaa agacgtgggt tgattcaaaa    660
gagacggacc ttagaccggt gctgatgtca tggtggccga ataaggatac gcaggttgcc    720
tacctgaact atatgtcaaa agcacttggc ggcaaagagg agtttacaac ggagacatca    780
caaacgacac ttaacacggc tgctgaactt atccagacga gatcgaggc aagaattagc    840
aaagaacaag gaacgaagtg gcttagaaa gctatggccg catttgttgc tacgcagtca    900
agatggtcat atgcgtcaga gcagttcgat aaaaacgatc accttcaagg cggagcactt    960
ctgtacacaa ataataagct gacacaatgg gctgactcaa actatagact gcttaacaga   1020
acgcctacga gacaggatgg aaaacctcat tacagcaaag tagacgagta tggaggctat   1080
gagttcctgc ttgcaaatga cgtcgataac tcaaatccgg tggttcaggc agagatgctt   1140
aatcaaattc actatcttat gaactgggc tcaattgtta tgaatgataa ggacgcgaat   1200
ttcgatggaa ttagagtgga tgcggttgac aatgttaatg cggacacact tcaactgtat   1260
acgaattact ttaactcagt ttacggcgtt aacaaatcag aagttcaggc acttgctcat   1320
atcagcgttc ttgaagcatg gagctacaac gacaatgatt acaatcagga tacaaacgga   1380
gctgcactgg ccatggataa tggacttaga ttcagccttc tttacacact gacaagaccg   1440
cttaacgaga gaacacctgg catgtcaaca cttattaagt cacaatatgg ccttacagac   1500
agaacaaaag acgataagta cggcgacacg caaccgtcat acgtgtttgt tagagctcac   1560
gacagcgaag ttcaaacagt tattgctcag attattaaga agaaaattga tccgacaaca   1620
gacggattca catttacact ggaccaactt aaacaagctc tcgatatcta taacaaagat   1680
atgaatagcg ttgataaaca ttacacgcac tacaatattc ctgcagcata cgctgtcatg   1740
ctgtcaaaca tggaatcagt tacaagagtc tattatggcg acctgtttac agatgacggc   1800
caatatatg aaacaaaatc accgtactat gacgccatta tacactgct gagagccaga   1860
atcagatatg cagctggcgg acaaacaatg gaacacaaca gctataaggc gtcagctgcg   1920
atgaaggcga aaaatccga tagcggctca gtccttgaca attcagatac tcttggttac   1980
gttagattg acaagatgt gatgagcgct gacgatatga caggaggcaa acttgctaag   2040
acgtcaggaa tgttctcact gatttcaat aatccggaac tggaacttga cgctaatgaa   2100
gagatcagag tgaatgttgg aaaaatccat gccggccaaa cgtacagacc tcttctgctt   2160
acgacagata agggcctgca aaagtatctt aatgactcag acacgaaact tacgaaggtt   2220
gcagataaag atggctatat tacatttaag ggctcagaga ttaaaggcta taacagggtt   2280
```

```
gaagttaatg gctacctgag cgtctgggtg ccggttggcg ctaaagcaga ccaagacatc  2340
agagtcgcag cttcaacaaa agtcaatgga aaggatgata agacgtacac ggcaagccaa  2400
gcacttgagt cacagcttat ttacgagggc ttctcaaatt tccaagattt cgttaagaaa  2460
gattcacaat atacaaataa gaaaatcgcg gaaaatacag atcttttcaa agcatggggc  2520
gttacatcat ttgaaatggc gcctcagtat gttagcgcaa cagatggcac atttctggat  2580
agcattatcg agaatggata tgcatttacg gatagatatg acctggccat gtcaaaaaac  2640
aacaaatacg gatcaaaaga ggatcttgct aatgcgctta aagctctgca cgcagctggc  2700
attcaagcca ttgcggattg ggttcctgat caaatctacc aacttcctgg caaggaggtt  2760
gttacagcat caagagtcga caattacggc agagtgaaga tcgaccaacc tctggtggaa  2820
aagctgtatc tggctaacac aaagagctca ggcaaagatt ttcaggcgaa atatggcgga  2880
gaatttcttg aagacctgca gaaacagtat cctgaaatgt ttacagcgaa aatgatttca  2940
acaggaaaaa cgattgatcc tagcgttaaa cttaaggagt ggtcagccaa atacctgaat  3000
ggaacaaacg tgctgggaag aggcacagat tatgttcttt cagatgaggg aacgggcaaa  3060
tactttacgg tcaatgagaa aggcgatttc ctgccggctg cacttacagg cgatagagaa  3120
gcaaagacag gattctataa tgacggcaaa ggcatgacgt attacacaac ggccggaaat  3180
aaggcgaaga gcgcgttcgt tacagtggcg ggcaacacat actactttga ttatacggga  3240
tatatggtta caggacctaa tacaattaac agcaagtttt actatttcct tcctaatggc  3300
gttatgctga aggatgcaat taagcaggat gaacttggaa gatcagtcta ctatggcaaa  3360
acgggaacaa tgtataaggc aacggataaa tcacagtggt tcgccatgac agatagcaag  3420
ggacaacaga gattcagaca ttttgataga ttcggaatca tgagcgttgg acttgtcacg  3480
attaatggaa gcgtccagta ttacgacgaa gaaggctttc aagttaaggg agagttcgtg  3540
acggacaaag atggacagac gagatatttt gacgagggaa gcggcaacct ggttaaggac  3600
agattcctga acaaggacgg aaagtggtat taccttgacg ataagggact gcttgtcaag  3660
ggagctcaaa caatcaaggg ccagaaactt tatttcgata caaaaacagg agcgcaagtc  3720
aaaggagact ttgtggctga taaggatgga aacctgacgt tttatagcgg cgattcagga  3780
caaatggtgc agtcagactt cttttagcaca ggcaacaatg catggttta tgcagatgaa  3840
aacggacatg ttgcaaaagg cgcgaagaca atcagaggcc aaaaactgta cttcgacacg  3900
aagacgggac agcaggccaa gggcagattc attagagatg acaaaggcgt gagatactat  3960
gatgcagaca caggcgcact ggtcacaaat gctttcctgg aaacgaaggc tggctcaaat  4020
cagtggtact acatgggagc cgatggatac gcggtgaagg gcaaccagac gatcaagaat  4080
cagcacatgt actttgacgc gggagacgggc caacaagcta agggcatcat cgtcacagat  4140
gcaaatggca gaaagtactt ctatgacacg ttcacgggca gcagagttgt taaccaattt  4200
gttctggtga acggcaattg gtactttga                                     4230
```